US006479254B2

(12) United States Patent
Ebner et al.

(10) Patent No.: US 6,479,254 B2
(45) Date of Patent: *Nov. 12, 2002

(54) APOPTOSIS INDUCING MOLECULE II

(75) Inventors: Reinhard Ebner, Gaithersburg, MD (US); Guo-Liang Yu, Darnestown, MD (US); Steven M. Ruben, Olney, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 5 days.

(21) Appl. No.: 09/027,287

(22) Filed: Feb. 20, 1998

(65) Prior Publication Data

US 2002/0064869 A1 May 30, 2002

Related U.S. Application Data

(63) Continuation-in-part of application No. 09/003,886, filed on Jan. 7, 1998, now abandoned, which is a continuation-in-part of application No. 08/822,953, filed on Mar. 21, 1997, now abandoned.
(60) Provisional application No. 60/013,923, filed on Mar. 22, 1996, and provisional application No. 60/030,157, filed on Oct. 31, 1996.

(51) Int. Cl.[7] ........................ C12P 21/02; C07K 14/525; C07K 19/00; C07K 14/46; C07H 21/04

(52) U.S. Cl. ..................... 435/69.1; 435/69.7; 435/325; 435/320.1; 530/324; 536/23.4; 536/23.5; 536/24.1; 930/144

(58) Field of Search ................ 435/69.1, 69.7, 435/325, 320.1; 536/23.4, 23.5, 23.1, 24.1; 530/350, 300, 324; 930/144

(56) References Cited

FOREIGN PATENT DOCUMENTS

| EP | 0 897 114 A2 | 2/1999 |
|---|---|---|
| JP | 8-191204 | 7/1996 |
| JP | 8-211695 | 8/1996 |
| JP | 9-019330 | 1/1997 |
| WO | WO 96/36720 | 11/1996 |
| WO | WO 97/34911 | 9/1997 |
| WO | WO 97/41831 | 11/1997 |
| WO | WO 98/03648 | 1/1998 |
| WO | WO 98/25967 | 6/1998 |
| WO | WO 98/28424 | 7/1998 |
| WO | WO 98/28426 | 7/1998 |
| WO | WO 98/54323 | 12/1998 |
| WO | WO 99/02563 | 1/1999 |
| WO | WO 99/11662 | 3/1999 |
| WO | WO 99/42584 A1 | 8/1999 |

OTHER PUBLICATIONS

Berzofsky J. A. Intrinsic and extrinsic factors in protein antigenic structure. Science, (Sep. 6, 1985) 229 (4717) 932–40.*
Sutcliffe et al. Antibodies that react with predetermined sites on proteins. Science, (Feb. 11, 1983) 219:660–666.*
Bowie et al. Deciphering the message in protein sequences: tolerance to amino acid substitutions. Science, (Mar. 16, 1990) 247 (4948) 1306–10.*
Greenberg et al. Isolation of cDNAs for perilipins A and B: sequence and expression of lipid droplet–associated proteins of adipocytes. Proc Natl Acad Sci U S A Dec. 15, 1993;90(24):12035–9.*
Hu et al. Cloning and sequencing of the cDNAs encoding two alternative splicing–derived variants of the alpha subunit of the granulocyte–macrophage colony–stimulating factor receptor. Biochim Biophys Acta Sep. 8, 1994;1223(2):306–8.*
Sambrook et al. Molecular Cloning: A Laboratory Manual Second Edition vols. 1, 2 and 3. Cold Spring Harbor Laboratory Press: Cold Spring Harbor, New York, U.S.A. Nov., 1989, pp. 16.2 and 17.2–17.4.*
Barton, G.J. "Protein sequence alignment and database scanning," In: *Protein Structure Prediction. A Practical Approach*, IRL Press publ. Oxford, UK, pp. 31–63 (1996).
George, D.G. et al., "Current Methods in Sequence Comparison and Analysis," In: *Macromolecular Sequencing and Synthesis, Selected Methods and Applications*, Liss Inc. publ. New York pp. 127–149 (1988).
Gruss, H. and S. Dower, "Tumor Necrosis Factor Ligand Superfamily: Involvement in the Pathology of Malignant Lymphomas," *Blood* 85(12):3378–3404 (Jun. 1995).
Gruss, H. and S. Dower, "The TNF ligand superfamily and its relevance for human diseases," *Cytokines and Molecular Therapy* 1(2):75–105 (Jun. 1995).
Gruss, H. and F. Herrmann, "CD30 Ligand, a Member of the TNF Ligand Superfamily, with Growth and Activation Control for CD30+ Lymphoid and Lymphoma Cells," *Leukemia and Lymphoma* 20(5/6):397–409 (Feb. 1996).
Gruss, H. et al., "Structural and biological features of the TNF receptor and TNF ligand superfamilies: Interactive signals in the pathobiology of Hodgkins disease," *Annals of Oncology* 7(Suppl. 4):s19–s26 (1996).

(List continued on next page.)

Primary Examiner—David S. Romeo
(74) Attorney, Agent, or Firm—Sterne, Kessler, Goldstein and Fox P.L.L.C.

(57) ABSTRACT

The present invention relates to a novel member of the TNF-Ligand superfamily, Apoptosis Inducing Molecule II (AIM II). In particular, isolated nucleic acid molecules are provided encoding the human AIM II protein. AIM II polypeptides are also provided as are vectors, host cells and recombinant methods for producing the same. The invention further relates to screening methods for identifying agonists and antagonists of AIM II activity. Also provided are therapeutic methods for treating lymphadenopathy, autoimmune disease, graft versus host disease, and to inhibit neoplasia, such as tumor cell growth.

42 Claims, 38 Drawing Sheets

OTHER PUBLICATIONS

Lundwall, A., "Characterization of the gene for Prostate–specific antigen, a human glandular kallikrein," *Biochem. Biophys. Res. Comm.* 161(3):1151–1159 (1989).

Takahashi, T. et al., "Generalized Lymphoproliferative Disease in Mice, Caused by a Point Mutation in the Fas Ligand," *Cell* 76:969–976 (1994).

Takahashi, T. et al., "Human Fas ligand: gene structure, chromosomal location and species specificity," *International Immunology* 6(10):1567–1574 (1994).

Takeda, Y. et al., "Rapid acceleration of neutrophil apoptosis by tumor necrosis factor–α," *International Immunology* 5(6):691–694 (1993).

Tanaka, M. et al., "Expression of the functional soluble form of human Fas ligand in activated lymphocytes," *EMBO J.* 14(6):1129–1135 (Mar. 1995).

Genbank Report, Accession No. M27274, submitted by A. Lundwall. (Nov. 1989).

Aggarwal, B.B, and Natarajan, K., "Tumor necrosis factors: Developments during the last decade," *Eur. Cytokine Netw.* 7:93–124 (Apr.–Jun. 1996).

Gruss, H.–J., "Molecular, structural, and biological characteristics of the tumor necrosis factor ligand superfamily," *Int. J. Clin. Lab. Res.* 26:143–159 (Jan. 1996).

Harrop, J.A., "Herpesvirus Entry Mediator Ligand (HVEM–L), a Novel Ligand for HVEM/TR2, Stimulates Proliferation of T Cells and Inhibits HT29 Cell Growth," *J. Biol. Chem.* 273:27548–27556 (Oct. 1998).

Mauri, D.N. et al., "LIGHT, a New Member of the TNF Superfamily, and Lymphotoxin α Are Ligands for Herpesvirus Entry Mediator," *Immunity* 8:21–30 (Jan. 1998).

Tan, K.B., "Characterization of a novel TNF–like ligand and recently described TNF ligand and TNF receptor superfamily genes and their constitutive and inducible expression in hematopoietic and non–hematopoietic cells," *Gene* 204:35–46 (Dec. 1997).

Anderson, D. et al, "A homologue of the TNF receptor and its ligand enhance T–cell growth and dendritic–cell function," *Nature* 390:175–179 (Nov. 1997).

Brunner, T. et al., "Cell–autonomous Fas (CD95)/Fas–ligand interaction mediates activation–induced apoptosis in T–cell hybridomas,"*Nature* 373:441–444 (Feb. 1995).

Chen, C.–M. et al., "Direct Interaction of Hepatitis C Virus Core Protein with the Cellular Lymphotoxin–β Receptor Modulates the Signal Pathway of the Lymphotoxin–β Receptor," *J. Virol.* 71:9417–9426 (Dec. 1997).

Font, J. et al., "Elevated Soluble CD27 Levels in Serum of Patients with Systemic Lupus Erythematosus," *Clin. Immunol.* 81:239–243 (Dec. 1996).

Ju, S.–T. et al., "Fas(CD95)/FasL interactions required for programmed cell death after T–cell activation," *Nature* 373:444–448 (Feb. 1995).

Kallio, P. et al., "Soluble CD27 in thyroid disorders," *J. Lab Clin. Med.* 132:478–482 (Dec. 1998).

Kersten, M.J. et al., "Elevation of Cerebrospinal Fluid Soluble CD27 Levels in Patients With Meningeal Localization of Lymphoid Malignancies," *Blood* 87:1985–1989 (Mar. 1996).

Kwon, B.S. et al., "A newly Identified Member of the Tumor Necrosis Factor Receptor Superfamily with a Wide Tissue Distribution and Involvement in Lymphocyte Activation," *J. Biol. Chem.* 272:14272–14276 (May 1997).

Nagumo, H. et al., "CD27/CD70 Interaction Augments IgE Secretion by Promoting the Differentiation of Memory B Cells into Plasma Cells," *J. Immun.* 161:6496–6502 (Dec. 1998).

Pandanilam, B. et al., "Expression of CD27 and ischemia/reperfusion–induced expression of its ligand Siva in rat kidneys," *Kidney Int.* 54:1967–1975 (Dec. 1998).

Ranheim, E.A. et al., "Expression of CD27 and its Ligand, CD70, on Chronic Lymphocytic Leukemia B Cells," *Blood* 85:3556–3565 (Jun. 1995).

Rennert, P.D. et al., "Selective disruption of lymphotoxin ligands reveals a novel set of mucosal lymph nodes and unique effects on lymph node cellular organization," *Int. Immunol.* 9:1627–1639 (Nov. 1997).

Sigurdsson, T. et al., "Peridontal Regenerative Potential of Space–Providing Expanded Polytetrafluoroethylene Membranes and Recombinant Human Bone Morphogenetic Proteins," *J. Periodontol.* 66:511–521 (Jun. 1995).

Suda, T. et al., "Molecular Cloning and Expression of the Fas Ligand, a Novel Member of the Tumor Necrosis Factor Family," *Cell* 75:1169–1178 (Dec. 1993).

Swaak, A.J.G. et al., "Serum Levels of Soluble Forms of T–Cell Activation Antigens CD27 and CD25 in Systemic Lupus Erythematosus in Relation with Lymphocytes Count and Disease Course," *Clin. Rheumatol.* 14:293–300 (May 1995).

NCBI Entrez. GenBank Report, Accession No. T74524, Hillier et al. (Mar. 1995).

NCBI Entrez, GenBank Report, Accession No. H73550, Hillier et al. (Oct. 1995).

NCBI Entrez, GenBank Report, Accession No. N77915, Hillier et al. (Mar. 1996).

NCBI Entrez, GenBank Report, Accession No. AA570740, from NCI–CGAP (Sep. 1997).

NCBI Entrez, GenBank Report, Accession No. AA568204, from NCI–CGAP (Mar. 1999).

English translation of Japanese Patent Application No. 8–191204 (Document AL1).

English Translation of Japanese Patent Application No. 8–211695 (Document AM1).

English translation of Japanese Patent Application No. 9–019330 (Document AN1).

\* cited by examiner

```
                    10                      30                     50
    GAGGTTGAAGGACCCAGGCGTGTCAGCCCTGCTCCAGAGACCTTGGGCATGGAGGAGAGT
    ----------+---------+---------+---------+---------+---------+
                                                        M  E  E  S
              70                      90                    110
    GTCGTACGGCCCTCAGTGTTTGTGGTGGATGGACAGACCGACATCCCATTCACGAGGCTG
    ----------+---------+---------+---------+---------+---------+
     V  V  R  P  S  V  F  V  V  D  G  Q  T  D  I  P  F  T  R  L
              130                    150                    170
    GGACGAAGCCACCGGAGACAGTCGTGCAGTGTGGCCCGGGTGGGTCTGGGTCTCTTGCTG
    ----------+---------+---------+---------+---------+---------+
     G  R  S  H  R  R  Q  S  C  S  V  A  R  V  G  L  G  L  L  L
              190                    210                    230
    TTGCTGATGGGGGCTGGGCTGGCCGTCCAAGGCTGGTTCCTCCTGCAGCTGCACTGGCGT
    ----------+---------+---------+---------+---------+---------+
     L  L  M  G  A  G  L  A  V  Q  G  W  F  L  L  Q  L  H  W  R
              250                    270                    290
    CTAGGAGAGATGGTCACCCGCCTGCCTGACGGACCTGCAGGCTCCTGGGAGCAGCTGATA
    ----------+---------+---------+---------+---------+---------+
     L  G  E  M  V  T  R  L  P  D  G  P  A  G  S  W  E  Q  L  I
              310                    330                    350
    CAAGAGCGAAGGTCTCACGAGGTCAACCCAGCAGCGCATCTCACAGGGGCCAACTCCAGC
    ----------+---------+---------+---------+---------+---------+
     Q  E  R  R  S  H  E  V  N  P  A  A  H  L  T  G  A  N  S  S
              370                    390                    410
    TTGACCGGCAGCGGGGGGCCGCTGTTATGGGAGACTCAGCTGGGCCTGGCCTTCCTGAGG
    ----------+---------+---------+---------+---------+---------+
     L  T  G  S  G  G  P  L  L  W  E  T  Q  L  G  L  A  F  L  R
              430                    450                    470
    GGCCTCAGCTACCACGATGGGGCCCTTGTGGTCACCAAAGCTGGCTACTACTACATCTAC
    ----------+---------+---------+---------+---------+---------+
     G  L  S  Y  H  D  G  A  L  V  V  T  K  A  G  Y  Y  Y  I  Y
              490                    510                    530
    TCCAAGGTGCAGCTGGGCGGTGTGGGCTGCCCGCTGGGCCTGGCCAGCACCATCACCCAC
    ----------+---------+---------+---------+---------+---------+
     S  K  V  Q  L  G  G  V  G  C  P  L  G  L  A  S  T  I  T  H
              550                    570                    590
    GGCCTCTACAAGCGCACCCCGCTACCCCGAGGAGCTGGAGCTGTTGGTCAGCCAGCAG
    ----------+---------+---------+---------+---------+---------+
     G  L  Y  K  R  T  P  R  Y  P  E  E  L  E  L  L  V  S  Q  Q
              610                    630                    650
    TCACCCTGCGGACGGGCCACCAGCAGCTCCCGGGTCTGGTGGGACAGCAGCTTCCTGGGT
```

FIG.1A

```
---------+---------+---------+---------+---------+---------+
  S  P  C  G  R  A  T  S  S  S  R  V  W  W  D  S  S  F  L  G
        670                 690                 710
             .                   .                   .
GGTGTGGTACACCTGGAGGCTGGGGAGGAGGTGGTCGTCCGTGTGCTGGATGAACGCCTG
---------+---------+---------+---------+---------+---------+
  G  V  V  H  L  E  A  G  E  E  V  V  V  R  V  L  D  E  R  L
        730                 750                 770
             .                   .                   .
GTTCGACTGCGTGATGGTACCCGGTCTTACTTCGGGGCTTTCATGGTGTGAAGGAAGGAG
---------+---------+---------+---------+---------+---------+
  V  R  L  R  D  G  T  R  S  Y  F  G  A  F  M  V  *
        790                 810                 830
             .                   .                   .
CGTGGTGCATTGGACATGGGTCTGACACGTGGAGAACTCAGAGGGTGCCTCAGGGGAAAG
---------+---------+---------+---------+---------+---------+
        850                 870                 890
             .                   .                   .
AAAACTCACGAAGCAGAGGCTGGGCGTGGTGGCTCTCGCCTGTAATCCCAGCACTTTGGG
---------+---------+---------+---------+---------+---------+
        910                 930                 950
             .                   .                   .
AGGCCAAGGCAGGCGGATCACCTGAGGTCAGGAGTTCGAGACCAGCCTGGCTAACATGGC
---------+---------+---------+---------+---------+---------+
        970                 990                 1010
             .                   .                   .
AAAACCCCATCTCTACTAAAAATACAAAAATTAGCCGGACGTGGTGGTGCCTGCCTGTAA
---------+---------+---------+---------+---------+---------+
        1030                1050                1070
             .                   .                   .
TCCAGCTACTCAGGAGGCTGAGGCAGGATAATTTTGCTTAAACCCGGGAGGCGGAGGTTG
---------+---------+---------+---------+---------+---------+
        1090                1110                1130
             .                   .                   .
CAGTGAGCCGAGATCACACCACTGCACTCCAACCTGGGAAACGCAGTGAGACTGTGCCTC
---------+---------+---------+---------+---------+---------+
        1150
             .
AAAAAAAAAAAAAAAAAAAAAAAAAAAAA
---------+---------+---------
```

FIG.1B

```
                    10                      30
                    .                       .
          ATTCCCCGGGCCCGGGTGGGTCTGGGTCTCTTGCTGTTGCTGATG
          ---------+----------+----------+----------+-----
           I  P  R  A  R  V  G  L  G  L  L  L  L  L  M
             50                      70                      90
              .                       .                       .
          GGGGCCGGGCTGGCCGTCCAAGGCTGGTTCCTCCTGCAGCTGCAC
          ----+----------+----------+----------+----------+
           G  A  G  L  A  V  Q  G  W  F  L  L  Q  L  H
                                  110                   130
                                   .                     .
          TGGCGTCTAGGAGAGATGGTCACCCGCCTGCCTGACGGACCTGCA
          ---------+----------+----------+----------+-----
           W  R  L  G  E  M  V  T  R  L  P  D  G  P  A
                         150                    170
                           .                      .
          GGCTCCTGGGAGCAGCTGATACAAGAGCGAAGGTCTCACGAGGTC
          ----+----------+----------+----------+----------+
           G  S  W  E  Q  L  I  Q  E  R  R  S  H  E  V
                    190                     210
                     .                       .
          AACCCAGCAGCGCATCTCACAGGGGCCAACTCCAGCTTGACCGGC
          ---------+----------+----------+----------+-----
           N  P  A  A  H  L  T  G  A  N  S  S  L  T  G
             230                     250                     270
              .                       .                       .
          AGCGGGGGGCCGCTGTTATGGGAGACTCAGCTGGGCCTGGCCTTC
          ----+----------+----------+----------+----------+
           S  G  G  P  L  L  W  E  T  Q  L  G  L  A  F
                                  290                   310
                                   .                     .
          CTGAGGGGCCTCAGCTACCACGATGGGGCCCTTGTGGTCACCAAA
          ---------+----------+----------+----------+-----
           L  R  G  L  S  Y  H  D  G  A  L  V  V  T  K
                         330                    350
                           .                      .
          GCTGGCTACTACTACATCTACTCCAAGGTGCAGCTGGGCGGTGTG
          ----+----------+----------+----------+----------+
           A  G  Y  Y  Y  I  Y  S  K  V  Q  L  G  G  V
                    370                     390
                     .                       .
          GGCTGCCCGCTGGGCCTGGCCAGCACCATCACCCACGGCCTCTAC
          ---------+----------+----------+----------+-----
           G  C  P  L  G  L  A  S  T  I  T  H  G  L  Y
             410                     430                     450
              .                       .                       .
          AAGCGCACACCCCGCTACCCCGAGGAGCTGGAGCTGTTGGTCAGC
          ----+----------+----------+----------+----------+
           K  R  T  P  R  Y  P  E  E  L  E  L  L  V  S
                                  470                   490
```

FIG.1C

```
CAGCAGTCACCCTGCGGACGGGCCACCAGCAGCTCCCGGGTCTGG
---------+---------+---------+---------+-----
 Q  Q  S  P  C  G  R  A  T  S  S  S  R  V  W
          510                 530

TGGGACAGCAGCTTCCTGGGTGGTGTGGTACACCTGGAGGCTGGG
----+---------+---------+---------+---------+
 W  D  S  S  F  L  G  G  V  V  H  L  E  A  G
       550                 570

GAGGAGGTGGTCGTCCGTGTGCTGGATGAACGCCTGGTTCGACTG
---------+---------+---------+---------+-----
 E  E  V  V  V  R  V  L  D  E  R  L  V  R  L
    590                 610                630

CGTGATGGTACCCGGTCTTACTTCGGGGCTTTCATGGTGTGAAGG
----+---------+---------+---------+---------+
 R  D  G  T  R  S  Y  F  G  A  F  M  V  *
                   650                 670

AAGGAGCGTGGTGCATTGGACATGGGTCTGACACGTGGAGAACTC
---------+---------+---------+---------+-----
              690                 710

AGAGGGTGCCTCAGGGGAAAGAAAACTCACGAAGCAGAGGCTGGG
----+---------+---------+---------+---------+
     730                 750

CGTGGTGGCTCTCGCCTGTAATCCCAGCACTTTGGGAGGCCAAGG
---------+---------+---------+---------+-----
     770                 790                810

CAGGCGGATCACCTGAGGTCAGGAGTTCGAGACCAGCCTGGCTAA
----+---------+---------+---------+---------+
                   830                 850

CATGGCAAAACCCCATCTCTACTAAAAATACAAAAATTAGCCGGA
---------+---------+---------+---------+-----
              870                 890

CGTGGTGGTGCCTGCCTGTAATCCAGCTACTCAGGAGGCTGAGGC
----+---------+---------+---------+---------+
     910                 930

AGGATAATTTGCTTAAACCCGGGAGGCGGAGGTTGCAGTGAGCC
---------+---------+---------+---------+-----
     950                 970                990

GAGATCACACCACTGCACTCCAACCTGGGAAACGCAGTGAGACTG
----+---------+---------+---------+---------+
                   1010

TGCCTCAAAAAAAACAAAAAAAAAAAA
---------+---------+--------
```

```
        Q T A R Q H P S M E L A K S T L K P A A H L I G D P S S - - Majority
                  |              |              |
                 190            200            210
 77 A G S W E Q L I Q E R R S H E V N P A A H L T G A N S S L T   Aim-2.aa
181 S C S N C K K S L E C T K L C L P Q I E N V K G T E D S G I   huTNFalpha.prot
 46 Q T A R Q H P K M H L A H S T L K P A A H L I G D P S K - -   huTNFbeta.prot
 46 Q T A R Q H P K M H L A H S T L K P A A H L I G D P S K - -   huLymphotoxin.prot
128 E K Q I G H P S P P P E K K E L R K V A H L T G K S N S - -   huFasLigand.prot

- - Q N - P L L - - - - - - - - - - - - - - - - - W E    Majority
                  |              |              |
                 220            230            240
107 G S G G P L L - - - - - - - - - - - - - - - - - - - - W E    Aim-2.aa
211 T V L L L P L V I F F G L C L L S L L F I G L M Y R Y Q R W K huTNFalpha.prot
 74 - - Q N - S L L - - - - - - - - - - - - - - - - - - - W R    huTNFbeta.prot
 74 - - Q N - S L L - - - - - - - - - - - - - - - - - - - W R    huLymphotoxin.prot
156 - - R S M P L E - - - - - - - - - - - - - - - - - - - W E    huFasLigand.prot A N L G R A F - - - - - - - - - - - - - - - - - L Q D G  Majority
                  |              |              |
                 250            260            270
116 T Q L G L A F - - - - - - - - - - - - - - - - - - - - G      Aim-2.aa
241 S K L Y S I V C G K S T P E K E G E L E G T T T T K P L A P N huTNFalpha.prot
 81 A N T D R A F - - - - - - - - - - - - - - - - - - - L Q D G  huTNFbeta.prot
 81 A N T D R A F - - - - - - - - - - - - - - - - - - - L Q D G  huLymphotoxin.prot
164 D T Y G I V L - - - - - - - - - - - - - - - - - - - L - S G  huFasLigand.prot
```

FIG. 2C

```
      F S L S N G S L V V P T S G I Y F V V S Q V V F S G K A Y S  Majority
                   |                   |                   |
                  280                 290                 300
126  L S Y H D G A L V V T K A G Y Y Y I Y S K V Q L G G V G C P  Aim-2.aa
271  P S F S P T P G F T P T L G F S P V P S S T F T S S S T Y T  huTNFalph.prot
 92  F S L S N N S L L V P T S G I Y F V S Q V V F S G K A Y S    huTNFbeta.prot
 92  F S L S N N S L L V P T S G I Y F V S Q V V F S G K A Y S    hulymphotoxin.prot
174  V K Y K G G L V I N E T G L Y F V Y S K V Y F R G Q S C N    huFasLigand.prot P G A X S S P L Y L A H E V Q L R S S Q Y P F H V P L L S S  Majority
                   |                   |                   |
                  310                 320                 330
156  L G L A S T - - I T H G L Y K R T P R Y P E E L E L L V S    Aim-2.aa
301  P G D C P N F A A P R R E V - - A P P Y Q G A D P I L A T    huTNFalph.prot
122  P K A P S P L Y L A H E V Q L F S S Q Y P F H V P L L S S    huTNFbeta.prot
122  P K A T S P L Y L A H E V Q L F S S Q Y P F H V P L L S S    hulymphotoxin.prot
204  - - - - N L P L S H K V Y M R N S K Y P Q D L V M M E G      huFasLigand.prot Q K M V Y - - - P G L Q E P W L D S S Y L G A A F Q L T Q G  Majority
                   |                   |                   |
                  340                 350                 360
183  Q Q S P C C G R A T S S S R V W W D S S F L G G V V H L E A G  Aim-2.aa
328  A - L A S D P I P N P L Q K W E D S A H K P Q S L D T D D P  huTNFalph.prot
152  Q K M V Y - - - P G L Q E P W L H S M Y H G A A F Q L T Q G  huTNFbeta.prot
152  Q K M V Y - - - P G L Q E P W L H S M Y H G A A F Q L T Q G  hulymphotoxin.prot
228  K M M S Y - - - C T T G Q M W A R S S Y L G A V F N L T S A  huFasLigand.prot
```

FIG. 2D

```
         DQLSVHVDGIPLLVLSEST-VFF--------- Majority
                   |         |         |
                  370       380       390

213 EEVVVRVLDERLVRLRDGTRSYF--------- Aim-2.aa
357 ATLYAVVENVPPLRWKEFVRLGLSDHEID huTNFalpha.prot
179 DQLSTHTDGIPHLVLSPST-VFF--------- huTNFbeta.prot
179 DQLSTHTDGIPHLVLSPST-VFF--------- huLymphotoxin.prot
255 DHLYVNSELSLVNFEESQ-TFF--------- huFasLigand.prot ---------GAFA-L--------------- Majority
                   |         |         |
                  400       410       420

236 ---------GAFMV--------------- Aim-2.aa
387 RLELQNGRCLREAQYSMLATWRRRTPRREA huTNFalpha.prot
201 ---------GAFA-L--------------- huTNFbeta.prot
201 ---------GAFA-L--------------- huLymphotoxin.prot
277 ---------GLYK-L--------------- huFasLigand.prot
```

```
                        - - - - - - - - - - - - - - - - - - - - - - - - - - - Majority
                    430                   440                   450
241    - - - - - - - - - - - - - - - - - - - - - - - - - - -              Aim-2.aa
417    T L E L L G R V L R D M D L L G C L E D I E E E A L C G P A A      huTNFalpha.prot
205    - - - - - - - - - - - - - - - - - - - - - - - - - - -              huTNFbeta.prot
205    - - - - - - - - - - - - - - - - - - - - - - - - - - -              huLymphotoxin.prot
281    - - - - - - - - - - - - - - - - - - - - - - - - - - -              huFasLigand.prot Majority 241    - - - - - - - - - -                                                 Aim-2.aa
447    L P P A P S L L R                                                   huTNFalpha.prot
205    - - - - - - - - - -                                                 huTNFbeta.prot
205    - - - - - - - - - -                                                 huLymphotoxin.prot
281    - - - - - - - - - -                                                 huFasLigand.prot
```

DECORATION 'DECORATION #1': SHADE (WITH SOLID BRIGHT COLBALT) RESIDUES THAT MATCH Aim-2.aa EXACTLY.

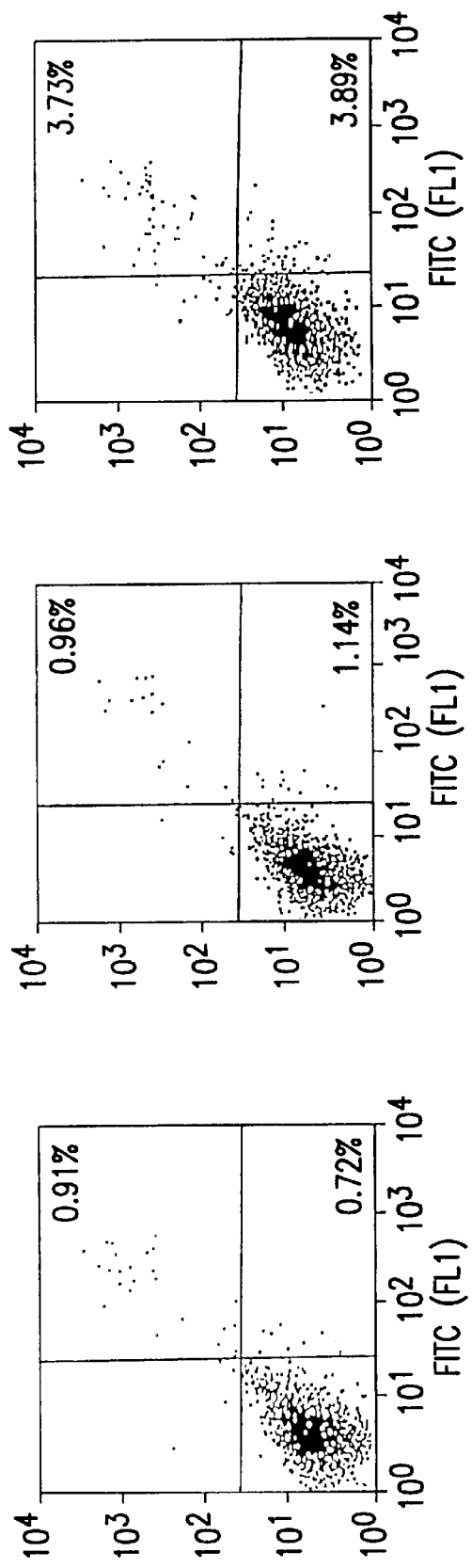

| CELL LINES | LTγ EXPRESSION[1] | LTβR EXPRESSION[1] | TR2 EXPRESSION[1] | GROWTH INHIBITION BY LTγ[2] |
|---|---|---|---|---|
| MDA-MB-231 | − | ++ | ++ | ++ |
| MCF-7 | − | ++ | ++ | ++ |
| HT-29 | − | +++ | ++ | ++++ |
| MC-3 | − | ++ | − | − |
| U93T | − | − | + | − |
| MCF-10A | ++ | + | ± | − |
| PBMC[3] | + | − | + | − |
| T-CELLS | + | − | ++ | − |
| TIL 1200 | + | − | + | − |
| Jurkat | − | − | + | − |

1. EXPRESSION OF LTγ WAS DETERMINED BY RT-PCR ASSAY; EXPRESSION OF LTβR AND TR2 WAS DETERMINED BY FACS ANALYSIS;
2. CYTOTOXICITY WAS CARRIED OUT WITH 50ng/ml OF LTγ IN THE PRESENCE OF 10 μ/ml OF IFNγ. +: 30% INHIBITION, ++:50% INHIBITION, +++;80% INHIBITION, −: LESS THAN 10% INHIBITION.
3. LTγ WAS FOUND ONLY IN ACTIVATED PBMC NOT IN RESTING PBMC.

FIG.8L

```
                                        -35      OPERATOR 1
1  AAGCTTAAAAAACTGCAAAAAATAGT|TTGACT|TGTGAGCGGATAACAAT

-10                        OPERATOR 2
50 |TAAGAT|GTACCCA|ATTGTGAGCGGATAACAAT|TTCACACATTAA

S/D
94 A|GAGGAG|AAATTA CATATG
```

FIG.11

```
 1  M G L S T V P D L L L P L V L L E L L V G I Y P S G V I G L   huTNFalpha.prot
 1  M - - T P P E R L F L P R V - - - - - - - - - - - - - - - -   huTNFbeta.prot
 1  M - - T P P E R L F L P R V - - - - - - - - - - - - - - - -   huLymphotoxin.prot
 1  M - - Q Q P F N Y P Y P Q I Y W V D S S A S S P W A P P G T   huFasLigand.prot
 1  - - - - - - P R A - - - - - - - - - - - - - - - - - - - - -   huAIM-2.prot
              10                  20                  30

31  V P H L G D R E K R D S V C P Q G K Y I H P Q N N S I C C T   huTNFalpha.prot
13  - - - - - - - - - - - - - - - - - - C G T T L H - - - - - -   huTNFbeta.prot
13  - - - - - - - - - - - - - - - - - - C G T T L H - - - - - -   huLymphotoxin.prot
29  V L P - - - - - - - - - - - - - - - C P T S V P R R P G Q R R huFasLigand.prot
 5  - - - - - - - - - - - - - - - - - - - - - - - - - - - - - -   huAIM-2.prot
              40                  50                  60

61  K C H K G T Y L Y N D C P G P G Q D T D C R E C E S G S F T   huTNFalpha.prot
19  - - - - - - - - - - - - - - - - - - - - - - - - - - - - - -   huTNFbeta.prot
19  - - - - - - - - - - - - - - - - - - - - - - - - - - - - - -   huLymphotoxin.prot
45  - - - - - - - - P P P P P P P P L P P P P P P P - - - - - -   huFasLigand.prot
 5  - - - - - - - - - - - - - - - - - - - - - - - - - - - - - -   huAIM-2.prot
              70                  80                  90
```

```
                190               200               210
181  S C S N C K K S L E C T K L C L P Q I E N V K G T E D S G T   huTNFalpha.prot
 46  Q T A R Q H P K M H L A H S T L K P A A H L I G D P S K - -   huTNFbeta.prot
 46  Q T A R Q H P K M H L A H S T L K P A A H L I G D P S K - -   huLymphotoxin.prot
128  E K Q I G H P S P P P E K K E L R K V A H L T G K S N S - -   huFasLigand.prot
 45  A G S W E Q L I Q E R R S H E V N P A A H L T G A N S S L T   huAIM-2.prot 220               230               240
211  T V L L I P L V I F F G L C L L S L L F I G L M Y R Y Q R W K   huTNFalpha.prot
  4  - Q N - S L L - - - - - - - - - - - - - - - - - - - - - W R   huTNFbeta.prot
 74  - Q N - S L L - - - - - - - - - - - - - - - - - - - - - W R   huLymphotoxin.prot
156  - R S M P L E - - - - - - - - - - - - - - - - - - - - - W E   huFasLigand.prot
 75  G S G G P L L - - - - - - - - - - - - - - - - - - - - - W E   huAIM-2.prot 250               260               270
241  S K L Y S I V C G K S T P E K E G E L E G T T T T K P L A P N   huTNFalpha.prot
 81  A N T D R A F - - - - - - - - - - - - - - - - - - - L Q D G   huTNFbeta.prot
 81  A N T D R A F - - - - - - - - - - - - - - - - - - - L Q D G   huLymphotoxin.prot
164  D I Y G I V L - - - - - - - - - - - - - - - - - - - L - S G   huFasLigand.prot
 84  T Q L G L A F - - - - - - - - - - - - - - - - - - - L R - G   huAIM-2.prot
```

```
         360              370              380
357 A T L Y A V V E N V P P L R W K E F V R R L G L S D H E I D  huTNFalpha.prot
179 D Q L S T H T D G I P H L V L S P S T - V F F - - - - - - -  huTNFbeta.prot
179 D Q L S T H T D G I P H L V L S P S T - V F F - - - - - - -  huLymphotoxin.prot
255 D H L Y V N V S E L S L V N F E E S Q - T F F - - - - - - -  huFasLigand.prot
181 E E V V V R V L D E R L V R L R D G T R S Y F - - - - - - -  huAIM-2.prot 390              400              410
387 R L E L Q N G R C L R E A Q Y S M L A T W R R R T P R R E A  huTNFalpha.prot
201 - - - - - - - - - - - - - G A F A - L - - - - - - - - - - -  huTNFbeta.prot
201 - - - - - - - - - - - - - G A F A - L - - - - - - - - - - -  huLymphotoxin.prot
277 - - - - - - - - - - - - - G L Y K - L - - - - - - - - - - -  huFasLigand.prot
204 - - - - - - - - - - - - - G A F M V - - - - - - - - - - - -  huAIM-2.prot 420              430              440
417 T L E L L G R V L R D M D L L G C L E D I E E A L C G P A A  huTNFalpha.prot
205 - - - - - - - - - - - - - - - - - - - - - - - - - - - - - -  huTNFbeta.prot
205 - - - - - - - - - - - - - - - - - - - - - - - - - - - - - -  huLymphotoxin.prot
281 - - - - - - - - - - - - - - - - - - - - - - - - - - - - - -  huFasLigand.prot
209 - - - - - - - - - - - - - - - - - - - - - - - - - - - - - -  huAIM-2.prot
```

FIG.14F huTNFalpha.prot
huTNFbeta.prot
huLymphotoxin.prot
huFasLigand.prot
huAIM-2.prot

447 L P P A P S L L R
     450
205
205
281
209

SEQUENCE LISTING

```
<160> NUMBER OF SEQ ID NOS: 55

<210> SEQ ID NO 1
<211> LENGTH: 1169
<212> TYPE: DNA
<213> ORGANISM: Homo sapiens
<220> FEATURE:
<221> NAME/KEY: CDS
<222> LOCATION: (49)..(768)
```

```
<400> SEQUENCE: 1
gaggttgaag gacccaggcg tgtcagccct gctccagaga ccttgggc atg gag gag      57
                                                     Met Glu Glu
                                                      1 agt gtc gta cgg ccc tca gtg ttt gtg gtg gat gga cag acc gac atc     105
Ser Val Val Arg Pro Ser Val Phe Val Val Asp Gly Gln Thr Asp Ile
      5                  10                  15 cca ttc acg agg ctg gga cga agc cac cgg aga cag tcg tgc agt gtg     153
Pro Phe Thr Arg Leu Gly Arg Ser His Arg Arg Gln Ser Cys Ser Val
 20                  25                  30                  35 gcc cgg gtg ggt ctg ggt ctc ttg ctg ttg ctg atg ggg gct ggg ctg     201
Ala Arg Val Gly Leu Gly Leu Leu Leu Leu Leu Met Gly Ala Gly Leu
                 40                  45                  50 gcc gtc caa ggc tgg ttc ctc ctg cag ctg cac tgg cgt cta gga gag     249
Ala Val Gln Gly Trp Phe Leu Leu Gln Leu His Trp Arg Leu Gly Glu
             55                  60                  65 atg gtc acc cgc ctg cct gac gga cct gca ggc tcc tgg gag cag ctg     297
Met Val Thr Arg Leu Pro Asp Gly Pro Ala Gly Ser Trp Glu Gln Leu
         70                  75                  80 ata caa gag cga agg tct cac gag gtc aac cca gca gcg cat ctc aca     345
Ile Gln Glu Arg Arg Ser His Glu Val Asn Pro Ala Ala His Leu Thr
     85                  90                  95 ggg gcc aac tcc agc ttg acc ggc agc ggg ggg ccg ctg tta tgg gag     393
Gly Ala Asn Ser Ser Leu Thr Gly Ser Gly Gly Pro Leu Leu Trp Glu
100                 105                 110                 115 act cag ctg ggc ctg gcc ttc ctg agg ggc ctc agc tac cac gat ggg     441
Thr Gln Leu Gly Leu Ala Phe Leu Arg Gly Leu Ser Tyr His Asp Gly
                120                 125                 130 gcc ctt gtg gtc acc aaa gct ggc tac tac tac atc tac tcc aag gtg     489
Ala Leu Val Val Thr Lys Ala Gly Tyr Tyr Tyr Ile Tyr Ser Lys Val
            135                 140                 145 cag ctg ggc ggt gtg ggc tgc ccg ctg ggc ctg gcc agc acc atc acc     537
Gln Leu Gly Gly Val Gly Cys Pro Leu Gly Leu Ala Ser Thr Ile Thr
        150                 155                 160 cac ggc ctc tac aag cgc aca ccc cgc tac ccc gag gag ctg gag ctg     585
His Gly Leu Tyr Lys Arg Thr Pro Arg Tyr Pro Glu Glu Leu Glu Leu
    165                 170                 175 ttg gtc agc cag cag tca ccc tgc gga cgg gcc acc agc agc tcc cgg     633
Leu Val Ser Gln Gln Ser Pro Cys Gly Arg Ala Thr Ser Ser Ser Arg
180                 185                 190                 195 gtc tgg tgg gac agc agc ttc ctg ggt ggt gtg gta cac ctg gag gct     681
Val Trp Trp Asp Ser Ser Phe Leu Gly Gly Val Val His Leu Glu Ala
                200                 205                 210 ggg gag gag gtg gtc gtc cgt gtg ctg gat gaa cgc ctg gtt cga ctg     729
Gly Glu Glu Val Val Val Arg Val Leu Asp Glu Arg Leu Val Arg Leu
            215                 220                 225 cgt gat ggt acc cgg tct tac ttc ggg gct ttc atg gtg tgaaggaagg     778
Arg Asp Gly Thr Arg Ser Tyr Phe Gly Ala Phe Met Val
        230                 235                 240 agcgtggtgc attggacatg gtctgacac gtggagaact cagagggtgc ctcaggggaa    838
agaaaactca cgaagcagag gctgggcgtg gtggctctcg cctgtaatcc cagcactttg   898
ggaggccaag gcaggcggat cacctgaggt caggagttcg agaccagcct ggctaacatg   958
gcaaaacccc atctctacta aaaatacaaa aattagccgg acgtggtggt gcctgcctgt  1018
aatccagcta ctcaggaggc tgaggcagga aatttttgct taaacccggg aggcggaggt  1078
tgcagtgagc cgagatcaca ccactgcact ccaacctggg aaacgcagtg agactgtgcc  1138
tcaaaaaaaa aaaaaaaaaa aaaaaaaaa a                                   1169
```

<210> SEQ ID NO 2
<211> LENGTH: 240
<212> TYPE: PRT
<213> ORGANISM: Homo sapiens

<400> SEQUENCE: 2

```
Met Glu Glu Ser Val Val Arg Pro Ser Val Phe Val Val Asp Gly Gln
 1               5                  10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

<210> SEQ ID NO 3
<211> LENGTH: 455
<212> TYPE: PRT
<213> ORGANISM: Homo sapiens

<400> SEQUENCE: 3

```
Met Gly Leu Ser Thr Val Pro Asp Leu Leu Leu Pro Leu Val Leu Leu
 1               5                  10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95
```

```
Arg His Cys Leu Ser Cys Ser Lys Cys Arg Lys Glu Met Gly Gln Val
            100                 105                 110
Glu Ile Ser Ser Cys Thr Val Asp Arg Asp Thr Val Cys Gly Cys Arg
            115                 120                 125
Lys Asn Gln Tyr Arg His Tyr Trp Ser Glu Asn Leu Phe Gln Cys Phe
        130                 135                 140
Asn Cys Ser Leu Cys Leu Asn Gly Thr Val His Leu Ser Cys Gln Glu
145                 150                 155                 160
Lys Gln Asn Thr Val Cys Thr Cys His Ala Gly Phe Phe Leu Arg Glu
                165                 170                 175
Asn Glu Cys Val Ser Cys Ser Asn Cys Lys Lys Ser Leu Glu Cys Thr
            180                 185                 190
Lys Leu Cys Leu Pro Gln Ile Glu Asn Val Lys Gly Thr Glu Asp Ser
        195                 200                 205
Gly Thr Thr Val Leu Leu Pro Leu Val Ile Phe Phe Gly Leu Cys Leu
    210                 215                 220
Leu Ser Leu Leu Phe Ile Gly Leu Met Tyr Arg Tyr Gln Arg Trp Lys
225                 230                 235                 240
Ser Lys Leu Tyr Ser Ile Val Cys Gly Lys Ser Thr Pro Glu Lys Glu
                245                 250                 255
Gly Glu Leu Glu Gly Thr Thr Thr Lys Pro Leu Ala Pro Asn Pro Ser
            260                 265                 270
Phe Ser Pro Thr Pro Gly Phe Thr Pro Thr Leu Gly Phe Ser Pro Val
        275                 280                 285
Pro Ser Ser Thr Phe Thr Ser Ser Ser Thr Tyr Thr Pro Gly Asp Cys
    290                 295                 300
Pro Asn Phe Ala Ala Pro Arg Arg Glu Val Ala Pro Pro Tyr Gln Gly
305                 310                 315                 320
Ala Asp Pro Ile Leu Ala Thr Ala Leu Ala Ser Asp Pro Ile Pro Asn
                325                 330                 335
Pro Leu Gln Lys Trp Glu Asp Ser Ala His Lys Pro Gln Ser Leu Asp
            340                 345                 350
Thr Asp Asp Pro Ala Thr Leu Tyr Ala Val Val Glu Asn Val Pro Pro
        355                 360                 365
Leu Arg Trp Lys Glu Phe Val Arg Arg Leu Gly Leu Ser Asp His Glu
    370                 375                 380
Ile Asp Arg Leu Glu Leu Gln Asn Gly Arg Cys Leu Arg Glu Ala Gln
385                 390                 395                 400
Tyr Ser Met Leu Ala Thr Trp Arg Arg Arg Thr Pro Arg Arg Glu Ala
                405                 410                 415
Thr Leu Glu Leu Leu Gly Arg Val Leu Arg Asp Met Asp Leu Leu Gly
            420                 425                 430
Cys Leu Glu Asp Ile Glu Glu Ala Leu Cys Gly Pro Ala Ala Leu Pro
        435                 440                 445
Pro Ala Pro Ser Leu Leu Arg
    450                 455

<210> SEQ ID NO 4
<211> LENGTH: 205
<212> TYPE: PRT
<213> ORGANISM: Homo sapiens

<400> SEQUENCE: 4

Met Thr Pro Pro Glu Arg Leu Phe Leu Pro Arg Val Cys Gly Thr Thr
```

```
           1              5              10             15
     Leu His Leu Leu Leu Gly Leu Leu Leu Val Leu Leu Pro Gly Ala
                     20             25             30

Gln Gly Leu Pro Gly Val Gly Leu Thr Pro Ser Ala Ala Gln Thr Ala
                 35                 40                 45

Arg Gln His Pro Lys Met His Leu Ala His Ser Thr Leu Lys Pro Ala
             50                 55                 60

Ala His Leu Ile Gly Asp Pro Ser Lys Gln Asn Ser Leu Leu Trp Arg
     65                 70                 75                 80

Ala Asn Thr Asp Arg Ala Phe Leu Gln Asp Gly Phe Ser Leu Ser Asn
                     85                 90                 95

Asn Ser Leu Leu Val Pro Thr Ser Gly Ile Tyr Phe Val Tyr Ser Gln
                     100                105                110

Val Val Phe Ser Gly Lys Ala Tyr Ser Pro Lys Ala Pro Ser Ser Pro
                     115                120                125

Leu Tyr Leu Ala His Glu Val Gln Leu Phe Ser Ser Gln Tyr Pro Phe
                     130                135                140

His Val Pro Leu Leu Ser Ser Gln Lys Met Val Tyr Pro Gly Leu Gln
     145                150                155                160

Glu Pro Trp Leu His Ser Met Tyr His Gly Ala Ala Phe Gln Leu Thr
                     165                170                175

Gln Gly Asp Gln Leu Ser Thr His Thr Asp Gly Ile Pro His Leu Val
                     180                185                190

Leu Ser Pro Ser Thr Val Phe Phe Gly Ala Phe Ala Leu
                     195                200                205
```

<210> SEQ ID NO 5
<211> LENGTH: 205
<212> TYPE: PRT
<213> ORGANISM: Homo sapiens

<400> SEQUENCE: 5

```
     Met Thr Pro Pro Glu Arg Leu Phe Leu Pro Arg Val Cys Gly Thr Thr
     1               5                  10                 15

Leu His Leu Leu Leu Gly Leu Leu Leu Val Leu Leu Pro Gly Ala
                     20             25             30

Gln Gly Leu Pro Gly Val Gly Leu Thr Pro Ser Ala Ala Gln Thr Ala
                 35                 40                 45

Arg Gln His Pro Lys Met His Leu Ala His Ser Thr Leu Lys Pro Ala
             50                 55                 60

Ala His Leu Ile Gly Asp Pro Ser Lys Gln Asn Ser Leu Leu Trp Arg
     65                 70                 75                 80

Ala Asn Thr Asp Arg Ala Phe Leu Gln Asp Gly Phe Ser Leu Ser Asn
                     85                 90                 95

Asn Ser Leu Leu Val Pro Thr Ser Gly Ile Tyr Phe Val Tyr Ser Gln
                     100                105                110

Val Val Phe Ser Gly Lys Ala Tyr Ser Pro Lys Ala Thr Ser Ser Pro
                     115                120                125

Leu Tyr Leu Ala His Glu Val Gln Leu Phe Ser Ser Gln Tyr Pro Phe
                     130                135                140

His Val Pro Leu Leu Ser Ser Gln Lys Met Val Tyr Pro Gly Leu Gln
     145                150                155                160

Glu Pro Trp Leu His Ser Met Tyr His Gly Ala Ala Phe Gln Leu Thr
                     165                170                175
```

```
Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
        195                 200                 205

<210> SEQ ID NO 6
<211> LENGTH: 281
<212> TYPE: PRT
<213> ORGANISM: Homo sapiens

<400> SEQUENCE: 6

Met Gln Gln Pro Phe Asn Tyr Pro Tyr Pro Gln Ile Tyr Trp Val Asp
  1               5                  10                  15

Ser Ser Ala Ser Ser Pro Trp Ala Pro Pro Gly Thr Val Leu Pro Cys
             20                  25                  30

Pro Thr Ser Val Pro Arg Arg Pro Gly Gln Arg Arg Pro Pro Pro Pro
         35                  40                  45

Pro Pro Pro Pro Pro Leu Pro Pro Pro Pro Pro Pro Pro Pro Leu Pro
     50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Leu Ala
                100                 105                 110

Glu Leu Arg Glu Ser Thr Ser Gln Met His Thr Ala Ser Ser Leu Glu
            115                 120                 125

Lys Gln Ile Gly His Pro Ser Pro Pro Pro Glu Lys Lys Glu Leu Arg
130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
        210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 7
gcgggatccg gagagatggt cacc                                      24
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 8
cgcaagcttc cttcacacca tgaaagc                              27

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 9
gaccggatcc atggaggaga gtgtcgtacg gc                        32

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 10
cgcaagcttc cttcacacca tgaaagc                              27

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 11
gctccaggat ccgccatcat ggaggagagt gtcgtacggc                40

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 12
gacgcggtac cgtccaatgc accacgctcc ttccttc                   37

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 13
gagctcggat ccgccatcat ggaggagagt gtcgtacggc                40

<210> SEQ ID NO 14
<211> LENGTH: 71
<212> TYPE: DNA
<213> ORGANISM: Artificial Sequence
<220> FEATURE:

<223> OTHER INFORMATION: Description of Artificial Sequence: primer

<400> SEQUENCE: 14
gatgttctag aaagcgtagt ctgggacgtc gtatgggtac accatgaaag ccccgaagta  60
agaccgggta c  71

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 15
gctccaggat ccgccatcat ggaggagagt gtcgtacggc  40

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 16
gacgcggtac cgtccaatgc accacgctcc ttccttc  37

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 17
gacgcccatg gaggaggaga gtgtcgtacg gc  32

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 18
gaccggatcc caccatgaaa gccccgaagt aag  33

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 19
cgcaagcttc cttcacacca tgaaagc  27

<210> SEQ ID NO 20
<211> LENGTH: 503
<212> TYPE: DNA
<213> ORGANISM: Homo sapiens

<400> SEQUENCE: 20
aattccccgg gaccggntgg gtctgggtct cttgctgttg ctgatggggg ccgggctggn  60
cgtncaaggc tggttcctcc tgcagctgca ctgggntcta ggngagatgg tcacccgcct  120

```
gcctgaacgg acctgcaggc tcctgggagc agctgataca agagcgangt ctcacgaggt    180
caacccagca gcgcatctca caggggccaa ctccagcttg accggcagcg ggggccgct     240 tttatgggag actcagctgg gnctggnctt cctgaggggt ntcanctacc acgatgggn     300 cccttntggt naccaaagtt gggtactact nacaacttat tncaagnggc agttgggcgg    360
tgttgggttg cccnctgggg ctngggnaaa aannanaaan naagggcttt taaaaagggg    420
aaaaccggtt aacncgaggn agntggagtt tttggttnaa ncatgattaa acctgggnag    480
ggncanaaaa aatncnggtg ntt                                           503

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 21
gggggatcca tggtcacccg cctgcc                                         26

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 22
gggaagcttc accatgaaag ccccg                                          25

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 23
gggccatgga tggtcacccg cctgcc                                         26

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 24
gggccatggg ccaactccag cttgacc                                        27

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 25
gggggatccc gcagctgcac tggcgtctag g                                   31

<210> SEQ ID NO 26
<211> LENGTH: 25
<212> TYPE: DNA
```

```
<213> ORGANISM: Artificial Sequence
<220> FEATURE:
<223> OTHER INFORMATION: Description of Artificial Sequence: primer

<400> SEQUENCE: 26
gggtctagac accatgaaag ccccg                                            25

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 27
cgcggatccc tcctgggagc agctgatac                                        29

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 28
gggggatcct gacaccatga aagccccg                                         28

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 29
cgcggatcct cacaccatga aagc                                             24

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 30
gggggatccc accatgaaag ccccg                                            25

<210> SEQ ID NO 31
<211> LENGTH: 733
<212> TYPE: DNA
<213> ORGANISM: Homo sapiens

<400> SEQUENCE: 31
gggatccgga gcccaaatct tctgacaaaa ctcacacatg cccaccgtgc ccagcacctg      60
aattcgaggg tgcaccgtca gtcttcctct tccccccaaa acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agcccgccca acccccatcg     360
agaaaaccat ctccaaagcc aaagggcagc ccgagaacca caggtgtac accctgcccc     420 catcccggga tgagctgacc aagaaccagg tcagcctgac ctgcctggtc aaaggcttct     480
```

```
atccaagcga catcgccgtg gagtgggaga gcaatgggca gccggagaac aactacaaga      540
ccacgcctcc cgtgctggac tccgacggct ccttcttcct ctacagcaag ctcaccgtgg      600
acaagagcag gtggcagcag gggaacgtct tctcatgctc cgtgatgcat gaggctctgc      660
acaaccacta cacgcagaag agcctctccc tgtctccggg taaatgagtg cgacggccgc      720
gactctagag gat                                                        733

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 32
ggggtcgacg ccatcatgga ggagagtgtc gtacgg                                36

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 33
ggggcggccg cgccttcaca ccatgaaagc cccg                                  34

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 34
ggggcggccg cgccatcatg gaggagagtg tcgtacgg                              38

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 35
ggggtcgacg ccttcacacc atgaaagccc cg                                    32

<210> SEQ ID NO 36
<211> LENGTH: 93
<212> TYPE: DNA
<213> ORGANISM: Artificial Sequence
<220> FEATURE:
<223> OTHER INFORMATION: Description of Artificial Sequence: primer

<400> SEQUENCE: 36
ggggcggccg cgccatcatg aaggtctccg tggctgccct ctcctgcctc atgcttgtta      60
ctgcccttgg atcgcaggca gctgcactgg cgt                                   93

<210> SEQ ID NO 37
<211> LENGTH: 28
<212> TYPE: DNA
<213> ORGANISM: Artificial Sequence
<220> FEATURE:
```

<223> OTHER INFORMATION: Description of Artificial Sequence: primer

<400> SEQUENCE: 37

```
ggggtcgact cacaccatga aagccccg                                             28
```

<210> SEQ ID NO 38
<211> LENGTH: 1017
<212> TYPE: DNA
<213> ORGANISM: Homo sapiens
<220> FEATURE:
<221> NAME/KEY: CDS
<222> LOCATION: (1)..(624)

<400> SEQUENCE: 38

```
att ccc cgg gcc cgg gtg ggt ctg ggt ctc ttg ctg ttg ctg atg ggg           48
Ile Pro Arg Ala Arg Val Gly Leu Gly Leu Leu Leu Leu Leu Met Gly
 1               5                  10                  15 gcc ggg ctg gcc gtc caa ggc tgg ttc ctc ctg cag ctg cac tgg cgt           96
Ala Gly Leu Ala Val Gln Gly Trp Phe Leu Leu Gln Leu His Trp Arg
             20                  25                  30 cta gga gag atg gtc acc cgc ctg cct gac gga cct gca ggc tcc tgg          144
Leu Gly Glu Met Val Thr Arg Leu Pro Asp Gly Pro Ala Gly Ser Trp
         35                  40                  45 gag cag ctg ata caa gag cga agg tct cac gag gtc aac cca gca gcg          192
Glu Gln Leu Ile Gln Glu Arg Arg Ser His Glu Val Asn Pro Ala Ala
     50                  55                  60 cat ctc aca ggg gcc aac tcc agc ttg acc ggc agc ggg ggg ccg ctg          240
His Leu Thr Gly Ala Asn Ser Ser Leu Thr Gly Ser Gly Gly Pro Leu
 65                  70                  75                  80 tta tgg gag act cag ctg ggc ctg gcc ttc ctg agg ggc ctc agc tac          288
Leu Trp Glu Thr Gln Leu Gly Leu Ala Phe Leu Arg Gly Leu Ser Tyr
                 85                  90                  95 cac gat ggg gcc ctt gtg gtc acc aaa gct ggc tac tac tac atc tac          336
His Asp Gly Ala Leu Val Val Thr Lys Ala Gly Tyr Tyr Tyr Ile Tyr
            100                 105                 110 tcc aag gtg cag ctg ggc ggt gtg ggc tgc ccg ctg ggc ctg gcc agc          384
Ser Lys Val Gln Leu Gly Gly Val Gly Cys Pro Leu Gly Leu Ala Ser
        115                 120                 125 acc atc acc cac ggc ctc tac aag cgc aca ccc cgc tac ccc gag gag          432
Thr Ile Thr His Gly Leu Tyr Lys Arg Thr Pro Arg Tyr Pro Glu Glu
    130                 135                 140 ctg gag ctg ttg gtc agc cag cag tca ccc tgc gga cgg gcc acc agc          480
Leu Glu Leu Leu Val Ser Gln Gln Ser Pro Cys Gly Arg Ala Thr Ser
145                 150                 155                 160 agc tcc cgg gtc tgg tgg gac agc agc ttc ctg ggt ggt gtg gta cac          528
Ser Ser Arg Val Trp Trp Asp Ser Ser Phe Leu Gly Gly Val Val His
                165                 170                 175 ctg gag gct ggg gag gag gtg gtc gtc cgt gtg ctg gat gaa cgc ctg          576
Leu Glu Ala Gly Glu Glu Val Val Val Arg Val Leu Asp Glu Arg Leu
            180                 185                 190 gtt cga ctg cgt gat ggt acc cgg tct tac ttc ggg gct ttc atg gtg          624
Val Arg Leu Arg Asp Gly Thr Arg Ser Tyr Phe Gly Ala Phe Met Val
        195                 200                 205 tgaaggaagg agcgtggtgc attggacatg ggtctgacac gtggagaact cagagggtgc        684
ctcaggggaa agaaaactca cgaagcagag gctgggcgtg gtggctctcg cctgtaatcc        744
cagcactttg ggaggccaag gcaggcggat cacctgaggt caggagttcg agaccagcct        804
ggctaacatg gcaaaccccc atctctacta aaaatacaaa aattagccgg acgtggtggt        864
gcctgcctgt aatccagcta ctcaggaggc tgaggcagga taattttgct taaacccggg        924
```

```
aggcggaggt tgcagtgagc cgagatcaca ccactgcact ccaacctggg aaacgcagtg    984
agactgtgcc tcaaaaaaaa caaaaaaaaa aaa                                 1017
```

<210> SEQ ID NO 39
<211> LENGTH: 208
<212> TYPE: PRT
<213> ORGANISM: Homo sapiens

<400> SEQUENCE: 39

```
Ile Pro Arg Ala Arg Val Gly Leu Gly Leu Leu Leu Leu Met Gly
 1               5                  10                  15

Ala Gly Leu Ala Val Gln Gly Trp Phe Leu Gln Leu His Trp Arg
                20                  25                  30

Leu Gly Glu Met Val Thr Arg Leu Pro Asp Gly Pro Ala Gly Ser Trp
            35                  40                  45

Glu Gln Leu Ile Gln Glu Arg Arg Ser His Glu Val Asn Pro Ala Ala
        50                  55                  60

His Leu Thr Gly Ala Asn Ser Ser Leu Thr Gly Ser Gly Pro Leu
 65                 70                  75                  80

Leu Trp Glu Thr Gln Leu Gly Leu Ala Phe Leu Arg Gly Leu Ser Tyr
                85                  90                  95

His Asp Gly Ala Leu Val Val Thr Lys Ala Gly Tyr Tyr Tyr Ile Tyr
            100                 105                 110

Ser Lys Val Gln Leu Gly Gly Val Gly Cys Pro Leu Gly Leu Ala Ser
        115                 120                 125

Thr Ile Thr His Gly Leu Tyr Lys Arg Thr Pro Arg Tyr Pro Glu Glu
    130                 135                 140

Leu Glu Leu Leu Val Ser Gln Gln Ser Pro Cys Gly Arg Ala Thr Ser
145                 150                 155                 160

Ser Ser Arg Val Trp Trp Asp Ser Ser Phe Leu Gly Gly Val Val His
                165                 170                 175

Leu Glu Ala Gly Glu Glu Val Val Val Arg Val Leu Asp Glu Arg Leu
            180                 185                 190

Val Arg Leu Arg Asp Gly Thr Arg Ser Tyr Phe Gly Ala Phe Met Val
        195                 200                 205
```

<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 40

```
gacagtggat ccgccaccat ggtcacccgc ctgcctgacg gac                      43
```

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 41

```
cgcggatcct gggagcagct gatac                                          25
```

<210> SEQ ID NO 42
<211> LENGTH: 25
<212> TYPE: DNA

```
<213> ORGANISM: Artificial Sequence
<220> FEATURE:
<223> OTHER INFORMATION: Description of Artificial Sequence: primer

<400> SEQUENCE: 42
cgccatatga cccgcctgcc tgacg                                    25

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 43
cgccatatga gctgggagca gctgatac                                 28

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 44
cgccatatga gcagcttgac cggcagcg                                 28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 45
cgcggtacct tacaccatga aagccccg                                 28

<210> SEQ ID NO 46
<211> LENGTH: 11
<212> TYPE: PRT
<213> ORGANISM: Homo sapiens

<400> SEQUENCE: 46

Gly Leu Tyr Leu Ile Tyr Ser Gln Val Leu Phe
 1               5                  10

<210> SEQ ID NO 47
<211> LENGTH: 11
<212> TYPE: PRT
<213> ORGANISM: Homo sapiens

<400> SEQUENCE: 47

Gly Tyr Tyr Tyr Ile Tyr Ser Lys Val Gln Leu
 1               5                  10

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 48
cgggatccat gctcctgcct tgggccac                                 28
```

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 49
gcggatcctg ggggcagtgg ctctaatgg  29

<210> SEQ ID NO 50
<211> LENGTH: 3974
<212> TYPE: DNA
<213> ORGANISM: Artificial Sequence
<220> FEATURE:
<223> OTHER INFORMATION: Description of Artificial Sequence: vector

<400> SEQUENCE: 50

| | | |
|---|---|---|
| ggtacctaag tgagtagggc gtccgatcga cggacgcctt ttttttgaat tcgtaatcat | 60 |
| ggtcatagct gtttcctgtg tgaaattgtt atccgctcac aattccacac aacatacgag | 120 |
| ccggaagcat aaagtgtaaa gcctggggtg cctaatgagt gagctaactc acattaattg | 180 |
| cgttgcgctc actgcccgct ttccagtcgg gaaacctgtc gtgccagctg cattaatgaa | 240 |
| tcggccaacg cgcggggaga ggcggtttgc gtattgggcg ctcttccgct tcctcgctca | 300 |
| ctgactcgct gcgctcggtc gttcggctgc ggcgagcggt atcagctcac tcaaaggcgg | 360 |
| taatacggtt atccacagaa tcaggggata acgcaggaaa gaacatgtga gcaaaaggcc | 420 |
| agcaaaaggc caggaaccgt aaaaaggccg cgttgctggc gtttttccat aggctccgcc | 480 |
| cccctgacga gcatcacaaa aatcgacgct caagtcagag gtggcgaaac ccgacaggac | 540 |
| tataaagata ccaggcgttt ccccctggaa gctccctcgt gcgctctcct gttccgaccc | 600 |
| tgccgcttac cggatacctg tccgcctttc tcccttcggg aagcgtggcg ctttctcata | 660 |
| gctcacgctg taggtatctc agttcggtgt aggtcgttcg ctccaagctg ggctgtgtgc | 720 |
| acgaaccccc cgttcagccc gaccgctgcg ccttatccgg taactatcgt cttgagtcca | 780 |
| acccggtaag acacgactta tcgccactgg cagcagccac tggtaacagg attagcagag | 840 |
| cgaggtatgt aggcggtgct acagagttct tgaagtggtg gcctaactac ggctacacta | 900 |
| gaagaacagt atttggtatc tgcgctctgc tgaagccagt taccttcgga aaaagagttg | 960 |
| gtagctcttg atccggcaaa caaaccaccg ctggtagcgg tggttttttt gtttgcaagc | 1020 |
| agcagattac gcgcagaaaa aaaggatctc aagaagatcc tttgatcttt tctacggggt | 1080 |
| ctgacgctca gtggaacgaa aactcacgtt aagggatttt ggtcatgaga ttatcgtcga | 1140 |
| caattcgcgc gcgaaggcga agcggcatgc atttacgttg acaccatcga atggtgcaaa | 1200 |
| acctttcgcg gtatggcatg atagcgcccg gaagagagtc aattcagggt ggtgaatgtg | 1260 |
| aaaccagtaa cgttatacga tgtcgcagag tatgccggtg tctcttatca gaccgtttcc | 1320 |
| cgcgtggtga accaggccag ccacgtttct gcgaaaacgc gggaaaaagt ggaagcggcg | 1380 |
| atggcggagc tgaattacat tcccaaccgc gtggcacaac aactggcggg caaacagtcg | 1440 |
| ttgctgattg gcgttgccac ctccagtctg gccctgcacg cgccgtcgca aattgtcgcg | 1500 |
| gcgattaaat ctcgcgccga tcaactgggt gccagcgtgg tggtgtcgat ggtagaacga | 1560 |
| agcggcgtcg aagcctgtaa agcggcggtg cacaatcttc tcgcgcaacg cgtcagtggg | 1620 |
| ctgatcatta actatccgct ggatgaccag gatgccattg ctgtggaagc tgcctgcact | 1680 |
| aatgttccgg cgttatttct tgatgtctct gaccagacac ccatcaacag tattattttc | 1740 |

-continued

```
tcccatgaag acggtacgcg actgggcgtg gagcatctgg tcgcattggg tcaccagcaa    1800
atcgcgctgt tagcgggccc attaagttct gtctcggcgc gtctgcgtct ggctggctgg    1860
cataaatatc tcactcgcaa tcaaattcag ccgatagcgg aacgggaagg cgactggagt    1920
gccatgtccg gttttcaaca aaccatgcaa atgctgaatg agggcatcgt tcccactgcg    1980
atgctggttg ccaacgatca gatggcgctg gcgcaatgc cgccattac cgagtccggg     2040
ctgcgcgttg gtgcggatat ctcggtagtg ggatacgacg ataccgaaga cagctcatgt    2100
tatatcccgc cgttaaccac catcaaacag gattttcgcc tgctggggca aaccagcgtg    2160
gaccgcttgc tgcaactctc tcagggccag gcggtgaagg gcaatcagct gttgcccgtc    2220
tcactggtga aagaaaaac cacccctggcg cccaatacgc aaaccgcctc tccccgcgcg    2280
ttggccgatt cattaatgca gctggcacga caggtttccc gactggaaag cgggcagtga    2340
gcgcaacgca attaatgtaa gttagcgcga attgtcgacc aaagcggcca tcgtgcctcc    2400
ccactcctgc agttcggggg catggatgcg cggatagccg ctgctggttt cctggatgcc    2460
gacggatttg cactgccggt agaactccgc gaggtcgtcc agcctcaggc agcagctgaa    2520
ccaactcgcg aggggatcga gcccggggtg ggcgaagaac tccagcatga gatccccgcg    2580
ctggaggatc atccagccgg cgtcccggaa aacgattccg aagcccaacc tttcatagaa    2640
ggcggcggtg gaatcgaaat ctcgtgatgg caggttgggc gtcgcttggt cggtcatttc    2700
gaacccagaa gtcccgctca gaagaactcg tcaagaaggc gatagaaggc gatgcgctgc    2760
gaatcgggag cggcgatacc gtaaagcacg aggaagcggt cagcccattc gccgccaagc    2820
tcttcagcaa tatcacgggt agccaacgct atgtcctgat agcggtccgc cacacccagc    2880
cggccacagt cgatgaatcc agaaaagcgg ccatttccca ccatgatatt cggcaagcag    2940
gcatcgccat gggtcacgac gagatcctcg ccgtcgggca tgcgcgcctt gagcctggcg    3000
aacagttcgc ctgcgcgag cccctgatgc tcttcgtcca gatcatcctg atcgacaaga    3060
ccggcttcca tccgagtacg tgctcgctcg atgcgatgtt tcgcttggtg gtcgaatggg    3120
caggtagccg gatcaagcgt atgcagccgc cgcattgcat cagccatgat ggatactttc    3180
tcggcaggag caaggtgaga tgacaggaga tcctgccccg gcacttcgcc caatagcagc    3240
cagtcccttc ccgcttcagt gacaacgtcg agcacagctg cgcaaggaac gcccgtcgtg    3300
gccagccacg atagccgcgc tgcctcgtcc tgcagttcat tcagggcacc ggacaggtcg    3360
gtcttgacaa aaagaaccgg gcgccccctgc gctgacagcc ggaacacggc ggcatcagag    3420
cagccgattg tctgttgtgc ccagtcatag ccgaatagcc tctccaccca agcggccgga    3480
gaacctgcgt gcaatccatc ttgttcaatc atgcgaaacg atcctcatcc tgtctcttga    3540
tcagatcttg atcccctgcg ccatcagatc cttggcggca agaaagccat ccagtttact    3600
ttgcagggct tcccaacctt accagagggc gccccagctg gcaattccgg ttcgcttgct    3660
gtccataaaa ccgcccagtc tagctatcgc catgtaagcc cactgcaagc tacctgctttt   3720
ctctttgcgc ttgcgtttc ccttgtccag atagcccagt agctgacatt catccgggt      3780
cagcaccgtt tctgcggact ggctttctac gtgttccgct tcctttagca gcccttgcgc    3840
cctgagtgct tgcggcagcg tgaagcttaa aaaactgcaa aaaatagttt gacttgtgag    3900
cggataacaa ttaagatgta cccaattgtg agcggataac aatttcacac attaaagagg    3960
agaaattaca tatg                                                       3974
```

<210> SEQ ID NO 51
<211> LENGTH: 112

```
<212> TYPE: DNA
<213> ORGANISM: Artificial Sequence
<220> FEATURE:
<223> OTHER INFORMATION: Description of Artificial Sequence: Regulatory
      Sequence

<400> SEQUENCE: 51
aagcttaaaa aactgcaaaa aatagtttga cttgtgagcg gataacaatt aagatgtacc     60
caattgtgag cggataacaa tttcacacat taaagaggag aaattacata tg           112

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: DNA Primer

<400> SEQUENCE: 52
cgcggatccc ggagagatgg tcacc                                           25

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 53
cgctctagac cttcacacca tgaaagc                                         27

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 54
cgcggatcca tgggtctggg tctcttg                                         27

<210> SEQ ID NO 55
<211> LENGTH: 51
<212> TYPE: DNA
<213> ORGANISM: Artificial Sequence
<220> FEATURE:
<223> OTHER INFORMATION: Description of Artificial Sequence: DNA Primer

<400> SEQUENCE: 55
cgctctagat caagcgtagt ctgggacgtc gtatggcacc atgaaagccc c              51
```

APOPTOSIS INDUCING MOLECULE II

The present application is a Continuation-in-Part of Application Ser. No. 09/003,886 filed on Jan. 7, 1998, now abandoned which is herein incorporated by reference; said Ser. No. 09/003,886 is a Continuation-in-Part of application Ser. No. 08/822,953 filed on Mar. 21, 1997, now abandoned which is herein incorporated by reference; said Ser. No. 08/822,953 claims benefit to the filing date of provisional applications 60/013,923, filed Mar. 22, 1996 and 60/030,157, filed Oct. 31, 1996 each of which is also incorporated herein by reference.

BACKGROUND OF THE INVENTION

1. Field of the Invention

The present invention relates to a novel member of the TNF-Ligand superfamily. More specifically, isolated nucleic acid molecules are provided encoding a human Apoptosis Inducing Molecule II (AIM II). AIM II polypeptides are also provided, as are vectors, host cells and recombinant methods for producing the same. The invention further relates to screening methods for identifying agonists and antagonists of AIM II activity. Also provided are therapeutic methods for treating lymphadenopathy, autoimmune disease, graft versus host disease, and to inhibit neoplasia, such as tumor cell growth.

2. Related Art

Human tumor necrosis factors a (TNF-α) and β (TNF-β, or lymphotoxin) are related members of a broad class of polypeptide mediators, which includes the interferons, interleukins and growth factors, collectively called cytokines (Beutler, B. and Cerami, A., *Annu. Ret,. Immunol.*, 7:625–655 (1989)).

Tumor necrosis factor (TNF-α and TNF-β) was originally discovered as a result of its anti-tumor activity, however, now it is recognized as a pleiotropic cytokine capable of numerous biological activities including apoptosis of some transformed cell lines, mediation of cell activation and proliferation and also as playing important roles in immune regulation and inflammation.

To date, known members of the TNF-ligand superfamily include TNF-α, TNF-β(lymphotoxin-α), LT-β, OX40L, Fas ligand, CD30L, CD27L, CD40L and 4-IBBL. The ligands of the TNF ligand superfamily are acidic, TNF-like molecules with approximately 20% sequence homology in the extracellular domains (range, 12%–36%) and exist mainly as membrane-bound forms with the biologically active form being a trimeric/multimeric complex. Soluble forms of the TNF ligand superfamily have only been identified so far for TNF, LTα, and Fas ligand (for a general review, see Gruss, H. and Dower, S. K., *Blood*, 85(12):3378–3404 (1995)), which is hereby incorporated by reference in its entirety.

These proteins are involved in regulation of cell proliferation, activation, and differentiation, including control of cell survival or death by apoptosis or cytotoxicity (Armitage, R. J., *Curr. Opin. Immunol.* 6:407 (1994) and Smith, C.A., *Cell* 75:959 (1994)).

Mammalian development is dependent on both the proliferation and differentiation of cells as well as programmed cell death which occurs through apoptosis (Walker, et al., *Methods Achiev. Exp. Pathol.* 13:18 (1988). Apoptosis plays a critical role in the destruction of immune thymocytes that recognize self antigens. Failure of this normal elimination process may play a role in autoimmune diseases (Gammon et al., *Immunology Today* 12:193 (1991)).

Itoh et al. (*Cell* 66:233 (1991)) described a cell surface antigen, Fas/CD95 that mediates apoptosis and is involved in clonal deletion of T-cells. Fas is expressed in activated T-cells, B-cells, neutrophils and in thymus, liver, heart and lung and ovary in adult mice (Watanabe-Fukunaga et al., *J. Immunolo.* 148:1274 (1992)) in addition to activated T-cells, B-cells, neutorophils. In experiments where a monoclonal Ab to Fas is cross-linked to Fas, apoptosis is induced (Yonehara et al., *J. Exp. Med.* 169:1747 (1989); Trauth et al., *Science* 245:301 (1989)). In addition, there is an example where binding of a monoclonal Ab to Fas may stimulate T-cells under certain conditions (Alderson et al., *J. Exp. Med.* 178:2231 (1993)).

Fas antigen is a cell surface protein of relative MW of 45 Kd. Both human and murine genes for Fas have been cloned by Watanabe-Fukunaga et al., (*J. Immunol.* 148:1274 (1992)) and Itoh et al. (*Cell* 66:233 (1991)). The proteins encoded by these genes are both transmembrane proteins with structural homology to the Nerve Growth Factor/Tumor Necrosis Factor receptor superfamily, which includes two TNF receptors, the low affinity Nerve Growth Factor receptor and the $LT_\beta$ receptor CD40, CD27, CD30, and OX40.

Recently the Fas ligand has been described (Suda et al., *Cell* 75:1169 (1993)). The amino acid sequence indicates that Fas ligand is a type II transmembrane protein belonging to the TNF family. Fas ligand is expressed in splenocytes and thymocytes. The purified Fas ligand has a MW of 40 kd.

Recently, it has been demonstrated that Fas/Fas ligand interactions are required for apoptosis following the activation of T-cells (Ju et al., *Nature* 373:444 (1995); Brunner et al., *Nature* 373:441 (1995)). Activation of T-cells induces both proteins on the cell surface. Subsequent interaction between the ligand and receptor results in apoptosis of the cells. This supports the possible regulatory role for apoptosis induced by Fas/Fas ligand interaction during normal immune responses.

The polypeptide of the present invention has been identified as a novel member of the TNF ligand super-family based on structural and biological similarities.

Clearly, there is a need for factors that regulate activation, and differentiation of normal and abnormal cells. There is a need, therefore, for identification and characterization of such factors that modulate activation and differentiation of cells, both normally and in disease states. In particular, there is a need to isolate and characterize additional Fas ligands that control apoptosis for the treatment of autoimmune disease, graft versus host disease, rheumatoid arthritis and lymphadenopathy.

SUMMARY OF THE INVENTION

The present invention provides isolated nucleic acid molecules comprising a polynucleotide encoding the AIM II polypeptide having the amino acid sequence shown in FIGS. 1A and B (SEQ ID NO:2) or the amino acid sequence encoded by the cDNA clone deposited in a bacterial host as ATCC Deposit Number 97689 on Aug. 22, 1996. The present invention also provides isolated nucleic acid molecules comprising a polynucleotide encoding the AIM II polypeptide having the amino acid sequence shown in FIGS. 1C and D (SEQ ID NO:40) or the amino acid sequence encoded by the cDNA clone deposited in a bacterial host as ATCC Deposit Number 97483 on Mar. 15, 1996.

The present invention also relates to recombinant vectors, which include the isolated nucleic acid molecules of the present invention, and to host cells containing the recombinant vectors, as well as to methods of making such vectors and host cells and for using them for production of AIM II polypeptides or peptides by recombinant techniques.

The invention further provides an isolated AIM II polypeptide having an amino acid sequence encoded by a polynucleotide described herein.

As used herein the term "AIM II" polypeptide includes membrane-bound proteins (comprising a cytoplasmic domain, a transmembrane domain, and an extracellular domain) as well as truncated proteins that retain the AIM II polypeptide activity. In one embodiment, soluble AIM II polypeptides comprise all or part of the extracellular domain of an AIM II protein, but lack the transmsmbrane region that would cause retention of the polypeptide on a cell membrane. Soluble AIM II may also include part of the transmembrane region or part of the cytoplasmic domain or other sequences, provided that the soluble AIM II protein is capable of being secreted. A heterologous signal peptide can be fused to the N-terminus of the soluble AIM II polypeptide such that the soluble AIM II polypeptide is secreted upon expression.

The invention also provides for AIM II polypeptides, particularly human AIM-II polypeptides, which may be employed to treat lymphadenopathy, rheumatoid arthritis, autoimmune disease, graft versus host disease, which may be used to stimulate peripheral tolerance, destroy some transformed cell lines, mediate cell activation and proliferation and are functionally linked as primary mediators of immune regulation and inflammatory response.

The invention further provides compositions comprising an AIM II polynucleotide or an AIM II polypeptide for administration to cells in vitro, to cells ex vivo and to cells in vivo, or to a multicellular organism. In certain particularly preferred embodiments of this aspect of the invention, the compositions comprise an AIM II polynucleotide for expression of an AIM II polypeptide in a host organism for treatment of disease. Particularly preferred in this regard is expression in a human patient for treatment of a dysfunction associated with aberrant endogenous activity of an AIM II.

The present invention also provides a screening method for identifying compounds capable of enhancing or inhibiting a cellular response induced by AIM II, which involves contacting cells which express AIM II with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a screening assay for AIM II agonists and antagonists is provided. The antagonists may be employed to prevent septic shock, inflammation, cerebral malaria, activation of the HIV virus, graft-host rejection, bone resorption, and cachexia (wasting or malnutrition).

An additional aspect of the invention is related to a method for treating an individual in need of an increased level of AIM II activity in the body comprising administering to such an indivdual a composition comprising a therapeutically effective amount of an isolated AIM II polypeptide of the invention or an agonist thereof.

A still further aspect of the invention is related to a method for treating an individual in need of a decreased level of AIM II activity in the body comprising, administering to such an individual a composition comprising a therapeutically effective amount of an AIM II antagonist.

BRIEF DESCRIPTION OF THE FIGURES

FIGS. 1A and B show the nucleotide (SEQ ID NO:1) and deduced amino acid (SEQ ID NO:2) sequences of AIM II. The protein has a deduced molecular weight of about 26.4 kDa. The predicted Transmembrane Domain of the AIM II protein is underlined.

FIGS. 1C and D show the nucleotide (SEQ ID NO:38) and deduced amino acid (SEQ ID NO:39) sequences of a partial AIM II cDNA that was also obtained.

FIGS. 2A–F show the regions of similarity between the amino acid sequences of the AIM II protein (SEQ ID NO:2) and human TNF-α(SEQ ID NO:3), human TNF-β (SEQ ID NO:4), human lymphotoxin (SEQ ID NO:5) and human Fas Ligand (SEQ ID NO:6).

FIGS. 5A–C show increased Apoptotic cells in MDA-MB-231/AIM II (FIG. 5C) in 0.5% serum compared with that of the MDA-MB-231/WT (FIG. 5A) or MDA-MB-231/Neo (FIG. 5B) cells with Annexin-V FACS analysis as described in Example 5 Material and Methods.

FIGS. 8A–M Cell surface expression of the LTβR or TR2 by the FACS analyses using LTβR (FIGS. 8A–D) or TR2

(FIGS. 8E–H) mAb. MDA-MB-231 (FIGS. 8A and E)), HT-29 (8B and F), MC-3 (8C and G), U93T (8D and H). FACS binding analyses of soluble AIM II protein alone (FIG. 8I) and blocking of a soluble AIM II protein binding by preincubation with the LTβR-Fc fusion protein (FIG. 8J) or TR2-Fc fusion protein (FIG. 8K) in MDA-MB-231 cells. FIG. 8L summarizes the surface expression of LTβR and TR2 in various cell lines. (FIG. 8M) Effects of LTβR-Fc or TR2-Fc fusion protein to block the sAIM II-mediated cytotoxicity in HT-29 cells. Cells were plated into 96-well plates and sAIM II (10 ng/ml) was added in the presence of 5 U/ml of IFNγ with various amounts of sLTβR-Fc (open circle with LTβR-Fc alone, filled circle LTβR-Fc, and IFNγ) or TR2-Fc fusion protein (open triangle with TR-2Fc alone, filled triangle TR2-Fc with sLTγ and IFNγ). Cells were incubated for five days and the viability of cells was determined by XTT assays.

FIG. 11 shows the nucleotide sequence of the regulatory elements of the pHE promoter (SEQ ID NO:51). The two lac operator sequences, the Shine-Delgarno sequence (S/D), and the terminal HindIII and NdeI restriction sites (italicized) are indicated.

FIGS. 14A–F show shows an alignment of the amino acid sequence of the AIM-II polypeptide shown in SEQ ID NO:39 to the amino acid sequences of human TNFα (SEQ ID NO:3), human TNFβ (SEQ ID NO:4), human lymphotoxin (SEQ ID NO:5), and human Fas Ligand (SEQ ID NO:6) by the Clustal Method with PAM250 Weight Residue Table.

DETAILED DESCRIPTION

Figure 2A:
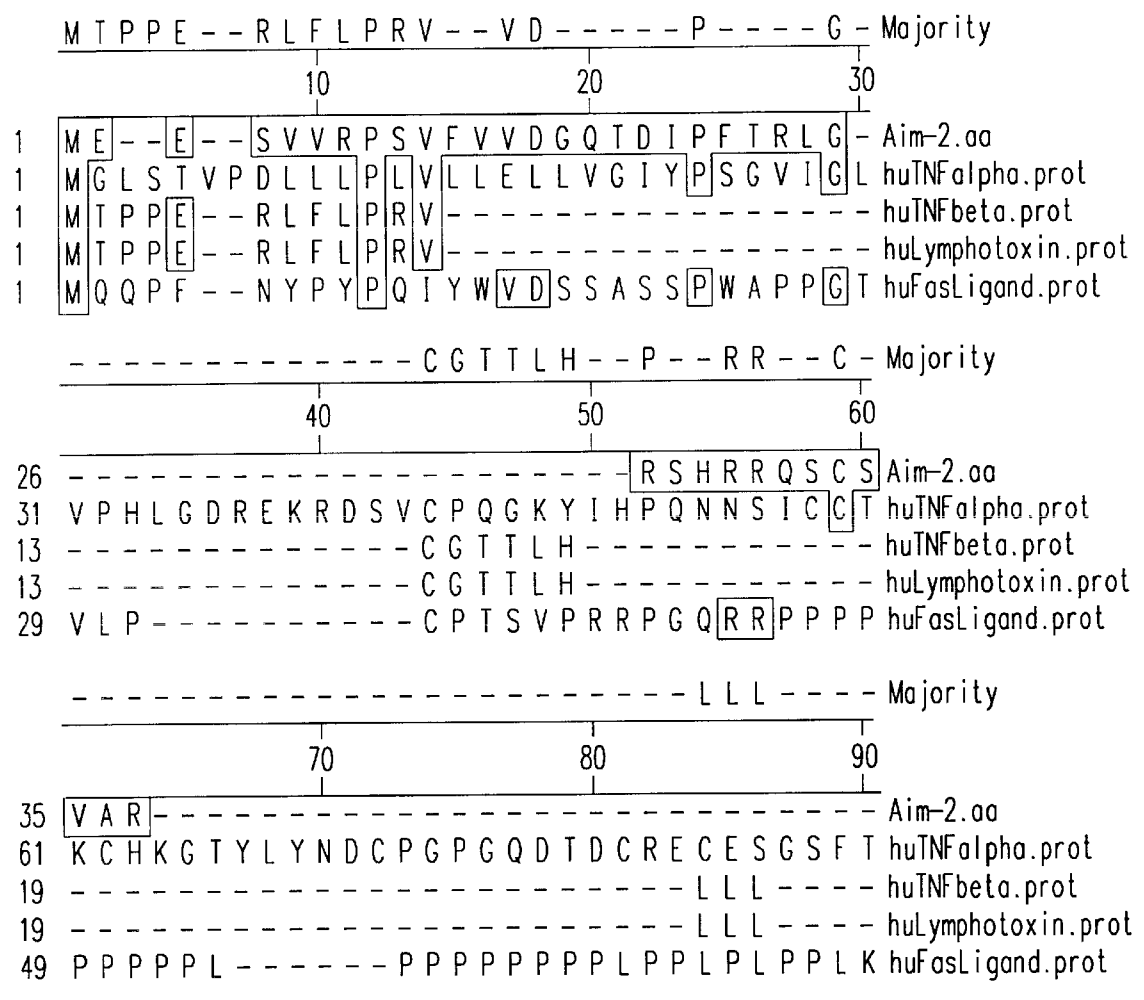
Figure 2B:
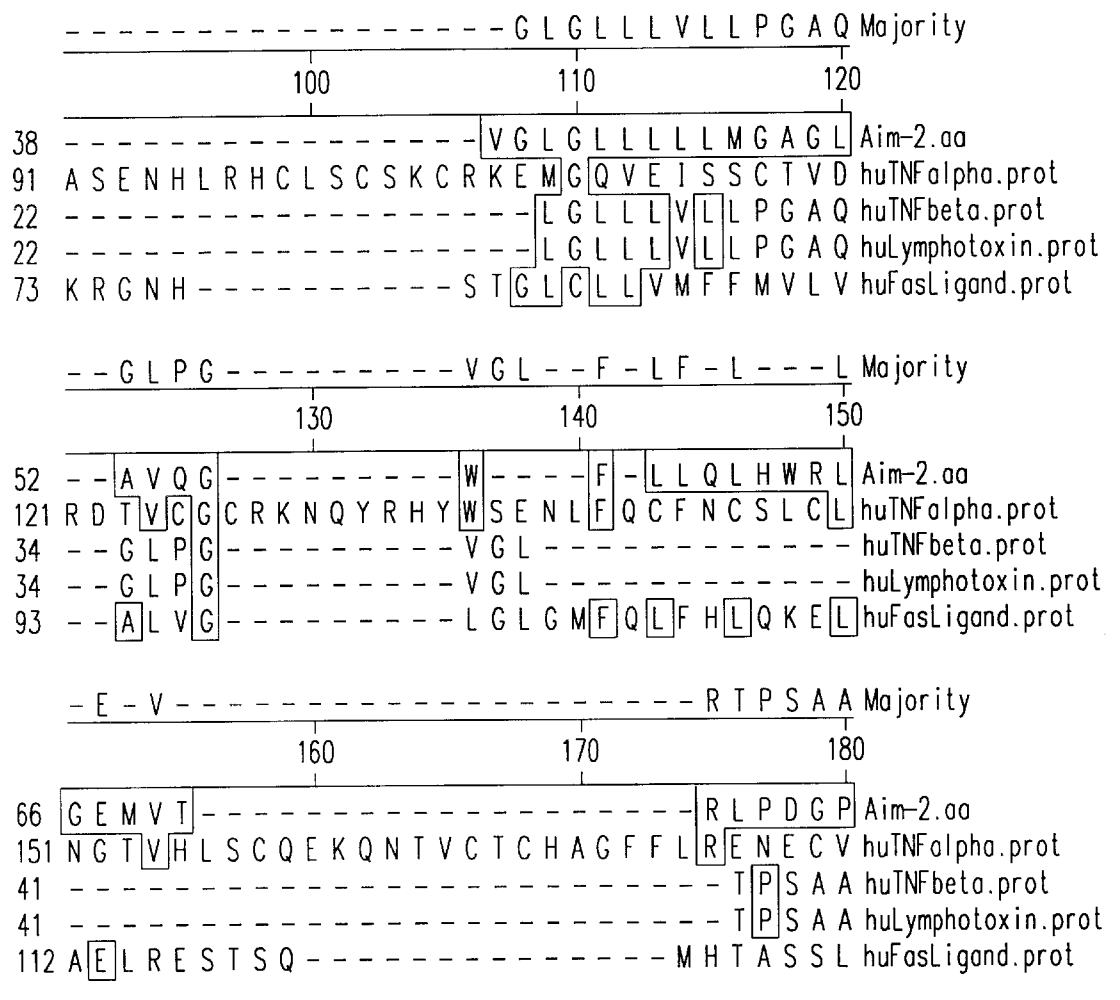
Figure 3A:
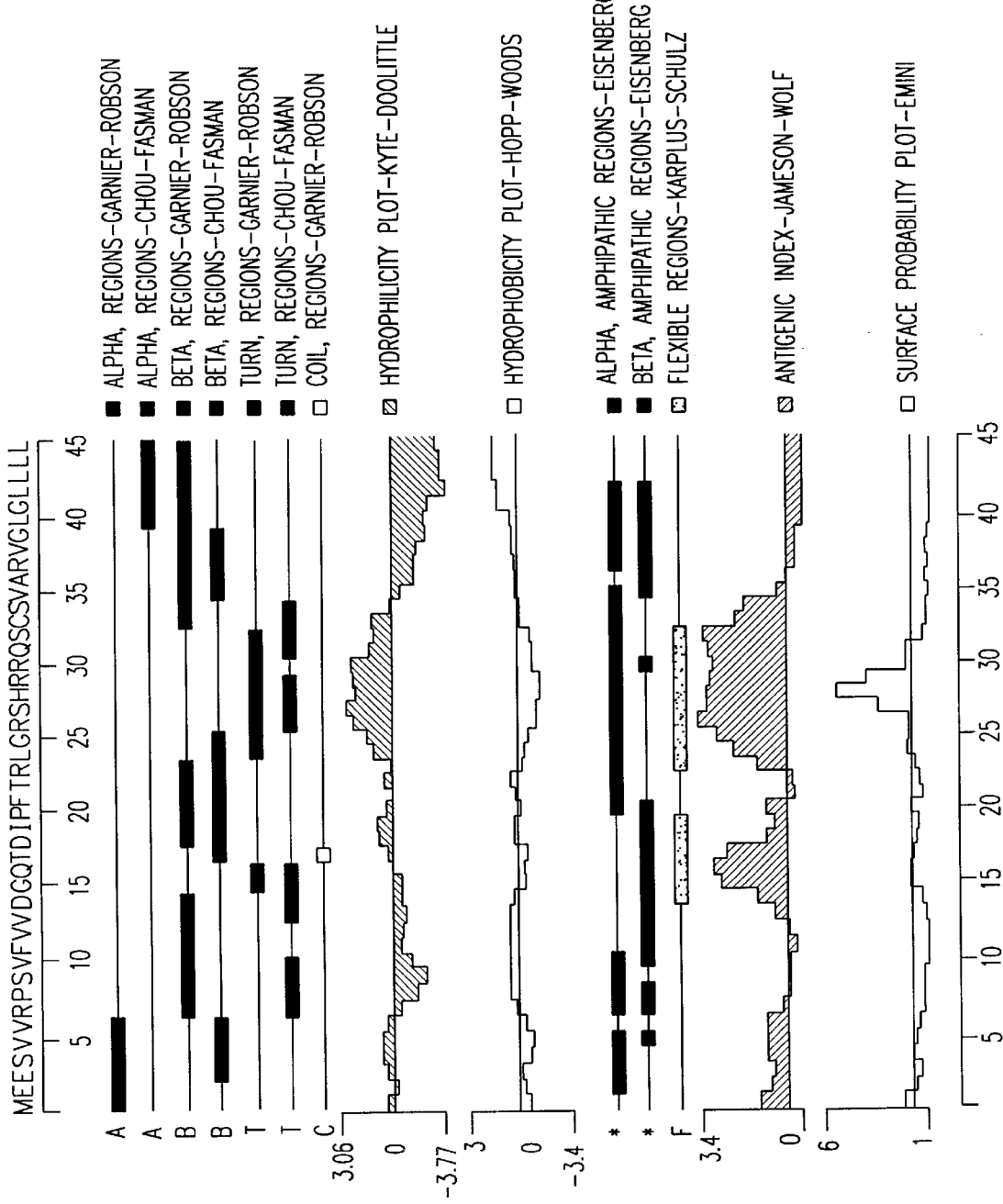
FIGS. 3A–F show an analysis of the AIM II amino acid sequence (SEQ ID NO:2). Alpha, beta, turn and coil regions; hydrophilicity and hydrophobicity; amphipathic regions; flexible regions; antigenic index and surface probability are shown. In the "Antigenic Index — Jameson-Wolf" graph, about amino acid residues 13–20, 23–36, 69–79, 85–94, 167–178, 184–196, 221–233 in FIGS. 1A and B (SEQ ID NO:2) correspond to the shown highly antigenic regions of the AIM II protein (SEQ ID NO:2).
Figure 3B:
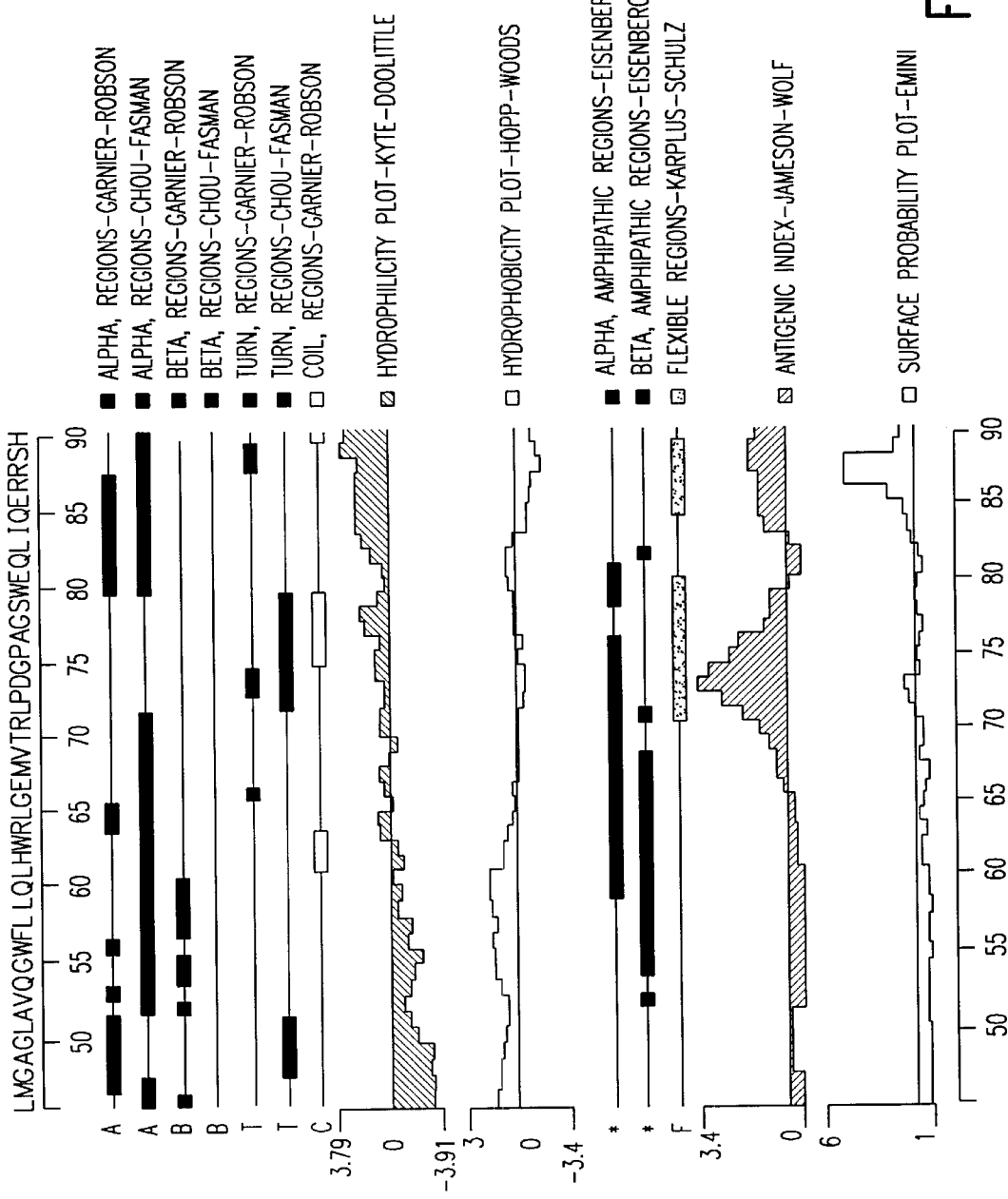
Figure 3C:
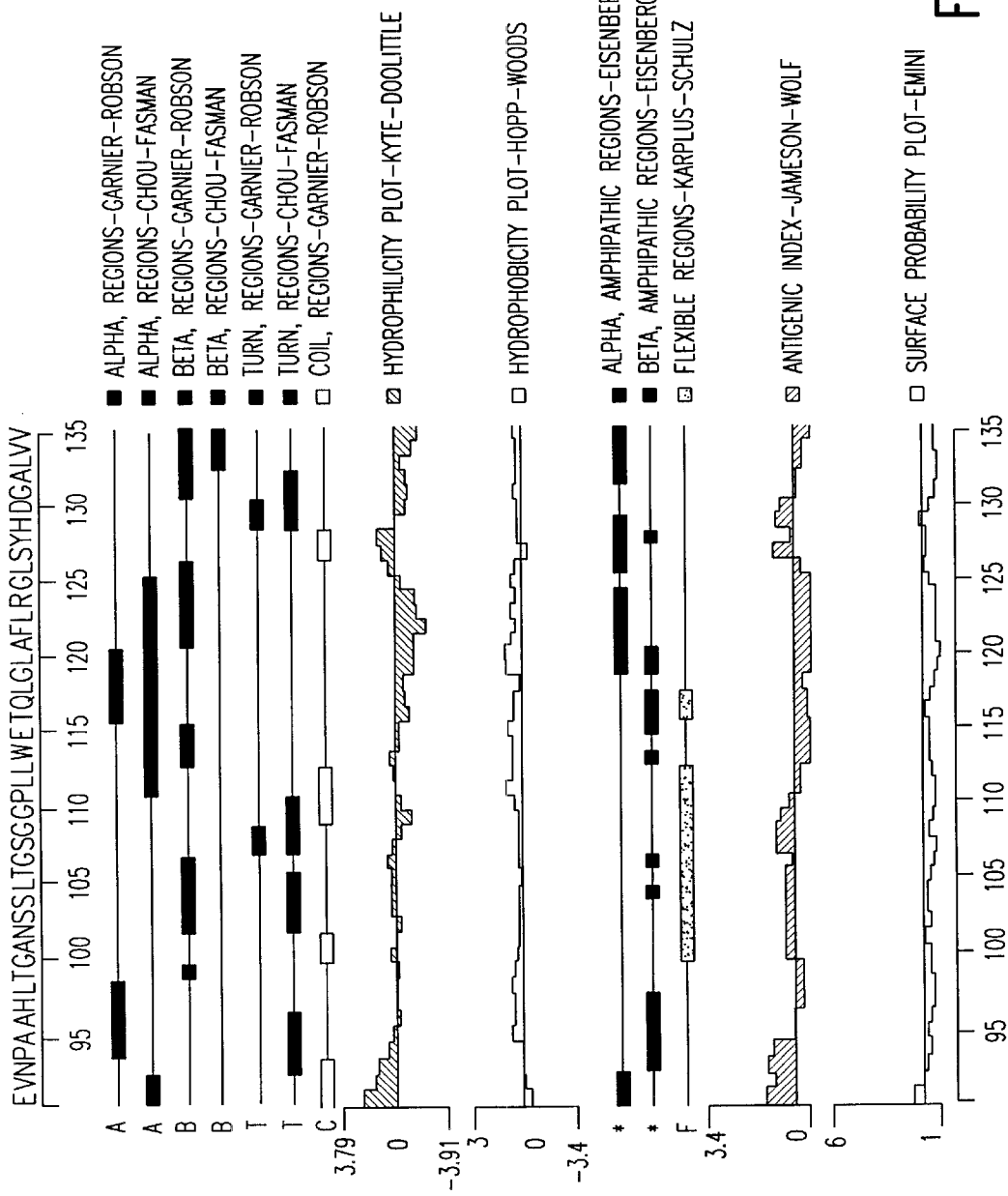
Figure 3D:
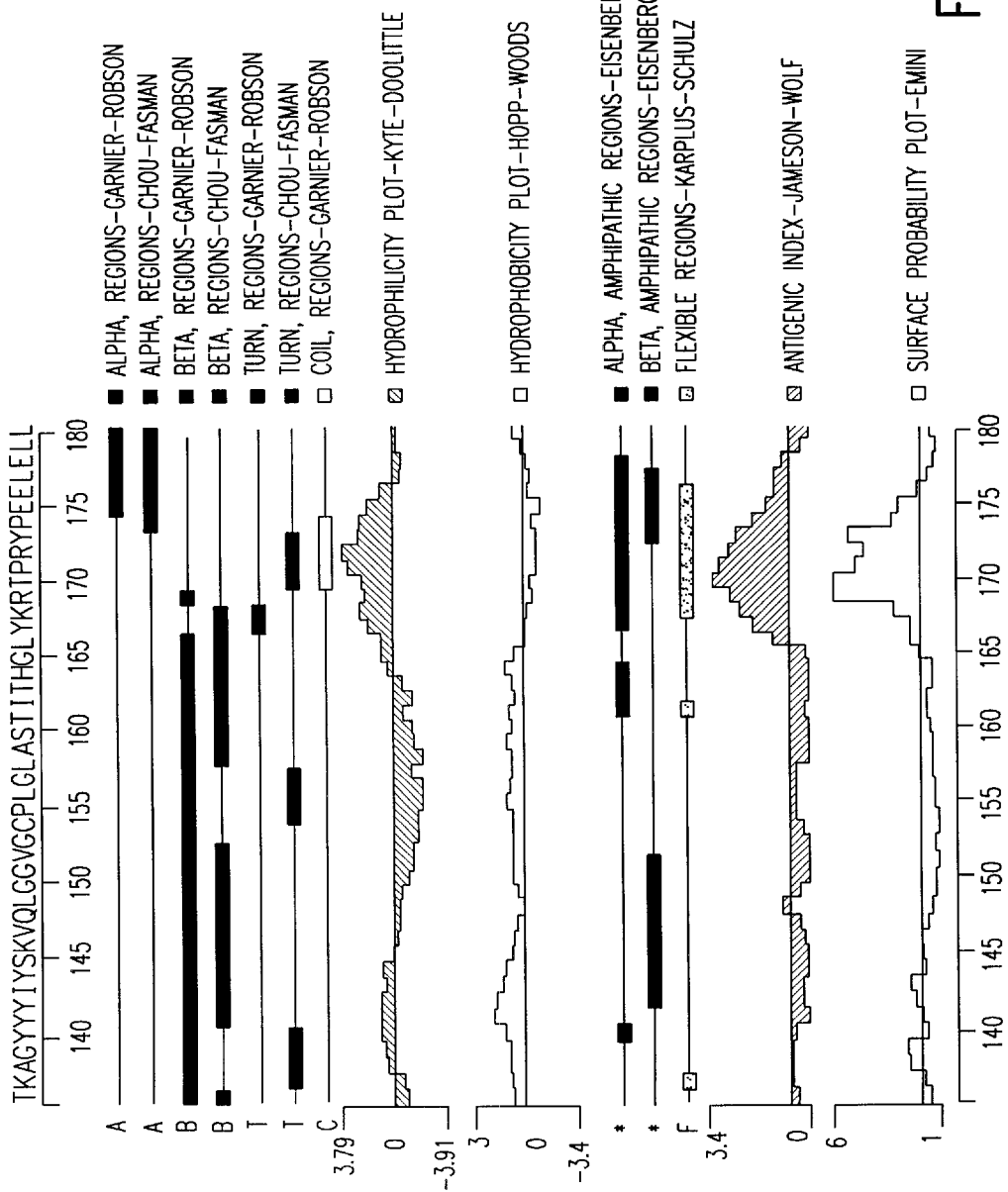
Figure 3E:
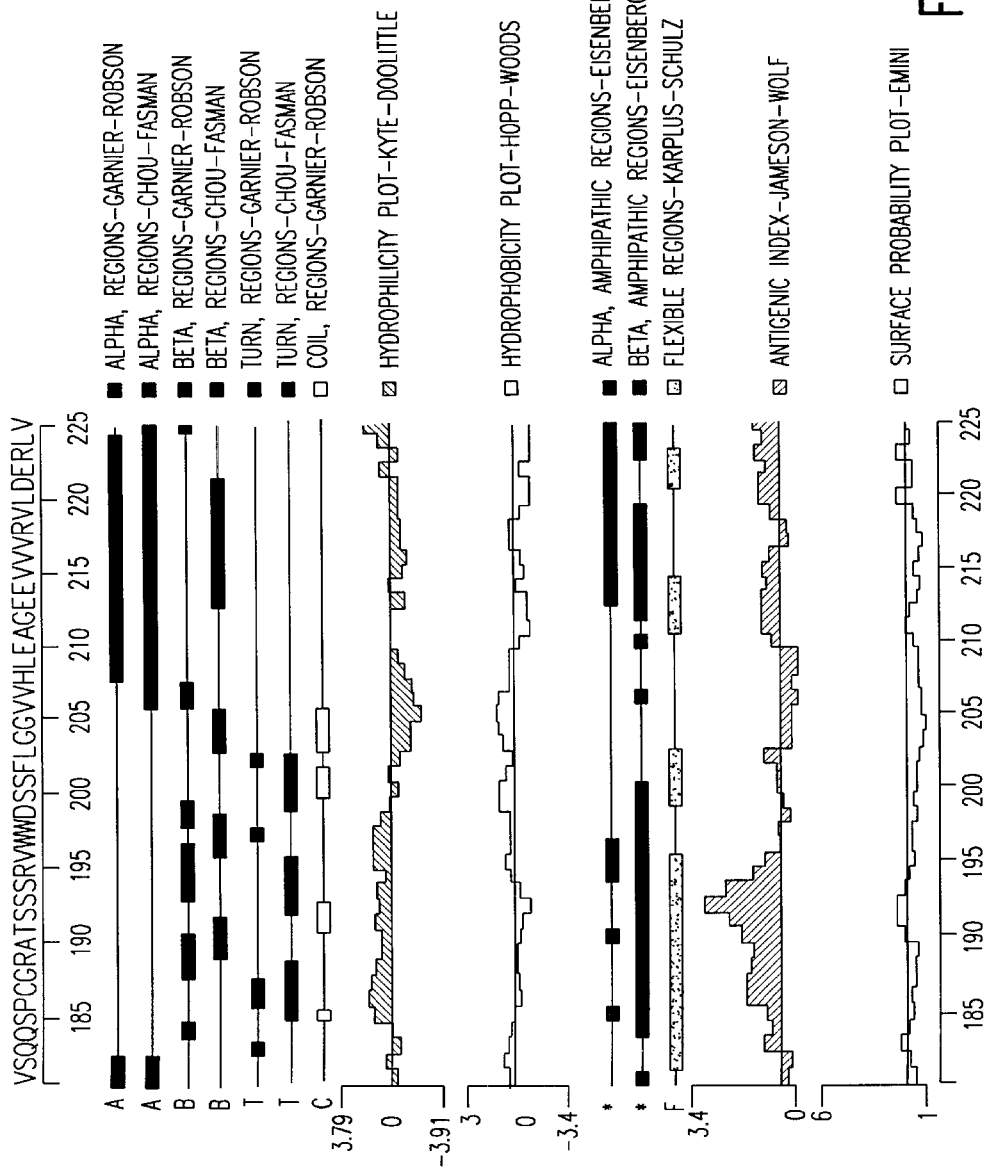
Figure 3F:
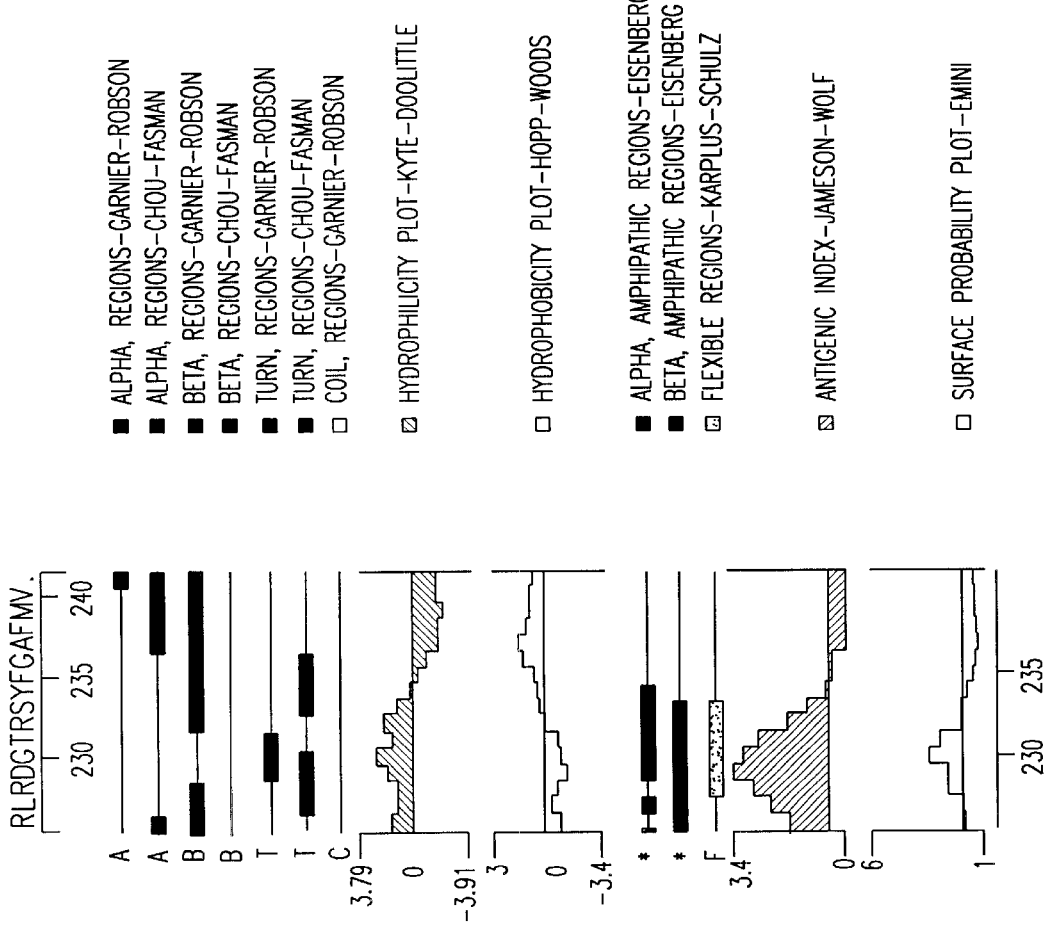

The present invention provides isolated nucleic acid molecules comprising a polynucleotide encoding an AIM II polypeptide having the amino acid sequence shown in FIGS. 1A and B (SEQ ID NO:2), which was determined by sequencing a cloned cDNA. The AIM II protein of the present invention shares sequence homology with human TNF-α (SEQ ID NO:3), human TNF-β (SEQ ID NO:4), human lymphotoxin (SEQ ID NO:5) and human Fas Ligand (SEQ ID NO:6) (FIGS. 2A–F). The nucleotide sequence shown in FIGS. 1A and B (SEQ ID NO:1) were obtained by sequencing the a cDNA clone, which was deposited on Aug. 22, 1996 at the American Type Culture Collection, 10801 University Blvd., Manassas Va. 20110-2209, and given accession number 97689. The deposited clone is contained in the pBluescript SK(–) plasmid (Stratagene, La Jolla, Calif.). The nucleotide sequence shown in FIGS. 1C and D was obtained by sequencing the a cDNA clone, which was deposited on Mar. 15, 1996 at the American Type Culture Collection, 10801 University Boulevard Manassas Va. 20110-2209, USA and given accession number 97483.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A and B, a nucleic acid molecule of the present invention encoding an AIM II polypeptide may be obtained using standard cloning and screening procedures, such as those for cloning cDNAs using mRNA as starting material. Illustrative of the invention, the nucleic acid molecule described in FIGS. 1A and B (SEQ ID NO:1) was discovered in a cDNA library derived from human macrophage ox LDL (HMCCB64). The gene was also identified in cDNA libraries from activated T-cells (HT4CC72). The determined nucleotide sequence of the AIM II cDNA of FIGS. 1A and B (SEQ ID NO:1) contains an open reading frame encoding a protein of 240 amino acid residues, with an initiation codon at positions 49–51 of the nucleotide sequence in FIGS. 1A and B (SEQ ID NO:1), an extracellular domain comprising amino acid residues from about 60 to about 240 in FIGS. 1A and B (SEQ ID NO:2), a transmembrane domain comprising amino acid residues from about 37 to about 59 in FIGS. 1A and B (SEQ ID NO:2), a intracellular domain comprising amino acid residues from about 1 to about 36 in FIGS. 1A and B (SEQ ID NO:2) and a deduced molecular weight of about 26.4 kDa. The AIM II protein shown in FIGS. 1A and B (SEQ ID NO:2) is about 27% identical and about 51% similar to the amino acid sequence of human Fas Ligand (FIG. 2A–F) and is about 26% identical and about 47% similar to the amino acid sequence of human TNF-α (FIGS. 2A–F). TNF-ligand like molecules function as dimers, given that AIM II is homologous to TNF-ligand like molecules, it is likely that it also functions as a homodimer.

As one of ordinary skill would appreciate, due to the possibilities of sequencing errors discussed above, the predicted AIM II polypeptide encoded by the deposited cDNA comprises about 240 amino acids, but may be anywhere in the range of 230–250 amino acid. It will further be appreciated that, depending on the criteria used, concerning the exact "address" of the extracelluar, intracelluar and transmembrane domains of the AIM II polypeptide differ slightly. For example, the exact location of the AIM II extracellular domain in FIGS. 1A and B (SEQ ID NO:2) may vary slightly (e.g., the address may "shift" by about 1 to 5 residues) depending on the criteria used to define the domain.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIGS. 1A and B (SEQ ID NO:1) or FIGS. 1C and D (SEQ ID NO:38); DNA molecules comprising the coding sequence for the AIM II protein shown in FIGS. 1A and B (SEQ ID NO:2) or FIGS. 1C and D (SEQ ID NO:41); and DNA molecules which comprise a sequence substantially different from those described above but which, due to the degeneracy of the genetic code, still encode the AIM II protein. Of course, the genetic code is well known in the art. Thus, it would be routine for one skilled in the art to generate such degenerate variants.

In addition, the invention provides a nucleic acid molecule having a nucleotide sequence related to a portion of SEQ ID NO:1 which has been determined from the following related cDNA clone: HT4CC72R (SEQ ID NO:20).

In another aspect, the invention provides isolated nucleic acid molecules encoding the AIM II polypeptide having an amino acid sequence encoded by the cDNA clone contained in the plasmid deposited as ATCC Deposit No. 97689 on Aug. 22, 1996 or by the cDNA clone contained in the plasmid deposited as ATCC Deposit No. 97483 on Mar. 15, 1996. Preferably, this nucleic acid molecule will encode the polypeptide encoded by the above-described deposited cDNA clone. The invention further provides an isolated nucleic acid molecule having the nucleotide sequence shown in FIGS. 1A and B (SEQ ID NO:1) or FIGS. 1C and D (SEQ ID NO:38) or the nucleotide sequence of the AIM II cDNA contained in the above-described deposited clones, or a nucleic acid molecule having a sequence complementary to one of the above sequences. Such isolated molecules, particularly DNA molecules, are useful as probes for gene mapping, by in situ hybridization with chromosomes, and for detecting expression of the AIM II gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in FIGS. 1A and B (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125 or 1150 nt in length are also useful according to the present invention as are fragments corresponding to most, if not all, of the nucleotide sequence of the deposited cDNA or as shown in FIGS. 1A and B (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A and B (SEQ ID NO:1).

Preferred nucleic acid fragments of the present invention include nucleic acid molecules encoding epitope-bearing portions of the AIM II protein. In particular, such nucleic acid fragments of the present invention include nucleic acid molecules encoding: a polypeptide comprising amino acid residues from about 13 to about 20 in FIGS. 1A and B (SEQ ID NO:2); a polypeptide comprising amino acid residues from about 23 to about 36 in FIG. 1 (SEQ ID NO:2); a polypeptide comprising amino acid residues from about 69 to about 79 in FIGS. 1A and B (SEQ ID NO:2); a polypeptide comprising amino acid residues from about 85 to about 94 in FIGS. 1A and B (SEQ ID NO:2); a polypeptide comprising amino acid residues from about 167 to about 178 in FIGS. 1A and B (SEQ ID NO:2); a polypeptide comprising amino acid residues from about 184 to about 196 in FIGS. 1A and B (SEQ ID NO:2); and a polypeptide comprising amino acid residues from about 221 to about 233 in FIGS. 1A and B (SEQ ID NO:2). The inventors have determined that the above polypeptide fragments are antigenic regions of the AIM II protein. Methods for determining other such epitope-bearing portions of the AIM II protein are described in detail below.

AIM II polynucleotides may be used in accordance with the present invention for a variety of applications, particularly those that make use of the chemical and biological properties of the AIM II. Among these applications in autoimmune disease and aberrant cellular proliferation. Additional applications relate to diagnosis and to treatment of disorders of cells, tissues, and organisms.

This invention is also related to the use of the AIM II polynucleotides to detect complementary polynucleotides such as, for example, as a diagnostic reagent. Detection of a mutated form of an AIM II associated with a dysfunction will provide a diagnostic tool that can add or define a diagnosis of a disease or susceptibility to disease which results from under-expression, over-expression or altered expression of AIM II, such as, for example, autoimmune diseases. The polynucleotide encoding the AIM II may also be employed as a diagnostic marker for expression of the polypeptide of the present invention.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97689. By "stringent hybridization conditions" is intended overnight incubation at 42° C. in a solution comprising: 50% formamide, 5×SSC (150 mM NaCl, 15mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A and B (SEQ ID NO:1)).

Of course, a polynucleotide which hybridizes only to a poly A sequence (such as the 3' terminal poly(A) tract of the AIM II cDNA shown in FIGS. 1A and B (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode an AIM II polypeptide may include, but are not limited to those encoding the amino acid sequence of the polypeptide, by itself; the coding sequence for the polypeptide and additional sequences, such as those encoding a leader or secretory sequence, such as a pre-, or pro- or prepro- protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the AIM II fused to Fc at the N- or C-terminus.

Nucleic acid molecules according to the present invention further include those encoding the full-length AIM-II polypeptide lacking the N-terminal methionine.

The present invention further relates to variants of the nucleic acid molecules of the present invention, which encode portions, analogs or derivatives of the AIM II protein. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the AIM II protein or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the AIM II polypeptide having the complete amino acid sequence in FIGS. 1A and B (SEQ ID NO:2); (b) a nucleotide sequence encoding the AIM II polypeptide having the amino acid sequence in FIGS. 1A and B (SEQ ID NO:2), but lacking the N-terminal methionine; (c) a nucleotide sequence encoding the AIM II polypeptide having the complete amino acid sequence encoded by the cDNA clone contained in ATCC Deposit No. 97689; (d) a nucleotide sequence encoding the AIM II polypeptide extracellular domain; (e) a nucleotide sequence encoding the AIM II polypeptide transmembrane domain; (f) a nucleotide sequence encoding the AIM II polypeptide intracellular domain; (g) a nucleotide sequence encoding a soluble AIM II polypeptide having the extracellular and intracellular domains but lacking the transmembrane domain; and (h) a nucleotide sequence complementary to any of the nucleotide sequences in (a), (b), (c), (d), (e), (f) or (g) above.

By a polynucleotide having a nucleotide sequence at least, for example, 95% "identical" to a reference nucleotide sequence encoding an AIM II polypeptide is intended that the nucleotide sequence of the polynucleotide is identical to the reference sequence except that the polynucleotide sequence may include up to five point mutations per each 100 nucleotides of the reference nucleotide sequence encoding the AIM II polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A and B or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIGS. 1A and B (SEQ ID NO:1) or to the nucleic acid sequence of the deposited cDNA, irrespective of whether they encode a polypeptide having AIM II activity. This is because even where a particular nucleic acid molecule does not encode a polypeptide having AIM II activity, one of skill in the art would still know how to use the nucleic acid molecule, for instance, as a hybridization probe or a polymerase chain reaction (PCR) primer. Uses of the nucleic acid molecules of the present invention that do not encode a polypeptide having AIM II activity include, inter alia, (1) isolating the AIM II gene or allelic variants thereof in a cDNA library; (2) in situ hybridization (e.g., "FISH") to metaphase chromosomal spreads to provide precise chromosomal location of the AIM II gene, as described in Verma et al., *Human Chromosomes: A Manual of Basic Techniques*, Pergamon Press, New York (1988); and (3) Northern Blot analysis for detecting AIM II mRNA expression in specific tissues.

Preferred, however, are nucleic acid molecules having sequences at least 90%, 95%, 96%, 97%, 98% or 99% identical to the nucleic acid sequence shown in FIGS. 1A and B (SEQ ID NO:1) or to the nucleic acid sequence of the deposited cDNA which do, in fact, encode a polypeptide having AIM II protein activity. By "a polypeptide having AIM II activity" is intended polypeptides exhibiting activity similar, but not necessarily identical, to an activity of the AIM II protein of the invention, as measured in a particular biological assay. For example, AIM II protein cytotoxic activity can be measured using propidium iodide staining to demonstrate apoptosis as described by Zarres et al., *Cell* 70: 31–46 (1992). Alternatively, AIM II induced apoptosis can also be measured using TUNEL staining as described by Gavierli et al., *J. Cell. Biol.* 119: 493–501 (1992).

Briefly, the propidium iodide staining is performed as follows. Cells either from tissue or culture are fixed in formaldehyde, cut into frozen sections and stained with propidium iodide. The cell nuclei are visualized by propidium iodide using confocal fluorescent microscopy. Cell death is indicated by pyknotic nuclei (chromosome clumping, shrinking and/or fragmentation of nuclei).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 1A and B (SEQ ID NO:1) will encode a polypeptide "having AIM II protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having AIM II protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of AIM II polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

In addition to the use of expression vectors in the practice of the present invention, the present invention further includes novel expression vectors comprising operator and promoter elements operatively linked to nucleotide sequences encoding a protein of interest. One example of such a vector is pHE4–5 which is described in detail below.

Figure 10:
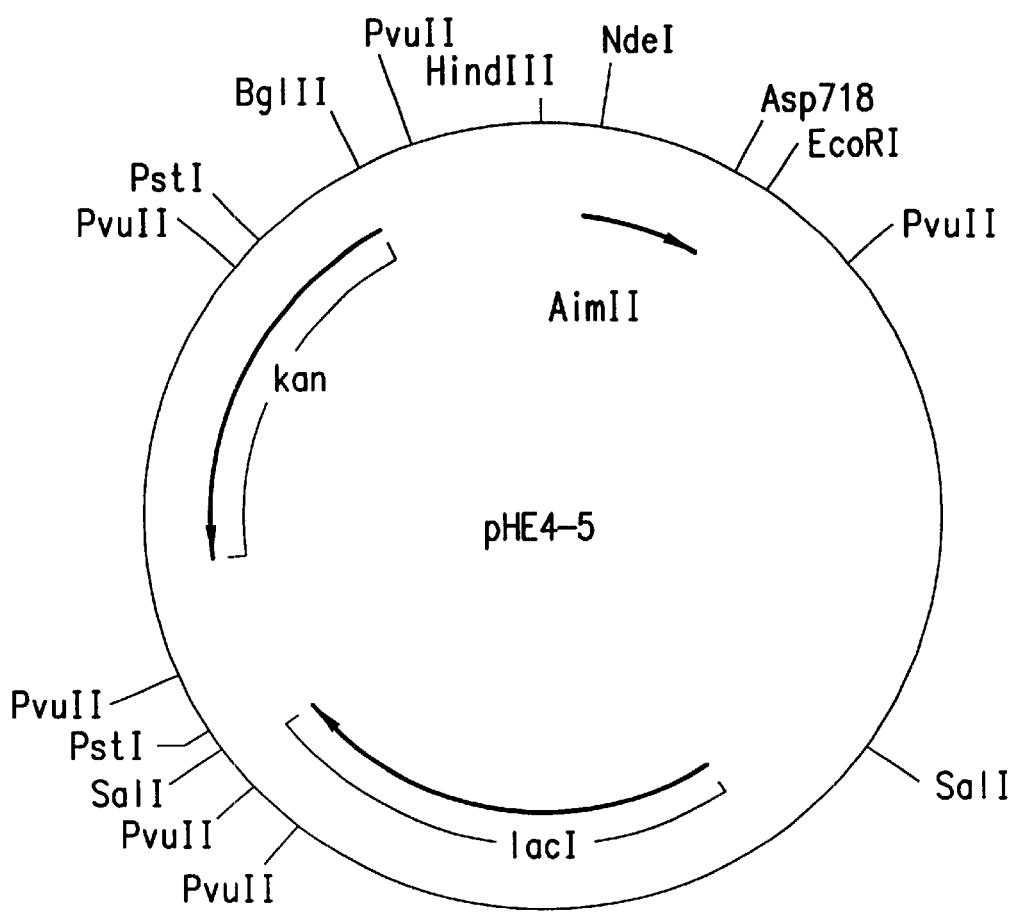
FIG. 10 shows a schematic representation of the pHE4–5 expression vector (SEQ ID NO:50) and the subcloned AIMII cDNA coding sequence. The locations of the kanamycin resistance marker gene, the AIMII coding sequence, the oriC sequence, and the lacIq coding sequence are indicated.

As summarized in FIGS. 10 and 11, components of the pHE4–5 vector (SEQ ID NO:50) include: 1) a neomycin-phosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq). The origin of replication (oriC) is derived from pUC 19 (LTI, Gaithersburg, Md.). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. A nucleotide sequence encoding AIMII (SEQ ID NO:1), is operatively linked to the promoter and operator by inserting the nucleotide sequence between the NdeI and Asp718 sites of the pHE4–5 vector.

As noted above, the pHE4–5 vector contains a lacIq gene. LacIq is an allele of the lacI gene which confers tight regulation of the lac operator. Amann, E. et al., *Gene* 69:301–315 (1988); Stark, M., *Gene* 51:255–267 (1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). AIMII thus is not produced in appreciable quantities in uninduced host cells containing the pHE4–5 vector. Induction of these host cells by the addition of an agent such as IPTG, however, results in the expression of the AIMII coding sequence.

The promoter/operator sequences of the pHE4–5 vector (SEQ ID NO:51) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802–807.

The pHE4 series of vectors contain all of the components of the pHE4–5 vector except for the AIMII coding sequence. Features of the pHE4 vectors include optimized synthetic T5 phage promoter, lac operator, and Shine-Delagamo sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4–5 vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4–5 vector (SEQ ID NO:50).

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223–3, pKK233–3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., The *Journal of Biological Chemistry*, Vol. 270, No. 16:9459–9471 (1995).

The AIM II protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

AIM II Polypeptides and Fragments

The invention further provides an isolated AIM II polypeptide having the amino acid sequence encoded by the deposited cDNA, or the amino acid sequence in FIGS. 1A and B (SEQ ID NO:2), or a peptide or polypeptide comprising a portion of the above polypeptides.

It will be recognized in the art that some amino acid sequences of the AIM II polypeptide can be varied without significant effect of the structure or function of the protein. If such differences in sequence are contemplated, it should be remembered that there will be critical areas on the protein which determine activity.

Thus, the invention further includes variations of the AIM II polypeptide which show substantial AIM II polypeptide activity or which include regions of AIM II protein such as the protein portions discussed below. Such mutants include deletions, insertions, inversions, repeats, and type substitutions. As indicated above, guidance concerning which amino acid changes are likely to be phenotypically silent can be found in Bowie, J.U., et al., "Deciphering the Message in Protein Sequences: Tolerance to Amino Acid Substitutions," *Science* 247:1306–1310 (1990).

Thus, the fragment, derivative or analog of the polypeptide of FIGS. 1A and B (SEQ ID NO:2), or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the AIM II protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the AIM II receptor of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given AIM-II polypeptide will not be more than 50, 40, 30, 25, 20, 15, 10, 5 or 3.

Amino acids in the AIM II protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

Amino Terminal Deletions

Also included in the present invention are amino terminal deletion mutants. Such mutants include those comprising the amino acid sequence shown in SEQ ID NO:2 having a deletion of at least first N-terminal amino acid but not more than the first 114 N-terminal amino acid residues of SEQ ID NO:2. Alternatively, the deletion will include at least the first 35 N-terminal amino acid residues but not more than the first 114 N-terminal amino acid residues of SEQ ID NO:2. Alternatively, the deletion will include at least the first 59 N-terminal amino acid residues but not more than the first 114 N-terminal amino acid residues of SEQ ID NO:2. Alternatively, the deletion will include at least the first 67 N-terminal amino acid residues but not more than the first 114 N-terminal amino acid residues of SEQ ID NO:2. Alternatively, the deletion will include at least the first 68 N-terminal amino acid residues but not more than the first 114 N-terminal amino acid residues of SEQ ID NO:2. Alternatively, the deletion will include at least the first 73 N-terminal amino acid residues but not more than the first 114 N-terminal amino acid residues of SEQ ID NO:2. Alternatively, the deletion will include at least the first 82 N-terminal amino acid residues but not more than the first 114 N-terminal amino acid residues of SEQ ID NO:2. Alternatively, the deletion will include at least the first 100 N-terminal amino acid residues but not more than the first 114 N-terminal amino acid residues of SEQ ID NO:2.

In addition to the ranges of N-terminal deletion mutants described above, the present invention is also directed to all combinations of the above described ranges. For example, the deletions of at least the first 59 N-terminal amino acid residues but not more than the first 67 N-terminal amino acid residues of SEQ ID NO:2; deletions of at least the first 59 N-terminal amino acid residues but not more than the first 68 N-terminal amino acid residues of SEQ ID NO:2; deletions of at least the first 59 N-terminal amino acid residues but not more than the first 73 N-terminal amino acid residues of SEQ ID NO:2; deletions of at least the first 59 N-terminal amino acid residues but not more than the first 82 N-terminal amino acid residues of SEQ ID NO:2; deletions of at least the first 59 N-terminal amino acid residues but not more than the first 100 N-terminal amino acid residues of SEQ ID NO:2; deletions of at least the first 67 N-terminal amino acid residues but not more than the first 73 N-terminal amino acid residues of SEQ ID NO:2; deletions of at least the first 67 N-terminal amino acid residues but not more than the first 82 N-terminal amino acid residues of SEQ ID NO:2; deletions of at least the first 67 N-terminal amino acid residues but not more than the first 100 N-terminal amino acid residues of SEQ ID NO:2; deletions of at least the first 68 N-terminal amino acid residues but not more than the first 73 N-terminal amino acid residues of SEQ ID NO:2; deletions of at least the first 68 N-terminal amino acid residues but not more than the first 82 N-terminal amino acid residues of SEQ ID NO:2; deletions of at least the first 68 N-terminal amino acid residues but not more than the first 100 N-terminal amino acid residues of SEQ ID NO:2; deletions of at least the first 73 N-terminal amino acid residues but not more than the first 82 N-terminal amino acid residues of SEQ ID NO:2; deletions of at least the first 73 N-terminal amino acid residues but not more than the first 100 N-terminal amino acid residues of SEQ ID NO:2; deletions of at least the first 82 N-terminal amino acid residues but not more than the first 100 N-terminal amino acid residues of SEQ ID NO:2; etc. etc. etc. . . .

Preferred AIM II polypeptides are shown below (numbering starts with the first amino acid in the protein (Met):

| | |
|---|---|
| Gln(residue 60) to Val(residue 240) | His(62) to Val(240) |
| Leu(61) to Val(240) | Trp(63) to Val(240) |
| Arg(64) to Val(240) | Pro(94) to Val(240) |
| Leu(65) to Val(240) | Ala(95) to Val(240) |
| Gly(66) to Val(240) | Ala(96) to Val(240) |
| Glu(67) to Val(240) | His(97) to Val(240) |
| Met(68) to Val(240) | Leu(98) to Val(240) |
| Val(69) to Val(240) | Thr(99) to Val(240) |
| Thr(70) to Val(240) | Gly(100) to Val(240) |
| Arg(71) to Val(240) | Ala(101) to Val(240) |
| Leu(72) to Val(240) | Asn(102) to Val(240) |
| Pro(73) to Val(240) | Ser(103) to Val(240) |
| Asp(74) to Val(240) | Ser(104) to Val(240) |
| Gly(75) to Val(240) | Leu(105) to Val(240) |
| Pro(76) to Val(240) | Thr(106) to Val(240) |
| Ala(77) to Val(240) | Gly(107) to Val(240) |
| Gly(78) to Val(240) | Ser(108) to Val(240) |
| Ser(79) to Val(240) | Gly(109) to Val(240) |
| Trp(80) to Val(240) | Gly(110) to Val(240) |
| Glu(81) to Val(240) | Pro(111) to Val(240) |
| Gln(82) to Val(240) | Leu(112) to Val(240) |
| Leu(83) to Val(240) | Leu(113) to Val(240) |
| Ile(84) to Val(240) | Trp(114) to Val(240) |
| Gln(85) to Val(240) | |
| Glu(86) to Val(240) | |
| Arg(87) to Val(240) | |
| Arg(88) to Val(240) | |
| Ser(89) to Val(240) | |
| His(90) to Val(240) | |
| Glu(91) to Val(240) | |
| Val(92) to Val(240) | |
| Asn(93) to Val(240) | |

Particularly preferred embodiments include the AIM II N-terminal deletions Gln-60 to Val-240 (AIM II (aa 60–240)), Met-68 to Val-240 (AIM II (aa 68–240)), Val-69 to Val-240(AIM II (aa 69–240)), Asp-74 to Val-240 (AIM II (aa 74–240)), Leu-83 to Val-240(AIM II (aa 83–240)), and Ala-101 to Val-240 (AIM II (aa 101–240)).

The natural processed form of AIM II that was affinity purified on an LT-β receptor column from conditioned media of MCA-38 cells transformed with full length AIM II cDNA is Leu-83 to Val-240 in SEQ ID NO:2. (See, Example 10). However, it appears that AIM II is processed differently in COS cells, producing an AIM II that is cleaved between Glu-67 and Met-68 to yield a polypeptide having amino acids 68–240 in SEQ ID NO:2. In addition, COS cells also cleave the AIM II between Met-68 and Val-69, resulting a polypeptide having amino acids 69–240 in SEQ ID NO:2.

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host. For example, a recombinantly produced version of the AIM II polypeptide can be substantially purified by the one-step method described in Smith and Johnson, Gene 67:31–40 (1988).

The polypeptides of the present invention include the polypeptide encoded by the deposited cDNA, the polypeptide of FIGS. 1A and B (SEQ ID NO:2), the polypeptide of FIGS. 1A and B (SEQ ID NO:2) lacking the N-terminal methinone, the extracellular domain, the transmembrane domain, the intracellular domain, soluble polypeptides comprising all or part of the extracellular and intracelluar domains but lacking the transmembrane domain, as well as polypeptides which are at least 80% identical, more preferably at least 90% or 95% identical, still more preferably at least 96%, 97%, 98% or 99% identical to the polypeptide encoded by the deposited cDNA, to the polypeptide of FIGS. 1A and B (SEQ ID NO:2), and also include portions of such polypeptides with at least 30 amino acids and more preferably at least 50 amino acids.

By a polypeptide having an amino acid sequence at least, for example, 95% "identical" to a reference amino acid sequence of an AIM II polypeptide is intended that the amino acid sequence of the polypeptide is identical to the reference sequence except that the polypeptide sequence may include up to five amino acid alterations per each 100 amino acids of the reference amino acid of the AIM II polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A and B (SEQ ID NO:2) or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 5371 1. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

As used herein the term "AIM II" polypeptide includes membrane-bound proteins (comprising a cytoplasmic domain, a transmembrane domain, and an extracellular domain) as well as truncated proteins that retain the AIM II polypeptide activity. In one embodiment, soluble AIM II polypeptides comprise all or part of the extracellular domain of an AIM II protein, but lack the transmembrane region that would cause retention of the polypeptide on a cell membrane. Soluble AIM II may also include part of the transmembrane region or part of the cytoplasmic domain or other sequences, provided that the soluble AIM II protein is capable of being secreted. A heterologous signal peptide can be fused to the N-terminus of the soluble AIM II polypeptide such that the soluble AIM II polypeptide is secreted upon expression.

The polypeptide of the present invention could be used as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al. *Cell* 37: 767–778 (1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of a polypeptide of the invention.

Non-limiting examples of antigenic polypeptides or peptides that can be used to generate AIM II-specific antibodies include: a polypeptide comprising amino acid residues from about 13 to about 20 in FIGS. 1A and B (SEQ ID NO:2); a polypeptide comprising amino acid residues from about 23 to about 36 in FIG. 1 (SEQ ID NO:2); a polypeptide comprising amino acid residues from about 69 to about 79 in FIGS. 1A and B (SEQ ID NO:2); a polypeptide comprising amino acid residues from about 85 to about 94 in FIGS. 1A and B (SEQ ID NO:2); a polypeptide comprising amino acid residues from about 167 to about 178 in FIGS. 1A and B (SEQ ID NO:2); a polypeptide comprising amino acid residues from about 184 to about 196 in FIGS. 1A and B (SEQ ID NO:2); and a polypeptide comprising amino acid residues from about 221 to about 233 in FIGS. 11A and B (SEQ ID NO:2). As indicated above, the inventors have determined that the above polypeptide fragments are antigenic regions of the AIM II protein.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986).

The AIM II polypeptide of the present invention may be employed to treat lymphoproliferative disease which results in lymphadenopathy, the AIM II mediates apoptosis by stimulating clonal deletion of T-cells and may therefore, be employed to treat autoimmune disease, to stimulate peripheral tolerance and cytotoxic T-cell mediated apoptosis. The AIM II may also be employed as a research tool in elucidating the biology of autoimmune disorders including systemic lupus erythematosus (SLE), immunoproliferative disease lymphadenopathy (IPL), angioimmunoproliferative lymphadenopathy (AIL), immunoblastive lymphadenopathy (IBL), diabetes, and multiple sclerosis, allergies and to treat graft versus host disease.

The AIM II polypeptide of the present invention may also be employed to inhibit neoplasia, such as tumor cell growth. The AIM II polypeptide may be responsible for tumor destruction through apoptosis and cytotoxicity to certain cells. AIM II may also be employed to treat diseases which require growth promotion activity, for example, restenosis, since AIM II has proliferation effects on cells of endothelial origin. AIM II may, therefore, also be employed to regulate hematopoiesis in endothelial cell development.

This invention also provides a method for identification of molecules, such as receptor molecules, that bind AIM II. Genes encoding proteins that bind AIM II, such as receptor proteins, can be identified by numerous methods known to those of skill in the art, for example, ligand panning and FACS sorting. Such methods are described in many laboratory manuals such as, for instance, Coligan et al., *Current Protocols in Immunology*, 1(2):Chapter 5 (1991).

For instance, expression cloning may be employed for this purpose. To this end polyadenyiated RNA is prepared from a cell responsive to AIM II, a cDNA library is created from this RNA, the library is divided into pools and the pools are transfected individually into cells that are not responsive to AIM II. The transfected cells then are exposed to labeled AIM II. (AIM II can be labeled by a variety of well-known techniques including standard methods of radio-iodination or inclusion of a recognition site for a site-specific protein kinase.) Following exposure, the cells are fixed and binding of AIM II is determined. These procedures conveniently are carried out on glass slides.

Pools are identified of cDNA that produced AIM II-binding cells. Sub-pools are prepared from these positives, transfected into host cells and screened as described above. Using an iterative sub-pooling and re-screening process, one or more single clones that encode the putative binding molecule, such as a receptor molecule, can be isolated.

Alternatively a labeled ligand can be photo affinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess AIM II binding capacity of AIM II binding molecules, such as receptor molecules, in cells or in cell-free preparations.

As one of skill in the art will appreciate, AIM II polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric AIM II protein or protein fragment alone (Fountoulakis et al., *J. Biochem* 270:3958–3964 (1995)).

The present inventors have discovered that AIM II is expressed in spleen, thymus and bone marrow tissue. For a number of disorders, such as septic shock, inflammation, cerebral malaria, activation of the HIV virus, graft-host rejection, bone resorption, rheumatoid arthritis and cachexia, it is believed that significantly higher or lower levels of AIM II gene expression can be detected in certain tissues (e.g., spleen, thymus and bone marrow tissue) or bodily fluids (e.g., serum, plasma, urine, synovial fluid or spinal fluid) taken from an individual having such a disorder, relative to a "standard" AIM II gene expression level, i.e., the AIM II expression level in tissue or bodily fluids from an individual not having the disorder. Thus, the invention provides a diagnostic method useful during diagnosis of a disorder, which involves: (a) assaying AIM II gene expression level in cells or body fluid of an individual; (b) comparing the AIM II gene expression level with a standard AIM II gene expression level, whereby an increase or decrease in the assayed AIM II gene expression level compared to the standard expression level is indicative of a disorder.

AIM II Agonists and Antagonists

The invention also provides a method of screening compounds to identify those which enhance or block the action of AIM II on cells, such as its interaction with AIM II-binding molecules such as receptor molecules. An agonist is a compound which increases the natural biological functions of AIM II or which functions in a manner similar to AIM II, while antagonists decrease or eliminate such functions.

For example, a cellular compartment, such as a membrane preparation, may be prepared from a cell that expresses a molecule that binds AIM II, such as a molecule of a signaling or regulatory pathway modulated by AIM II. The preparation is incubated with labeled AIM II in the absence or the presence of a candidate molecule which may be an AIM II agonist or antagonist. The ability of the candidate molecule to bind the binding molecule or AIM II itself is reflected in decreased binding of the labeled ligand. Molecules which bind gratuitously, i.e., without inducing the effects of AIM II when bound to the AIM II binding molecule, are most likely to be good antagonists. Molecules that bind well and elicit effects that are the same as or closely related to AIM II, are good agonists.

AIM II-like effects of potential agonists and antagonists may by measured, for instance, by determining activity of a second messenger system following interaction of the candidate molecule with a cell or appropriate cell preparation, and comparing the effect with that of AIM II or molecules that elicit the same effects as AIM II. Second messenger systems that may be useful in this regard include but are not limited to AMP guanylate cyclase, ion channel or phosphoinositide hydrolysis second messenger systems.

Another example of an assay for AIM II antagonists is a competitive assay that combines AIM II and a potential antagonist with membrane-bound AIM II receptor molecules or recombinant AIM II receptor molecules under appropriate conditions for a competitive inhibition assay. AIM II can be labeled, such as by radioactivity, such that the number of AIM II molecules bound to a receptor molecule can be determined accurately to assess the effectiveness of the potential antagonist.

Potential antagonists include small organic molecules, peptides, polypeptides and antibodies that bind to a polypeptide of the invention, and thereby inhibit or extinguish its activity. Potential antagonists also may be small organic molecules, a peptide, a polypeptide such as a closely related protein or antibody that binds the same sites on a binding molecule, such as a receptor molecule, without inducing AIM II-induced activities, thereby preventing the action of AIM II by excluding AIM II from binding.

Other potential antagonists include antisense molecules. Antisense technology can be used to control gene expression through antisense DNA or RNA or through triple-helix formation. Antisense techniques are discussed, for example, in Okano, J. Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of AIM II. The antisense RNA oligonucleotide hybridizes to the mRNA in vivo and blocks translation of the mRNA molecule into AIM II polypeptide. The oligonucleotides described above can also be delivered to cells such that the antisense RNA or DNA may be expressed in vivo to inhibit production of AIM II.

The antagonists may be employed in a composition with a pharmaceutically acceptable carrier, e.g., as hereinafter described.

The antagonists may be employed for instance to treat cachexia which is a lipid clearing defect resulting from a systemic deficiency of lipoprotein lipase, which is believed to be suppressed by AIM II. The AIM II antagonists may also be employed to treat cerebral malaria in which AIM II may play a pathogenic role. The antagonists may also be employed to treat rheumatoid arthritis by inhibiting AIM-II induced production of inflammatory cytokines, such as IL1 in the synovial cells. When treating arthritis, AIM II antagonists are preferably injected intra-articularly The AIM II antagonists may also be employed to prevent graft-host rejection by preventing the stimulation of the immune system in the presence of a graft.

The AIM II antagonists may also be employed to inhibit bone resorption and, therefore, to treat and/or prevent osteoporosis.

The antagonists may also be employed as anti-inflammatory agents, and to treat endotoxic shock. This critical condition results from an exaggerated response to bacterial and other types of infection.

Cancer Prognosis

It is believed that certain tissues in mammals with cancer express significantly reduced levels of the AIM II protein and mRNA encoding the AIM II protein when compared to a corresponding "standard" mammal, i.e., a mammal of the same species not having the cancer. Further, it is believed that reduced levels of the AIM II protein can be detected in certain body fluids (e.g., sera, plasma, urine, and spinal fluid) from mammals with cancer when compared to sera from mammals of the same species not having the cancer. Thus, the invention provides a diagnostic method useful during tumor diagnosis, which involves assaying the expression level of the gene encoding the AIM II protein in mammalian cells or body fluid and comparing the gene expression level with a standard AIM II gene expression level, whereby an decrease in the gene expression level over the standard is indicative of certain tumors.

Where a tumor diagnosis has already been made according to conventional methods, the present invention is useful as a prognostic indicator, whereby patients exhibiting enhanced AIM II gene expression may experience a better clinical outcome relative to patients expressing the gene at a lower level.

By "assaying the expression level of the gene encoding the AIM II protein" is intended qualitatively or quantitatively measuring or estimating the level of the AIM II protein or the level of the mRNA encoding the AIM II protein in a first biological sample either directly (e.g., by determining or estimating absolute protein level or mRNA level) or relatively (e.g., by comparing to the AIM II protein level or mRNA level in a second biological sample).

Preferably, the AIM II protein level or mRNA level in the first biological sample is measured or estimated and compared to a standard AIM II protein level or mRNA level, the standard being taken from a second biological sample obtained from an individual not having the cancer. As will be appreciated in the art, once a standard AIM II protein level or mRNA level is known, it can be used repeatedly as a standard for comparison.

By "biological sample" is intended any biological sample obtained from an individual, cell line, tissue culture, or other source which contains AIM II protein or mRNA. Biological samples include mammalian body fluids (such as sera, plasma, urine, synovial fluid and spinal fluid) which contain secreted mature AIM II protein, and ovarian, prostate, heart, placenta, pancreas liver, spleen, lung, breast and umbilical tissue.

The present invention is useful for detecting cancer in mammals. In particular the invention is useful during diagnosis of the of following types of cancers in mammals: breast, ovarian, prostate, bone, liver, lung, pancreatic, and spleenic. Preferred mammals include monkeys, apes, cats, dogs, cows, pigs, horses, rabbits and humans. Particularly preferred are humans.

Total cellular RNA can be isolated from a biological sample using the single-step guanidinium-thiocyanate-phenol-chloroform method described in Chomczynski and Sacchi, Anal. Biochem. 162:156–159 (1987). Levels of mRNA encoding the AIM II protein are then assayed using any appropriate method. These include Northern blot analysis (Harada et al., Cell 63:303–312 (1990)), S1 nuclease mapping (Fujita et al., Cell 49:357–367 (1987)), the polymerase chain reaction (PCR), reverse transcription in combination with the polymerase chain reaction (RT-PCR) (Makino et al., Technique 2:295–301 (1990)), and reverse transcription in combination with the ligase chain reaction (RT-LCR).

Assaying AIM II protein levels in a biological sample can occur using antibody-based techniques. For example, AIM II protein expression in tissues can be studied with classical immunohistological methods (Jalkanen, M., et al., *J. Cell. Biol.* 101:976–985 (1985); Jalkanen, M., et al.,*J. Cell. Biol.* 105:3087–3096 (1987)).

Other antibody-based methods useful for detecting AIM II protein gene expression include immunoassays, such as the enzyme linked immunosorbent assay (ELISA) and the radio-immunoassay (RIA).

Suitable lables are known in the art and include enzyme lables, such as, Glucose oxidase, and radioisotopes, such as iodine ($^{125}I$, $^{121}I$ ), carbon ($^{14}C$), sulpher ($^{35}S$), tritium ($^{3}H$), indium ($^{112}In$), and technetium ($^{99m}Tc$), and fluorescent labels, such as fluorescein and rhodamine, and biotin.

Therapeutics

The AIM II polypeptides, particularly human AIM-II polypeptides, may be employed to treat neoplasia, lymphadenopathy, autoimmune disease, graft versus host disease. In addition, the AIM II polypeptide of the present invention may be employed to inhibit neoplasia, such as tumor cell growth. The combination of AIM II protein with immunotherapeutic agent such as IL-2 or IL-12 could result in synergistic or additive effects that would be a very useful for the treatment of established cancers. The AIM II polypeptide may be responsible for tumor destruction through apoptosis and cytotoxicity to certain cells. AIM II may also be employed to treat diseases which require growth promotion activity, for example, restenosis, since AIM II has proliferation effects on cells of endothelial origin. AIM II may, therefore, also be employed to regulate hematopoiesis in endothelial cell development.

AIM II may act as a cytokine adjuvant or costimulatory molecule. The following experiments are performed to assess the in vivo AIM II protein on the host immune system.

Tumor or non-tumor bearing mice are treated with AIM II protein at three different doses (0.1 mg/kg, 10 mg/kg and 10 mg/kg, i.p., QD, 10–14 days, N=5 per group) before or after immunization with tumor antigen or superantigen, the mice are sacrificed weekly post treatment after blood collection. The spleens or the lymph nodes are used for the following in vitro analyses well known to those skilled in the art:

FACS analyses: Expression of surface markers for T. B. NK, Monocytes, Dendritic cells, costimulatory and adhesion molecules.
Cytokine production assays
T cell proliferation or cytotoxicity assay AIM II protein and tumor antigen may result in induction of the protective immunity, which could lead to protecting mice from the subsequent tumor challenge. In order to examine possibility the following experiment can be performed using syngeneic C57BL/6 mice to test the effect of AIM II on induction of tumor or Ag-specific protective immunity.

The MC-38 tumor-free mice treated with AIM II protein will be challenged with MC-3 8 or irrelevant murine sarcoma MCA-102 using techniques well known to those skilled in the art. Three possible results could be observed:

|  | Result #1 | Result #2 | Result #3 |
|---|---|---|---|
| MC-38. WT: | tumor (−) | tumor (−) | tumor (+) |
| MCA-102: | tumor (+) | tumor (−) | tumor (+) |

Indication from #1: Evidence of tumor-specific protective immunity
Indication from #2: Evidence of non-tumor specific immunity
Indication from #3: Lack the protective immunity If generation of tumor-specific protective immunity upon AIM II treatment is demonstrated, the following depletion experiment are performed to identify which leukocyte subpopulation is responsible for the tumor rejection. The mice will be treated with various mAb which recognize either the CD4+, or CD8+T cells, or NK cells or granunocytes (Grl+), or the specific cytokine such as IFNγ using techniques well known to those skilled in the art. Tumor growth in these antibody-treated mice is measured.

Modes of Administration

It will be appreciated that conditions, such as those discussed above, can be treated by administration of AIM II protein. Thus, the invention further provides a method of treating an individual in need of an increased level of AIM II activity comprising administering to such an individual a pharmaceutical composition comprising an effective amount of an isolated AIM II polypeptide of the invention, particularly a mature form of the AIM II, effective to increase the AIM II activity level in such an individual.

As a general proposition, the total pharmaceutically effective amount of AIM II polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the AIM II polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed.

Pharmaceutical compositions containing the AIM II of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

In addition to soluble AIM II polypeptides, AIM II polypeptides containing the transmembrane region can also be used when appropriately solubilized by including detergents, such as triton X-1 00, with buffer.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of an AIM II protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1:

Expression and Purification of AIM II in *E. coli*

A. Expression of AIM II with an N-terminal 6-His tag

The DNA sequence encoding the AIM II protein in the deposited cDNA clone is amplified using PCR oligonucleotide primers specific to the amino terminal sequences of the AIM II protein and to vector sequences 3' to the gene. Additional nucleotides containing restriction sites to facilitate cloning are added to the 5' and 3' sequences respectively.

A 22 kDa AIM II protein fragment (lacking the N-terminus and transmembrane region) is expressed using the following primers:

The 5' oligonucleotide primer has the sequence 5' GCG GGATCCGGAGAGATGGTCACC 3'(SEQ ID NO:7) containing the underlined BamHI restriction site, which includes nucleotides 244–258 of the AIM II protein coding sequence in FIG. 1A (SEQ ID NO:1).

The 3' primer has the sequence 5' CGC AAGCTTCCTTCACACCATGAAAGC 3' (SEQ ID NO:8) containing the underlined Hind III restriction site followed by nucleotides complementary to nucleotides 757–774 as shown in FIG. 1B (SEQ ID NO:1).

The entire AIM II protein can be expressed using the following primers:

The 5' oligonucleotide primer has the sequence 5' GACC GGATCCATG GAG GAG AGT GTC GTA CGG C 3' (SEQ ID NO:9) containing the underlined Bam HI restriction site, which includes nucleotides 49–70 of the AIM II protein coding sequence in FIG. 1A (SEQ ID NO:1).

The 3'primer has the sequence 5° CGC AAGCTTCCT TCA CAC CAT GAA AGC 3' (SEQ ID NO:10) containing the underlined HindIII restriction site followed by nucleotides complementary to nucleotides 756–783 as shown in FIG. 1B (SEQ ID NO:1).

The restriction sites are convenient to restriction enzyme sites in the bacterial expression vector pQE9, which are used for bacterial expression in these examples. (Qiagen, Inc. 9259 Eton Avenue, Chatsworth, Calif., 91311). pQE9 encodes ampicillin antibiotic resistance ("Amp") and contains a bacterial origin of replication ("ori"), an IPTG inducible promoter, a ribosome binding site ("RBS"), a 6-His tag and restriction enzyme sites.

The amplified AIM II DNA and the vector pQE9 both are digested with BamHI and Hind III and the digested DNAs are then ligated together. Insertion of the AIM II protein DNA into the restricted pQE9 vector places the AIM II protein coding region downstream of and operably linked to the vector's IPTG-inducible promoter and in-frame with an initiating AUG appropriately positioned for translation of AIM II protein.

B. Expression of AIM II with a C-terminal 6-His tag

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the carboxyl terminus of that polypeptide.

The DNA sequence encoding the desired portion of the AIM II protein is amplified from the deposited cDNA clone using PCR oligonucleotide primers which anneal to the amino terminal sequences of the desired portion of the AIM II protein and to sequences in the deposited construct 3' to the cDNA coding sequence. Additional nucleotides containing restriction sites to facilitate cloning in the pQE60 vector are added to the 5' and 3' sequences, respectively.

For cloning the protein, the 5' primer has the sequence 5' GACGC CCATGGAG GAG GAG AGT GTC GTA CGG C 3' (SEQ ID NO:17) containing the underlined NcoI restriction site followed by nucleotides complementary to the amino terminal coding sequence of the AIM II sequence in FIG. 1A. One of ordinary skill in the art would appreciate, of course, that the point in the protein coding sequence where the 5' primer begins may be varied to amplify a DNA segment encoding any desired portion of the complete protein (shorter or longer). The 3' primer has the sequence 5' GACC GGATCC CAC CAT GAA AGC CCC GAA GTA AG 3' (SEQ ID NO:18) containing the underlined BamHI restriction site followed by nucleotides complementary to the 3' end of the coding sequence immediately before the stop codon in the AIM II DNA sequence in FIG. 1B, with the coding sequence aligned with the restriction site so as to maintain its reading frame with that of the six His codons in the pQE60 vector.

The amplified AIM II DNA fragment and the vector pQE60 are digested with BamHI and Nco I and the digested DNAs are then ligated together. Insertion of the AIM II DNA into the restricted pQE60 vector places the AIM II protein coding region downstream from the IPTG-inducible promoter and in-frame with an initiating AUG and the six histidine codons.

C. Expression of AIM II deletion mutant with an N-terminal 6-His tag

The DNA sequence encoding the AIM II protein in the deposited cDNA clone was amplified using PCR oligonucleotide primers specific to sequences of the AIM II protein and to vector sequences 3' to the gene. Additional nucleotides containing restriction sites to facilitate cloning were added to the 5' and 3' sequences respectively.

In particular, an N-terminal deletion AIM II mutant (Met (68) to Val(240) in SEQ ID NO:2) was constructed using the following primers:

The 5' oligonucleotide primer has the sequence 5'-GGG GGA TCC ATG GTC ACC CGC CTG CC-3' (SEQ ID NO:21) containing the underlined BamHI restriction site, and includes 17 nucleotides of the AIM II protein coding sequence in FIG. 1A (SEQ ID NO:1).

The 3' primer has the sequence 5'-GGG AAG CTT CAC CAT GAA AGC CCC G-3' (SEQ ID NO:22) containing the underlined Hind III restriction site followed by nucleotides complentary to nucleotides 753–768 as shown in FIG. 1B (SEQ ID NO:1).

These restriction sites are convenient to restriction enzyme sites in the bacterial expression vector pQE9, which are used for bacterial expression in this example. (Qiagen, Inc. 9259 Eton Avenue, Chatsworth, Calif., 91311). pQE9 encodes ampicillin antibiotic resistance ("Amp$^r$") and contains a bacterial origin of replication ("ori"), an IPTG inducible promoter, a ribosome binding site ("RBS"), a 6-His tag and restriction enzyme sites.

The amplified AIM II (aa 68–240) DNA and the vector pQE9 both were digested with BamHI and Hind III and the digested DNAs were then ligated together. Insertion of the AIM II (aa 68–240) protein DNA into the restricted pQE9 vector places the AIM II protein coding region downstream of and operably linked to the vector's IPTG-inducible promoter and in-frame with an initiating AUG appropriately positioned for translation of AIM II deletion protein.

Transformation of the Bacteria

The ligation mixture from the 6-His tagged expression constructs made in A, B or C, above, is transformed into competent *E. coli* cells using standard procedures. Such procedures are described in Sambrook et al., Molecular Cloning: a Laboratory Manual, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kanr"), is used in carrying out the illustrative example described herein. This strain, which is only one of many that are suitable for expressing AIM II protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 μg/ml) and kanamycin (25 μg/ml).

The ON culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2×phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2×PBS at a concentration of 95 μg/ml.

D. Expression and Purification of full length AIM II without an 6-His tag

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("YAmp") and contains a bacterial origin of replication ("ori"), an IPTG inducible promoter, a ribosome binding site ("RB S"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6×His tag") covalently linked to the carboxyl terminus of that polypeptide. However, in this example, the polypeptide coding sequence is inserted such that translation of the six His codons is prevented and, therefore, the polypeptide is produced with no 6×His tag.

The DNA sequence encoding the desired portion of the AIM II protein is amplified from the deposited cDNA clone using PCR oligonucleotide primers which anneal to the amino terminal sequences of the desired portion of the AIM II protein and to sequences in the deposited construct 3' to the cDNA coding sequence. Additional nucleotides containing restriction sites to facilitate cloning in the pQE60 vector are added to the 5' and 3' sequences, respectively.

For cloning the protein, the 5' primer has the sequence 5' GACGC CCATGGAG GAG GAG AGT GTC GTA CGG C 3' (SEQ ID NO:17) containing the underlined NcoI restriction site including nucleotides of the amino terminal coding region of the AIM II sequence in FIG. 1A. One of ordinary skill in the art would appreciate, of course, that the point in the protein coding sequence where the 5' primer begins may be varied to amplify a desired portion of the complete protein (i.e., shorter or longer). The 3' primer has the sequence 5' CGC AAGCTTCCTT CAC ACC ATG AAA GC 3' (SEQ ID NO:19) containing the underlined Hind III restriction site followed by nucleotides complementary to the 3' end of the non-coding sequence in the AIM II DNA sequence in FIG. 1B (SEQ ID NO:1).

The amplified AIM II DNA fragments and the vector pQE60 are digested with NcoI and Hind III and the digested DNAs are then ligated together. Insertion of the AIM II DNA into the restricted pQE60 vector places the AIM II protein coding region including its associated stop codon downstream from the IPTG-inducible promoter and in-frame with an initiating AUG. The associated stop codon prevents translation of the six histidine codons downstream of the insertion point.

E. Construction of an N-terminal AIM II Deletion Mutant

For cloning an AIM II deletion mutant (Met(68) to Val(240) in SEQ ID NO:2), the 5' primer has the sequence 5'-GGG CCA TGGATG GTC ACC CGC CTG CC-3' (SEQ ID NO:23) containing the underlined NcoI restriction site, and includes followed by 17 nucleotides of the AIM II protein coding sequence in FIG. 1A. The 3' primer has the sequence 5'-GGG AAG CTT CAC CAT GAA AGC CCC G-3' (SEQ ID NO:22) containing the underlined Hind III restriction site followed by nucleotides complementary to nucleotides 753 to 768 in FIG. 1B (SEQ ID NO:1).

The amplified AIM II (aa 68–240) DNA fragments and the vector pQE60 were digested with NcoI and Hind III and the digested DNAs were then ligated together. Insertion of the AIM II (aa 68–240) DNA into the restricted pQE60 vector places the AIM II (aa 68–240) protein coding region downstream from the IPTG-inducible promoter and in-frame with an initiating AUG. The HindIII digestion removes the six histidine codons downstream of the insertion point.

F. Construction of an N-terminal AIM II Deletion Mutant

For cloning an AIM II deletion mutant (Ala(101) to Val(240) in SEQ ID NO:2), the 5' primer has the sequence 5'-GGG CCA TGGGCC AAC TCC AGC TTG ACC-3' (SEQ ID NO:24) containing the underlined NcoI restriction site including nucleotides 349–366 in the AIM II protein coding sequence in FIG. 1A. One of ordinary skill in the art would appreciate, of course, that the point in the protein coding sequence where the 5' primer begins may be varied to amplify a desired portion of the complete protein (i.e., shorter or longer). The 3' primer has the sequence 5'-GGG AAG CTTCAC CAT GAA AGC CCC G-3' (SEQ ID NO:22) containing the underlined Hind III restriction site followed by nucleotides complementary nucleotides 755–768 of the AIM II DNA sequence in FIG. 1B.

The amplified AIM II (aa 101–240) DNA fragments and the vector pQE60 were digested with NcoI and Hind III and the digested DNAs are then ligated together. Insertion of the AIM II (aa 101–240) DNA into the restricted pQE60 vector places the AIM II (aa 101–240) protein coding region downstream from the IPTG-inducible promoter and in-frame with an initiating AUG. The HindIII digestion removes the six histidine codons downstream of the insertion point.

Transformation of the Bacteria

The ligation mixture from expression constructs made in D, E or F, above were transformed into competent *E. coli* cells using standard procedures such as those described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan"), was used in carrying out the illustrative example described herein. This strain, which was only one of many that are suitable for expressing AIM II protein, was available commercially from QIAGEN, Inc., supra. Transformants were identified by their ability to grow on LB plates in the presence of ampicillin and kanamycin. Plasmid DNA was isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture was used to inoculate a large culture, at a dilution of approximately 1:25 to 1:250. The cells were grown to an optical density at 600 nm ("OD600") of between 0.4 and 0.6. Isopropyl-b-D-thiogalactopyranoside ("IPTG") was then added to a final concentration of 1 mM to induce transcription from the lac repressor sensitive promoter, by inactivating the lacI repressor. Cells subsequently were incubated further for 3 to 4 hours. Cells then were harvested by centrifugation.

The cells were then stirred for 3–4 hours at 4° C. in 6M guanidine-HCl, pH8. The cell debris was removed by centrifugation, and the supernatant containing the AIM II was dialyzed against 50 mM Na-acetate buffer pH6, supplemented with 200 mM NaCl. Alternatively, the protein can be successfully refolded by dialyzing it against 500 mM NaCl, 20% glycerol, 25 mM Tris/HCl pH7.4, containing protease inhibitors. After renaturation the protein can be purified by ion exchange, hydrophobic interaction and size exclusion chromatography. Alternatively, an affinity chromatography step such as an antibody column can be used to obtain pure AIM II protein. The purified protein is stored at 4° C. or frozen at −80° C.

Example 2:

Cloning and Expression of AIM II protein in a Baculovirus Expression System

A. Construction of a Full Length AIMII Protein

The cDNA sequence encoding the full length AIM II protein in the deposited clone is amplified using PCR oligonucleotide primers corresponding to the 5' and 3' sequences of the gene:

The 5 ' primer has the sequence 5 'GCT CCA GGA TCCGCC ATC ATG GAG GAG AGT GTC GTA CGG C 3' (SEQ ID NO:11) containing the underlined Bam HI restriction enzyme site followed by 22 bases (i.e., nucleotides 49–70) of the coding region for the AIM II protein in FIG. 1A. Inserted into an expression vector, as described below, the 5' end of the amplified fragment encoding AIM II provides an efficient signal peptide. An efficient signal for initiation of translation in eukaryotic cells, as described by Kozak, M., *J. Mol Biol.* 196:947–950 (1987) is appropriately located in the vector portion of the construct.

The 3' primer has the sequence 5' GA CGC GGT ACC GTC CAA TGC ACC ACG CTC CTT CCT TC 3' (SEQ ID NO:12) containing the underlined Asp 718 restriction site followed by nucleotides complementary to 770–795 nucleotides of the AIM II set out in FIG. 1A.

The amplified fragment is isolated from a 1% agarose gel using a commercially available kit ("Geneclean,"BIO 101 Inc., La Jolla, Calif.). The fragment then is digested with Bam HI and Asp 718 and again is purified on a 1% agarose gel. This fragment is designated herein F2.

The vector pA2-GP is used to express the AIM II protein in the baculovirus expression system, using standard methods, as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamHI site. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170: 31–39, among others.

The plasmid is digested with the restriction enzyme Bam HI and Asp 718 and then is dephosphorylated using calf intestinal phosphatase, using routine procedures known in the art. The DNA is then isolated from a 1% agarose gel using a commercially available kit ("Geneclean"BIO 101 Inc., La Jolla, Calif.). This vector DNA is designated herein "V".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human AIM II gene by digesting DNA from individual colonies using XbaI and then analyzing the digestion product by gel electrophoresis. The sequence of the cloned fragment is confirmed by DNA sequencing. This plasmid is designated herein pBacAIM II.

B. Construction of an N-terminal AIM II deletion mutants

In this illustrative example, the plasmid shuttle vector pA2 GP was used to insert the cloned DNA encoding the an N-terminal deletion of the AIM II protein into a baculovirus to express an AIM II mutant (Gln(60) to Val(240)) and AIM II mutant (Ser(79) to Val(240)) in SEQ ID NO:2, using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding the AIM II (Gln(60)to Val(240), FIG. 1A (SEQ ID NO:2), was amplified using PCR oligonucleotide primers corresponding to the 5' and 3' sequences of the gene.

The 5' primer has the sequence 5'-GGG <u>GGA TCC</u>COCA GCT GCA CTG GCG TCT AGG-3' (SEQ ID NO:25) containing the underlined BamHI restriction enzyme site followed by 20 nucleotides (i.e., nucleotides 225–245) encoding the AIM II protein shown in FIGS. 1A and B, beginning with amino acid 60 of the protein. The 3' primer has the sequence 5'-GGG <u>TCT AGA</u> CAC CAT GAA AGC CCC G-3' (SEQ ID NO:26) containing the underlined XbaI restriction site followed by nucleotides complementary to nucleotides 753–768 in FIG. 1B (SEQ ID NO:1).

The amplified fragment was isolated from a 1% agarose gel using a commercially available kit ("Geneclean," BIO 101 Inc., La Jolla, Calif.). The fragment then was digested with BamHI and XbaI and again was purified on a 1% agarose gel. This fragment was designated herein "F1".

The plasmid was digested with the restriction enzymes BamHII and XbaI and optionally, can be dephosphorylated using calf intestinal phosphatase, using routine procedures known in the art. The DNA was then isolated from a 1% agarose gel using a commercially available kit ("Geneclean" BIO 101 Inc., La Jolla, Calif.). This vector DNA was designated herein "V1".

Fragment F1 and the dephosphorylated plasmid V1 were ligated together with T4 DNA ligase. *E. coli* HB101 or other suitable *E. coli* hosts such as XL-1 Blue (Stratagene Cloning Systems, La Jolla, Calif.) cells were transformed with the ligation mixture and spread on culture plates. Bacteria were identified that contain the plasmid with the human AIM II gene using the PCR method, in which one of the primers that was used to amplify the gene and the second primer was from well within the vector so that only those bacterial colonies containing the AIM II gene fragment will show amplification of the DNA. The sequence of the cloned fragment was confirmed by DNA sequencing. This plasmid was designated herein pBacAIM II (aa 60–240).

The cDNA sequence encoding the AIM II (Ser(79)to Val(240), FIG. 1A (SEQ ID NO:2), was amplified using PCR oligonucleotide primers corresponding to the 5' and 3' sequences of the gene.

The 5' primer has the sequence 5' cgc <u>GGATCCC</u> TCCTGGGAGCAGCTGATAC 3' (SEQ ID NO:27) containing the underlined BamHI restriction enzyme site followed by nucleotides 283–301 encoding the AIM II protein shown in FIGS. 1A and B, beginning with amino acid 79 of the protein. The 3' primer has the sequence 5'-cgc <u>GGATCC</u>TCA CACCATGAAAGC 3' (SEQ ID NO:29)

containing the underlined BamHI restriction site followed by nucleotides complementary to nucleotides 757–771 in FIG. 1B (SEQ ID NO:1).

The amplified fragment was isolated from a 1% agarose gel using a commercially available kit ("Geneclean," BIO 101 Inc., La Jolla, Calif.). The fragment then was digested with BamHI and again was purified on a 1% agarose gel. This fragment was designated herein "F1".

The plasmid was digested with the restriction enzymes BamHI and optionally, can be dephosphorylated using calf intestinal phosphatase, using routine procedures known in the art. The DNA was then isolated from a 1% agarose gel using a commercially available kit ("Geneclean" BIO 101 Inc., La Jolla, Calif.). This vector DNA was designated herein "V1".

Fragment F1 and the dephosphorylated plasmid V1 were ligated together with T4 DNA ligase. *E. coli* HB101 or other suitable *E. coli* hosts such as XL-1 Blue (Stratagene Cloning Systems, La Jolla, Calif.) cells were transformed with the ligation mixture and spread on culture plates. Bacteria were identified that contain the plasmid with the mutant AIM II gene using the PCR method, in which one of the primers that was used to amplify the gene and the second primer was from well within the vector so that only those bacterial colonies containing the AIM II gene fragment will show amplification of the DNA. The sequence of the cloned fragment was confirmed by DNA sequencing. This plasmid was designated herein pBacAIM II (aa 79–240).

C. Transfection of the Baculovirus vectors containing AIM II sequences

5 µg of the plasmid either pBac AIM II or pBacAIM II (aa 60–240) was co-transfected with 1.0 µg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84: 7413–7417 (1987). 1 µg of BaculoGold™ virus DNA and 5 µg of the plasmid pBac AIM II or pBacAIM II (aa 60–240) was mixed in a sterile well of a microtiter plate containing 50 µl of serum-free Grace's medium (Life Technologies Inc., Gaithersburg, MD). Afterwards 10 µl Lipofectin plus 90 µl Grace's medium were added, mixed and incubated for 15 minutes at room temperature. Then the transfection mixture was added drop-wise to Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum is added. The plate was put back into an incubator and cultivation was continued at 27° C. for four days.

After four days the supernatant was collected and a plaque assay was performed, as described by Summers and Smith, cited above. An agarose gel with "Blue Gal" (Life Technologies Inc., Gaithersburg) was used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus was added to the cells. After appropriate incubation, blue stained plaques are picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus is used to infect Sf9 cells seeded in 35 mm dishes. Four days later the supernatants of these culture dishes were harvested and then they were stored at 4° C. A clone containing properly inserted HESSB I, II and III was identified by DNA analysis including restriction mapping and sequencing. This was designated herein as V-AIM II or V-AIM II (aa 60–240).

Sf9 cells were grown in Grace's medium supplemented with 10% heat-inactivated FBS. The cells were infected with the recombinant baculovirus V-AIM II or V-AIM II (aa60–240) at a multiplicity of infection ("MOI") of about 2 (about 1 to about 3). Six hours later the medium was removed and was replaced with SF900 II medium minus methionine and cysteine (available from Life Technologies Inc., Gaithersburg). 42 hours later, 5 µCi of $^{35}$S-methionine and 5 µCi $^{35}$S-cysteine (available from Amersham) were added. The cells were further incubated for 16 hours and then they were harvested by centrifugation, lysed and the labeled proteins were visualized by SDS-PAGE and autoradiography.

Example 3:

Cloning and Expression in Mammalian Cells

Most of the vectors used for the transient expression of the AIM II protein gene sequence in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of trancription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283, H9 and Jurkart cells, mouse NIH3T3 and C127 cells, Cos 1, Cos 7 and CV1, African green monkey cells, quail QC 1–3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., *Biochem J* 227:277–279 (1991); Bebbington et al.,

*Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pAIM II HA, is made by cloning a cDNA encoding AIM II into the expression vector pcDNAI/Amp (which can be obtained from Invitrogen, Inc.).

The expression vector pcDNAI/amp contains: (1) an *E.coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the AIM II protein and an HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37: 767 (1984). The fusion of the HA tag to the target protein allows easy detection of the recombinant protein with an antibody that recognizes the HA epitope.

The plasmid construction strategy is as follows. The AIM II cDNA of the deposited clone is amplified using primers that contain convenient restriction sites, much as described above regarding the construction of expression vectors for expression of AIM II in *E. coli*. To facilitate detection, purification and characterization of the expressed AIM II, one of the primers contains a hemagglutinin tag ("HA tag") as described above.

Suitable primers include the following, which are used in this example. The 5' primer, containing the underlined BamHI site, and an AUG start codon has the following sequence:

(SEQ ID NO:13)
5' GAG CTC <u>GGATCC</u> GCC ATC ATG GAG GAG

AGT GTC GTA CGGC 3'.

The 3' primer, containing the underlined Xba I site, a stop codon, 9 codons thereafter forming the hemagglutinin HA tag, and 33 bp of 3' coding sequence (at the 3' end) has the following sequence:

(SEQ ID NO:14)
5'GAT GT<u>T CTA GAA</u> AGC GTA GTC TGG GAC GTC
GTA TGG GTA CAC CAT GAA AGC CCC GAA GTA AGA
CCG GGT AC3'.

The PCR amplified DNA fragment and the vector, pcDNAI/Amp, are digested with HindIII and XhoI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the AIM II-encoding fragment.

For expression of recombinant AIM II, COS cells are transfected with an expression vector, as described above, using DEAE-DEXTRAN, as described, for instance, in Sambrook et al., Molecular Cloning: a Laboratory Manual, Cold Spring Laboratory Press, Cold Spring Harbor, N.Y. (1989). Cells are incubated under conditions for expression of AIM II by the vector.

Expression of the AIM II HA fusion protein is detected by radiolabelling and immunoprecipitation, using methods described in, for example Harlow et al., Antibodies: A Laboratory Manual, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 3(b)

Cloning and Expression in CHO Cells

The vector pC4 is used for the expression of AIM II protein. Plasmid pC 1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M.J. and Sydenham, M.A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC4 contains for expressing the gene of interest the strong promoter of the long terminal repeat (LTR) of the Rous Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are Bam HI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the AIM II in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and Asp 718 and then dephosphorylated using calf intestinal phosphatase by procedures known in the art. The vector is then isolated from a 1% agarose gel.

The DNA sequence encoding the complete AIM II protein is amplified using PCR oligonucleotide primers corresponding to the 5' and 3' sequences of the gene. The 5' primer has the sequence 5'GCTCCA GGATCCGCC ATC ATG GAG GAG AGT GTC GTA CGG C3' (SEQ ID NO:15) containing the underlined Bam HI restriction enzyme site followed by an efficient signal for initiation of translation in eukaryotes, as described by Kozak, M., *J. Mol. Biol.* 196:947–950 (1987), and 22 bases (i.e., nucleotides 49–70) of the coding region of the AIM II protein shown in FIG. 1A (SEQ ID NO:1). The 3' primer has the sequence 5'GA CGC GGT ACCGTC CAA TGC ACC ACG CTC CTT CCT TC 3' (SEQ ID NO:16) containing the underlined Asp 718 restriction site followed by nucleotides complementary to nucleotides 770–795 of the AIM II gene shown in FIG. 1B (SEQ ID NO:1).

The amplified fragment is digested with the endonucleases BamHI and Asp718 and then purified again on a 1% agarose gel. The isolated fragment and the dephosphorylated vector are then ligated with T4 DNA ligase. *E. coli* HB11 or XL-1 Blue cells are then transformed and bacteria are identified that contain the fragment inserted into plasmid pC4 using, for instance, restriction enzyme analysis.

Example 3(c)

Cloning and Expression of an AIMII N-terminal Deletion in CHO Cells

The vector pC4 was used for the expression of AIM II mutant (Met(68)-Val (240) in SEQ ID NO:2) protein. The plasmid pC4 was digested with the restriction enzymes Bam HI and then dephosphorylated using calf intestinal phosphatase by procedures known in the art. The vector was then isolated from a 1% agarose gel.

The DNA sequence encoding the AIM II (aa 68–240) protein was amplified using PCR oligonucleotide primers corresponding to the 5' and 3' sequences of the gene. The following 5' primer was used: 5' GAC AGT GGA TCC GCC ACC ATG GTC ACC CGC CTG CCT GAC GGA C 3' (SEQ ID NO: 40) containing the underlined Bam HI restriction enzyme site followed by an efficient signal for initiation of translation in eukaryotes, as described by Kozak, M., *J. Mol. Biol.* 196:947–950 (1987), and nucleotides 202–226 in the coding region for the AIM II polypeptide shown in FIG. 1A (SEQ ID NO:1). The following 3' primer was used: (Bam HI +stop codon (italics)) 5'-GGG GGATCCTGA CAC CAT GAA AGC CCC G-3' (SEQ ID NO:28) containing the underlined BamHI restriction site followed by nucleotides complementary nt 753–768 shown in FIG. 1B (SEQ ID NO:1).

The amplified fragment was digested with the endonucleases BamHII and then purified again on a 1% agarose gel. The isolated fragment and the dephosphorylated vector were then ligated with T4 DNA ligase. *E. coli* HB101 or XL-1 Blue cells were then transformed and bacteria were identified that contain the fragment inserted into plasmid pC4 using, for instance, restriction enzyme analysis.

The vector pC4/Ckβ8 (a pC4 construct wherein the Ckβ8 signal peptide was first cloned into the pC4 vector with a Bam HI site at the 3' end of CKβ8 signal sequence) was used for the expression of AIM II mutant (Trp(80)-Val (240) in SEQ ID NO:2) protein. The plasmid pC4/Kβ8 was digested with the restriction enzymes BamHI and then dephosphorylated using calf intestinal phosphatase by procedures known in the art. The vector was then isolated from a 1% agarose gel.

The DNA sequence encoding the AIM II (aa 80–240) protein was amplified using PCR oligonucleotide primers corresponding to the 5' and 3' sequences of the gene. The following 5' primer was used: 5' cgc GGATCCTGGGAGCAGCTGATAC 3' (SEQ ID NO:41) containing the underlined BamHI restriction enzyme site followed by nucleotides 286–301 in the coding region for the AIM II polypeptide shown in FIG. 1A (SEQ ID NO:1). The following 3' primer was used: 5' cgc GGATCCTCA CACCATGAAAGC 3' (SEQ ID NO:29) containing the underlined BamHI retriction site followed by nucleotides complementary nt 757–771 shown in FIG. 1B (SEQ ID NO:1).

The amplified fragment was digested with the endonucleases BamHI and then purified again on a 1% agarose gel. The isolated fragment and the dephosphorylated vector were then ligated with T4 DNA ligase. *E. coli* HB101 or XL-1 Blue cells were then transformed and bacteria were identified that contain the fragment inserted into plasmid pC4/Ckβ8 using, for instance, restriction enzyme analysis.

CHO Cell Transfection

Chinese hamster ovary cells lacking an active DHFR gene are used for transfection. 5 μg of the expression pC4 vectors described above are cotransfected with 0.5 μg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM).

Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by SDS-PAGE and Western blot or by reverse phase HPLC analysis.

Example 3(d)

Cloning and Expression of an AIM II-terminal Deletion in CHO Cells

The vector pC4 was used for the expression of AIM II mutant (Met(68)-Val (240) in SEQ ID NO:2) protein that includes a C-terminal Fc immunoglobulin region. In this construct, the Ckβ8 signal peptide was first cloned into pC4 with a Bam HI site at the 3' end of Ckβ8. The Fc fragment flanked by Bam HI and Xba I sites was cloned into the vector resulting in pC4/Ckβ8/Fc. The AIM-II fragment was then cloned between the CK-β8 leader and the Fc fragment in the Bam HI site.

The plasmid pC4 was digested with the restriction enzymes Bam HI and then dephosphorylated using calf intestinal phosphatase by procedures known in the art. The vector was then isolated from a 1% agarose gel.

The DNA sequence encoding the complete AIM II (aa 68–240) protein was amplified using PCR oligonucleotide primers corresponding to the 5' and 3' sequences of the gene. The following 5' primer was used: 5' GAC AGT GGA TCC GCC ACC ATG GTC ACC CGC CTG CCT GAC GGA C 3' (SEQ ID NO:40) containing the underlined Bam HI restriction enzyme site followed by an efficient signal for initiation of translation in eukaryotes, as described by Kozak, M., J. Mol. Biol. 196:947–950 (1987), and nucleotides 202–226 in the coding region for the AIM II polypeptide shown in FIG. 1A (SEQ ID NO:1). The following 3' primer was used: (Bam HI) 5'-GGG GGA TCCCAC CAT GAA AGC CCC G-3' (SEQ ID NO:30) containing the underlined BamHI retriction site followed by nucleotides complementary to nt 753–768 shown in FIGS. 1A and B (SEQ ID NO:1) followed by the Fc immunoglobulin fragment having the following sequence:

(SEQ ID NO:31)
5'-GGGATCCGGAGCCCAAATCTTCTGACAAAACTCACACATGCCCA

CCGTGCCCAGCACCTGAATTCGAGGGTGCACCGTCAGTCTTCCTCT

TCCCCCCAAAACCCAAGGACACCCTCATGATCTCCCGGACTCCTGA

GGTCACATGCGTGGTGGTGGACGTAAGCCACGAAGACCCTGAGGT

CAAGTTCAACTGGTACGTGGACGGCGTGGAGGTGCATAATGCCAA

GACAAAGCCGCGGGAGGAGCAGTACAACAGCACGTACCGTGTGGT

CAGCGTCCTCACCGTCCTGCACCAGGACTGGCTGAATGGCAAGGAG

TACAAGTGCAAGGTCTCCAACAAAGCCCTCCCAACCCCCATCGAGA

AAACCATCTCCAAAGCCAAAGGGCAGCCCCGAGAACCACAGGTGT

ACACCCTGCCCCCATCCCGGGATGAGCTGACCAAGAACCAGGTCA

GCCTGACCTGCCTGGTCAAAGGCTTCTATCCAAGCGACATCGCCGT

GGAGTGGGAGAGCAATGGGCAGCCGGAGAACAACTACAAGACCAC

-continued
GCCTCCCGTGCTGGACTCCGACGGCTCCTTCTTCCTCTACAGCAAG

CTCACCGTGGACAAGAGCAGGTGGCAGCAGGGGAACGTCTTCTCA

TGCTCCGTGATGCATGAGGCTCTGCACAACCACTACACGCAGAAGA

GCCTCTCCCTGTCTCCGGGTAAATGAGTGCGACGGCCGCGAC<u>TCTA

GA</u>GGAT-3'.

The amplified fragment was digested with the endonucleases BamHI and then purified again on a 1% agarose gel. The isolated fragment and the dephosphorylated vector were then ligated with T4 DNA ligase. E. coli HB101 or XL-1 Blue cells were then transformed and bacteria are identified that contain the fragment inserted into plasmid pC4 using, for instance, restriction enzyme analysis.

CHO Cell Transfection

Chinese hamster ovary (CHO/dhfr-DG44) cells were transfected with the expression vector (pC4/spCKP8/Fc/AIMII) using lipofectin. Recombinant clones were isolated by growing the cells in MEM alpha selective medium with 5% dialyzed fetal bovine serun (DiFBS), 1% penicillin/streptomycin (PS), 1 mg/mL geneticin (G418) and 10nM methotrexate (MTX). High expressing clones, which were confirmed by screening recombinant clones using a BIAcore method (see, below for more details), were then individually amplified by increasing stepwise the concentration of MTX to a final concentration of 100 μM. The high expressing clones were used for the production of AIMII-IgG1 fusion protein in a microcarrier CHO perfusion bioreactor.

CHO.AIM II-IgG1 cells were grown on Cytodex 1 microcarriers (Pharmacia Biotech, Upsala, Sweden) in HGS-CHO-3 medium containing 1% ultra-low IgG FBS. The cells grown in multiple microcarrier spinners were scaled up to a 10L microcarrier perfusion bioreactor. The perfusion bioreactor was operated continuously for 27 days and during that period of time, 90 liters of microcarrier-free supernatants containing AIM II-IgG1 fusion protein were harvested. The supernatants were clarified through a filtration process using 0.2 μm sterile filters and stabilized by adding 5 mM EDTA. The clarified supernatants were loaded onto an affinity column to capture AIMII-IgG1 fusion protein.

Purification of AIMII-IgG1 Fusion Protein

The AIMII-IgGI fusion protein was purified from 15L of CHO conditioned media. The conditioned media was loaded onto a Protein A HyperD (54 mL bed volume, BioSepra) affinity column at a flow rate of 30 mL/min at 10° C. on a BioCad 60 (PerSeptives Biosystems). The column was pre-equilibrated with 25 mM sodium acetate, pH8 and 0.1 M NaCl. After loading, the column was washed with 3 column volumes each of 0.1M sodium citrate, pH5 and 0.1M NaCl and 0.1M sodium citrate, pH 2.8 and 0.1M NaCl. The peak fractions containing AIMII-IgG fusion protein were determined by SDS-PAGE analysis and pooled. The identity of the purified protein was confirmed by N-terminal sequence analysis. The final protein yield was about 9 mg/L condition media.

Example 4:

AIM II Expression Constructs

Full-length constructs (a) pCMVsport: The eukaryotic expression vector pCM-Vsport contains nucleotides encoding the AIM-II ORF from Met(1) to Val(240). The plasmid construction strategy is as follows. The AIM II cDNA of the deposited clone is amplified using primers that contain convenient restriction sites. Suitable primers include the following which are used in this example. The 5′ primer, containing the underlined SalI site, an AUG start codon, nucleotides 51–69 in the coding region of the AIM II polypeptide (SEQ ID NO:1) and has the following sequence:

5′-GGG GTC GAC GCC ATC ATG GAG GAG AGT GTC GTA CGG-3′. (SEQ ID NO:32)

The 3′ primer, containing the underlined NotI site, nucleotides complementary to nucleotides 753–767 in SEQ ID NO:1 and a stop codon and has the following sequence:

5′-GGG GCG GCC GCG CCT TCA CAC CAT GAA AGC CCCG-3′. (SEQ ID NO:33)

The PCR amplified DNA fragment is digested with SalI and NotI and then gel purified. The isolated fragment was then ligated into the SalI and NotI digested vector pCM-Vsport. The ligation mixture is transformed into E. coli and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II, eukaryotic cells such as COS or CHO are transfected with the expression vector, as described above, using DEAE-DEXTRAN as described above in Example 3. Expression of the AIM II recombinant protein is detected by the methods described above in Example 3.

(b) pG1SamEN: The retroviral expression vector pG1SamEN encodes the AIM-II ORF from Met(1) to Val (240). The pG1 vector is described in Morgan, R. A., et al., *Nucl. Acids Res.* 20(6):1293–1299 (1992) and is similar to the LN vector (Miller, A. D. and Rosman, G. J. Biotechniques 7:980–990 (1989)), but has additional cloning sites. The plasmid construction strategy is as follows. The AIM II cDNA of the deposited clone is amplified using primers that contain convenient restriction sites. Suitable primers include the following which are used in this example. The 5′ primer, containing the underlined NotI site, and an AUG start codon, nucleotides 51–69 in the coding region for the AIM II polypeptide (SEQ ID NO:1) has the following sequence:

(SEQ ID NO:34)
5′-GGG GCG GCC GCG CCA TCA TGG AGG AGA GTG TCG TAC GG-3′.

The 3′ primer, containing the underlined SalI site, nucleotides complementary to nucleotides 753–768 in SEQ ID NO:1 and a stop codon has the following sequence:

(SEQ ID NO:35)
5′-GGG GTC GAC GCC TTCA CAC CAT GAA AGC CCC G-3′.

The PCR amplified DNA fragment is digested with SalI and NotI and then gel purified. The isolated fragment was then ligated into the SalI and NotI digested vector. The ligation mixture is transformed into E. coli and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II, eukaryotic cells such as COS or CHO are transfected with the expression vector, as described above, using DEAE-DEXTRAN as described above in Example 3. Expression of the AIM II recombinant protein is detected by the methods described above in Example 3.

2. N-terminal Deletion Constructs (a) pG1/ckβ8: The eukaryotic expression vector encodes the AIM-II mutant (Gln(60) to Val(240) in SEQ ID NO:2) (AIM-2 (aa60–240)) and was secreted under the direction of the human Ck-β8 signal peptide. The pG1 vector is described in Morgan, R. A., et al., *Nucl. Acids Res.* 20(6):1293–1299 (1992) and is similar to the LN vector (Miller, A. D. and Rosman, G. J. Biotechniques 7:980–990 (1989)), but has additional cloning sites. The plasmid construction strategy is as follows. The AIM II cDNA of the deposited clone is amplified using primers that contain convenient restriction sites. Suitable primers include the following which are used in this example. The 5′ primer, containing the underlined NotI site, nucleotides in the coding region for the AIM II polypeptide (SEQ ID NO:1) and an AUG start codon has the following sequence:

5′-GGG GCG GCC GCG CCA TCA TGA AGG TCT CCG TGG CTG (SEQ ID NO:36)
CCC TCT CCT GCC TCA TGC TTG TTA CTG CCC TTG GAT CGC AGG
CAG CTG CAC TGG CGT-3′(Not I +Kozak +CK-β8 leader
(double underline)).

The 3′ primer, containing the underlined SalI site, nucleotides complementary to nucleotides 753–768 in SEQ ID NO:1 and a stop codon has the following sequence:

(SEQ ID NO:37)
5′-GGG GTC GAC TCA CAC CAT GAA AGC CCC G-3′.

The PCR amplified DNA fragment is digested with SalI and NotI and then gel purified. The isolated fragment was then ligated into the SalI and NotI digested vector pG1. The ligation mixture is transformed into E. coli and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II, eukaryotic cells such as COS or CHO are transfected with the expression vector, as described above, using DEAE-DEXTRAN as described above in Example 3. Expression of the AIM II recombinant protein is detected by the methods described above in Example 3.

(b) pHE4: Plasmid pHE4 is a bacterial expression vector containing a strong synthetic promoter with two lac operators. Expression from this promoter is regulated by the presence of a lac repressor, and is induced using IPTG or lactose. The plasmid also contains an efficient ribosomal binding site and a synthetic transcriptional terminator downstream of the AIM II mutant gene. The vector also contains the replication region of pUC plasmids and the kanamycin resistance gene.

The AIM-II N-terminal deletion mutants were constructed according to the following scheme. The AIM II cDNA of the deposited clone is amplified using primers that contain convenient restriction sites. Suitable primers include the following which are used in this example.

For the AIM II (Thr(70) to Val(240)) polypeptide in SEQ ID NO:2, the 5' primer, containing the underlined NdeI site, and an AUG start codon, nucleotides 256–271 in the coding region for the AIM II polypeptide (SEQ ID NO:1) has the following sequence:

5'-cgc CATATGA CCCGCCTGCCTGACG-3'    (SEQ ID NO:42).

For the AIM II (Ser(79) to Val(240)) polypeptide in SEQ ID NO:2, the 5' primer, containing the underlined NdeI site, and an AUG start codon, nucleotides 283–310 in the coding region for the AIM II polypeptide (SEQ ID NO:1) has the following sequence:

5'-cgc CATATGA GC TGGGAGCAGCTGAT
    AC-3'                             (SEQ ID NO:43).

For the AIM II (Ser(103) to Val(240)) polypeptide in SEQ ID NO:2, the 5' primer, containing the underlined NdeI site, and an AUG start codon, nucleotides 355–373 in the coding region for the AIM II polypeptide (SEQ ID NO:1) has the following sequence:

5'-cgc CATATG A GC AGCTTGACCGGC
    AGCG-3'                           (SEQ ID NO:44).

The following 3' primers can be used to construct the aforementioned N-terminal deletions:

The 3' primer, containing the underlined Asp718 site, nucleotides complementary to nucleotides 753–768 in SEQ ID NO:1 and a stop codon has the following sequence:

5'-cgc GGTACCTTA CACCATGAAAGCCC
    CG-3'                             (SEQ ID NO:45).

The PCR amipified DNA fragment is digested with NdeI and Asp718 and then gel purified. The isolated fragment was then ligated into the appropriately digested pHE4 vector. The ligation mixture is transformed into *E. coli* and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II N-terminal deletion, bacterial cells are transfected with the expression vector, as described above in Example 1. Expression of the AIM II recombinant protein is detected by the methods described above in Example 1.

Example 5

Biological Characterization of the AIM II Polypeptide

The following set of experiments provides the biological characterization of the AIM II protein and demonstrates that AIM II has potent anti-tumor activity in vivo and in vitro.

A. AIMII is Highly Expressed in Activated Lymphocytes but not in Cancer Cells

Northern blot analyses demonstrated that the AIM II mRNA is approximately 1.9 kb in length and is expressed predominantly in spleen, brain and peripheral blood cells. AIM II is also detectable to some extent in prostate, testis, ovary, small intestine, placenta, liver, skeletal muscle and lung. AIM II message was not detected in fetal tissues, many endocrine glands and tumor lines of non-hematopoetic and myeloid origin.

RT-PCR assays were performed to investigate expression of AIM II in activated vs. resting PBMC. Fresh PBMC including mixture of T cells, B lymphocytes, NK cells, monocytes and granulocyes express the AIM II mRNA which is consistent with Northern blot analysis. No expression was found in resting PBLs as mixture of T, B and NK cells, Jurkat cells (resting or activated) or K562 cells. Increased expression of AIM II was found in activated PBLs, CD3+, CD4+T-cells, CD8+Tumor infiltrating lymphocytes (TIL), granulocytes, and monocytes. Additional RT-PCR analyses demonstrated the presence of AIM II mRNA in LPS-activated neutrophils and PMA-stimulated U937 cells. Interestingly, expression of AIM II was not detectable in various cancer cell lines derived from breast, prostate or ovary, except in one human breast epithelial-derived, non-tumorigenic cell line MCA-1OA cells. In addition, no expression of AIM II was found from three breast cancer samples examined.

B. Constitutive Expression of AIM II Resulted in Growth Inhibition Under Serum Starvation or Treatment with IFNγ

To investigate the biological function of AIM II, the AIM II gene was stably transduced into human breast carcinoma cell line MDA-MB-231 using a retroviral vector. Expression of the AIM II gene in these cells was confirmed by Northern blot analyses. In addition, MDA-MB-231 cells expressing the drug resistance gene Neo were used as control in this study. No difference in the growth rate in vitro was observed within AIM II transfectants (MDA-MB-231/AIM II) compared with that of the parental cells or vector control transfected cells (MDA-MB-231/Neo), when these cells were cultured in medium containing 10% FBS. However, when the serum concentration was reduced to 1%, there was 80% growth inhibition (FIG.4A) for the MDA-MB-231/AIM II cells, but not for the parental or vector control MDA-MB-231 cells. A dose-dependent growth inhibition with a different amount of serum has also been observed.

Figure 4A:
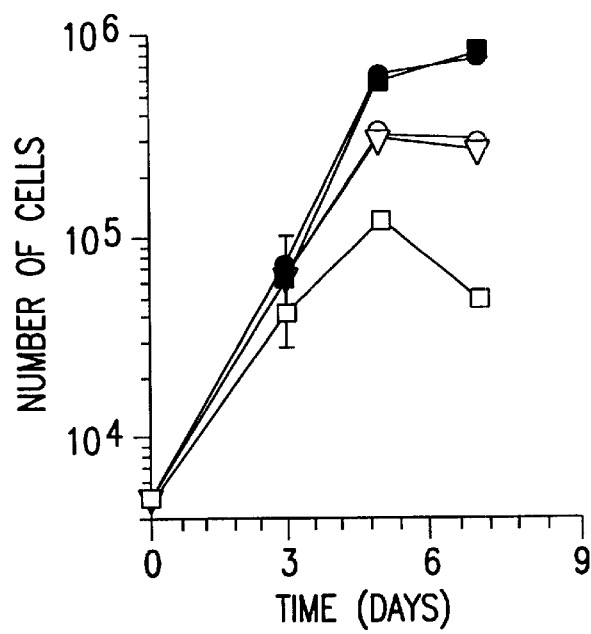
FIGS. 4A and B show the effect of AIMII on the in vitro proliferation of MDA-MB-231 human breast cancer cells. 5,000 MDA-MB-231/WT (circle), MDA-MB-231/Neo (triangle) or MDA-MB-231/AIMII (square) cells were plated in triplicate in 24-well plates with IMEM in the presence of either 10% FBS (filled circle, square or triangle) or 1% FBS (open circle, square or triangle). The number of live cells were determined by trypan blue exclusion method at day 3, day 5 or day 7. Cells were fed with fresh medium every two days during this time course.
Figure 4B:
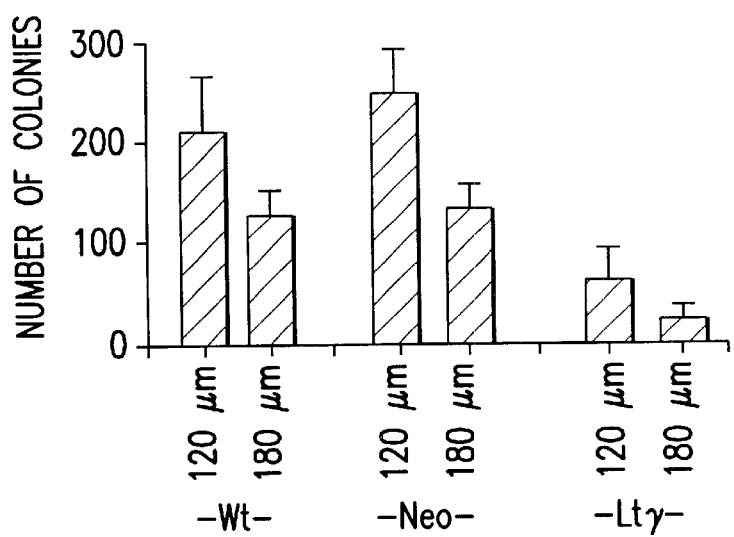
FIG. 4B shows colony formation of MDA-MB-231/WT, MDA-MB-231/Neo and MDA-MB-23/AIMII cells in 0.33% agarose.

Wild type MDA-MB-231 cells grew to a very high density with typical pile-up features in either 10% or 1% serum (FIG. 4A). Morphological changes were noticed in the MDA-MB-231/AIM II cells, with most cells floating into the medium and keeping a single layer growth pattern throughout the culture. No changes of morphology were found in the vector control MDA-MB-231 cells. Growth inhibition of AIM II expressing MDA-MB-231 cells was further examined with in soft agar colony assay. As shown in FIG. 4B, 80% reduction of colony formation was found in the MDA-MB-231/AIM II cells as compared with that of the parental or vector control cells. Treatment with 25 u/ml of IFNγ can also cause 80% growth inhibition of AIM II expressing MDA-MB-231 cells, whereas in the parental or vector control cells, there is only 20–30% inhibition. Thus, AIM II expressing cells demonstrated enhanced sensitivity towards cytotoxicity mediated by cytokine IFNγ.

C. Enhanced apoptosis in AIM II Expressing Cells

Annexin-V FACS analyses were performed to investigate underlying mechanisms of growth inhibition of AIM II expressing cells. In the presence of 10% serum, there are less than 2% apoptotic cells in all three cell lines. After 48 hours incubation in reduced serum (0.5% FBS), the apoptotic population of the MDA-MB-231 cells showed a three-fold increase, up to 8%. There is little or no increase of apoptosis in the parental or vector control MDA-MB-231 cells (FIGS. 5A–C 5A). Induction of apoptosis was further comfirmed by DNA fragmentation assay of MDA-MB-231/WT, MDA-MB-231/Neo and MDA-MB-231/AIM II cells in 10% and 0.5% serum, with or without Paciltaxel (taxol). Fragmented DNA was only seen in the AIM II expressing MDA-MB-231 cells, especially in 1% serum. When AIM II expressing cells were treated with Paclitaxel (taxol), there was much more fragmented DNA observed than seen in parental or vector control cells. Thus, the data suggest that AIM II expression can trigger apoptosis of MDA-MB-231 cells under serum starvation or with the addition of IFNγ or taxol.

D. Potent In Vivo anti-tumor Activities of AIM II

Figure 6A:
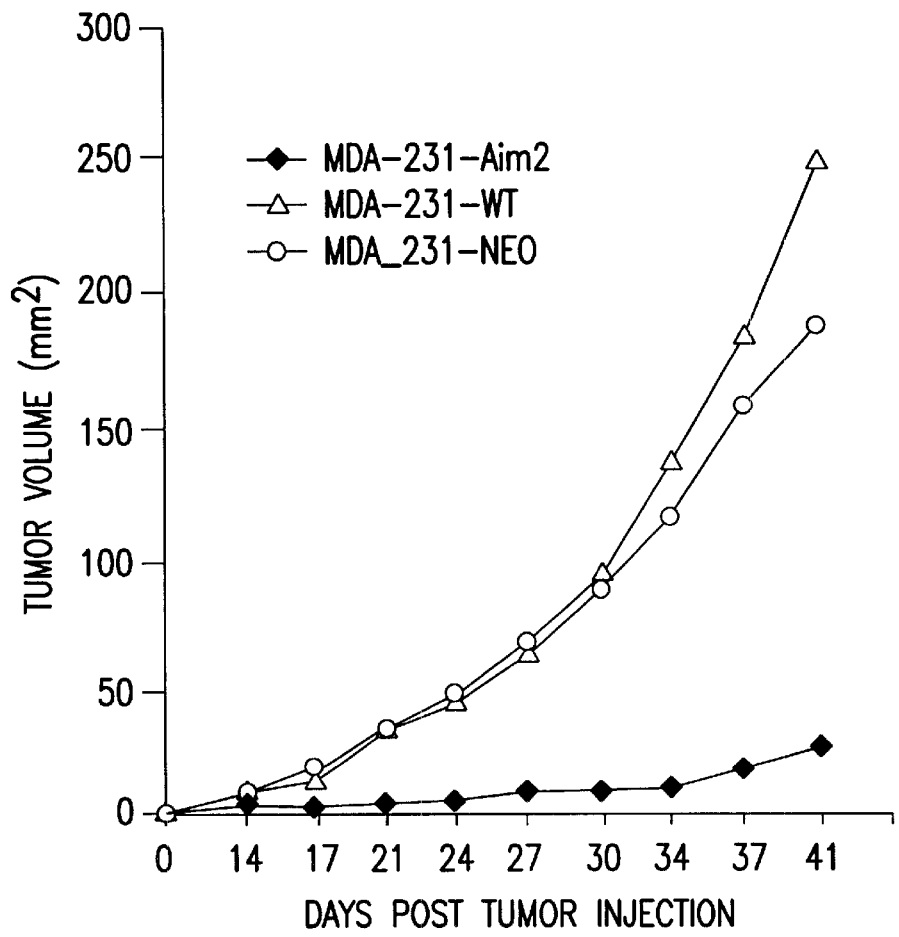
FIG. 6 (A) shows an evaluation of the effects of AIMII on growth of xenograft human breast carcinoma MDA-231 in nude mice. Female athymic nude mice were injected s.c. with $10^6$ cells of parental MDA-231 (MDA-231-WT), or MDA-231 stably transfected with AIMII, or vector control neo (n=10). Mice were then ear tagged and randomized. Tumor growth was assessed twice weekly with a caliper in the blinded fashion. This panel represents three experiments each with ten mice per group. (B) shows the effect of AIMII transduction on inhibition of growth of MC-38 murine colon cancer in syngeneic C57BL/6 mice. Female C57BL/6 mice were injected s.c. with $10^6$ cells of parental MC-38 (MC-38-WT), or MC-38 stably transfected with AIMII, or vector control neo (n=10). Mice were then ear tagged and randomized. Tumor growth was assessed twice weekly with a caliper in a coded, blinded fashion. This panel represents four experiments each with ten mice per group.

We have evaluated the effects of AIM II transduction on the tumor growth in vivo. When MDA-MB-231 cells were inoculated into the mammary fat pads, AIM II expression significantly inhibited tumor formation of MDA-MB-231 in nude mice, whereas the vector control MDA-MB-23/Neo cells showed no change in tumor growth as compared with that of the parental MDA-MB-231 cells (FIG. 6A). Similar tumor suppression in the MDA-MB-231/AIM II cells was also demonstrated in SCID mice. A histological examination of the tumors from AIM II expressing MDA-MB-231 cells or those from parental or vector control cells was performed. Parental or vector control MDA-MB-231 cells formed a large solid tumor mass filled with predominantly tumor cells with little or no cellular infiltrates. In contrast, there was extensive necrosis observed even in small residual tumors formed by the MDA-MB-231/AIM II cells in nude mice. Furthermore, in AIM II expressing tumors, there is an significant increase in number of infiltrating neutrophil cells. The average number of neutrophils (mean ±S.D.) per mm$^2$ tumor size in wild type, Neo control, and AIM II transduced MDA-MB-231 tumors were 101±26, 77±16 and 226±38, respectively, based on the immunohistological staining using Gr-1 mAb (PharMingen, San Diego, Calif.).

Figure 6B:
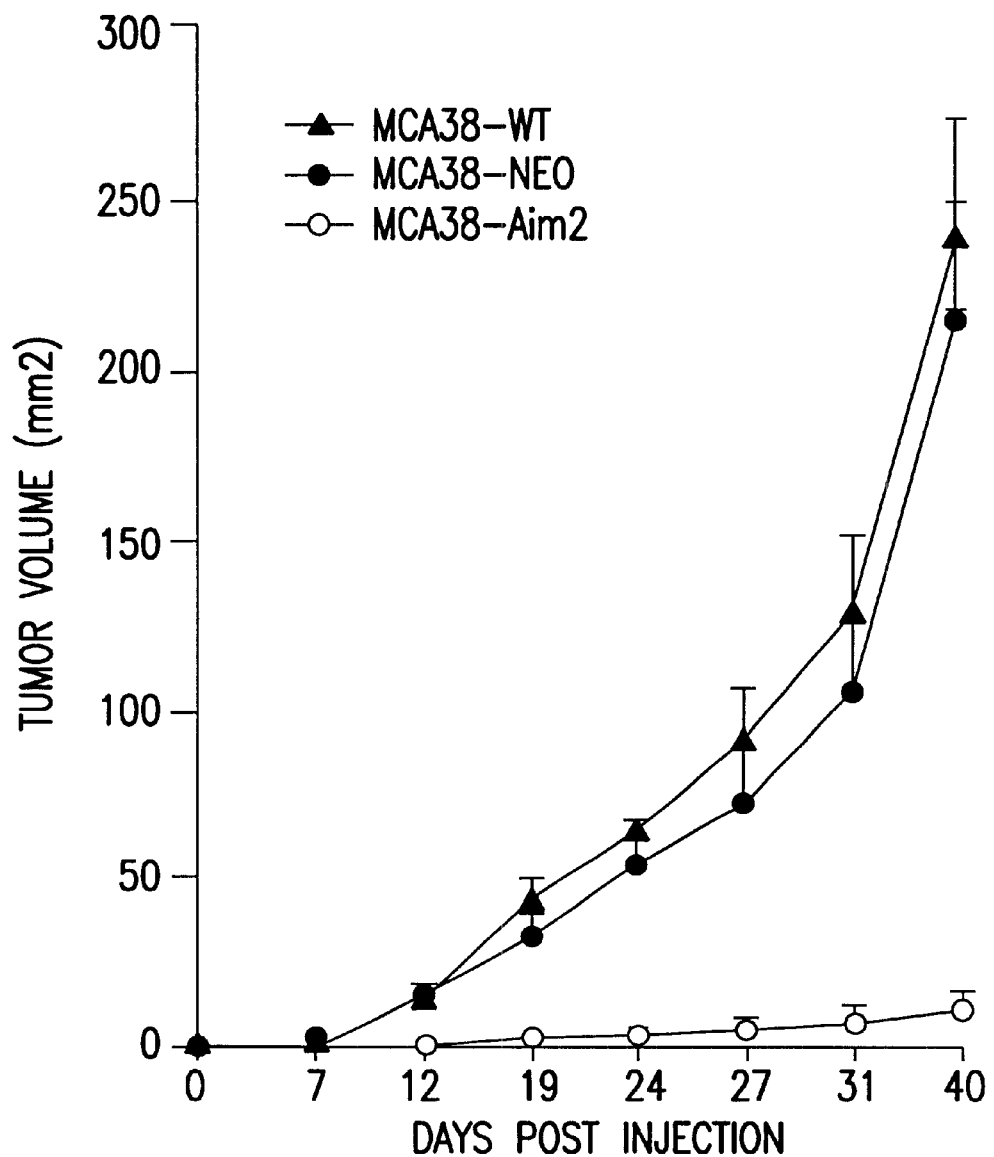

The inhibitory effect of AIM II on tumor suppression was further validated in the syngeneic murine tumor model. Local expression of AIM II in MC-38 murine colon cancer cells resulted in complete suppression of tumor formation in 8 out of 10 C57BL/6 mice (FIG. 6B). Local production of AIM II was also dramatically prolonged the survival of mice bearing MC-38 tumors. All animal experiments were repeated three times and similar results were obtained.

Injection of AIM II-expressing tumor cells did not cause gross abnormalities in the nude mice, SCID mice or C57BL/6 mice, such as weight loss or hepatic injury, during the experimental period. This indicates that locally produced AIM II exerts a potent anti-tumor effect without inducing systemic toxicity.

E. Expression and Cytotoxicity of a Soluble AIM II Protein

In order to study the activities of the AIM II protein, a recombinant soluble form of AIM II protein (sAIM II) was produced by transient transfecting 293T cells with a construct pFlag-AIM II. This construct encodes the extracellular domain of AIM II, but lacking the transmembrane portion of AIM II. (FIG. 7A) A single 20 kDa polypeptide (sAIM II) can be purified from the conditioned medium of pFlag-AIM II transduced 293T cells with anti-Flag monoclonal antibody. (FIG. 7A) The proliferation of breast cancer MDA-MB-231 cells were inhibited in response to the treatment of this soluble AIM II protein, at a dose dependent manner (FIGS. 7B–C). Addition of IFNγ, at 10 u/ml or 50 u/ml, dramatically enhanced cytotoxicity of the soluble AIM II protein. IFNγ alone showed little activity on the MDA-MB-231 cells (FIGS. 7B–C). This is consistent with previous report that MDA-MB-231 cells is resistant to single cytokine such as TNF or IFNγ treatment.

A series of normal and cancer cell lines were tested for their sensitivity to the cytotoxic effects of soluble AIM II protein at sub-optimal concentration (50 ng/ml) in the presence of 10 u/ml of INFγ. As shown in Table 1, cells from MDA-130, MCF-7, HT-29 are sensitive to the cytotoxic effects of AIM II, whereas cells from U93T, MC3-1, SW480, MCF-1OA are resistant to AIM II-mediated cell killing. Among all the cell lines tested, colon adenocarcinoma cell line HT-29 is the most sensitive, with IC$_{50}$ less than 1ng/ml. It has been shown that HT-29 is very sensitive to TNF, Fas or lymphotoxin β receptor mediated killing in the presence of IFNγ.

F. Both LTβ6R and TR2 are required for AIM II Induced Growth Inhibition of Cancer Cells AIM II was originally identified from activated T-cell cDNA library but does not induce apoptosis in the lymphocyte cell lines. Using the RT-PCR analyses, all lymphopoietic cells examined showed no expression of LTβR, but TR2 expression was found in all these cells, especially in activated Jurkat cells or PBLs. This is consistent with the previous reports that peripheral lymphocytes do not express the LTβR, while TR2 expression is associated with T-cell activation.

Figure 8A:
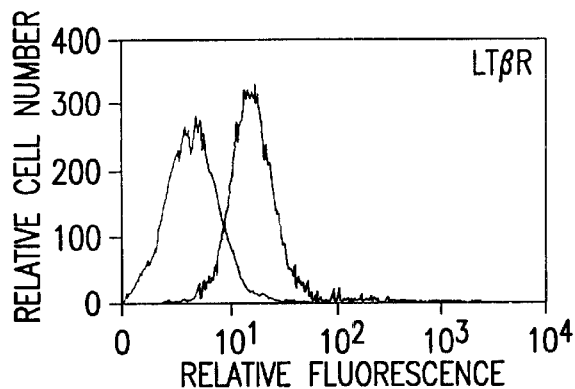
Figure 8B:
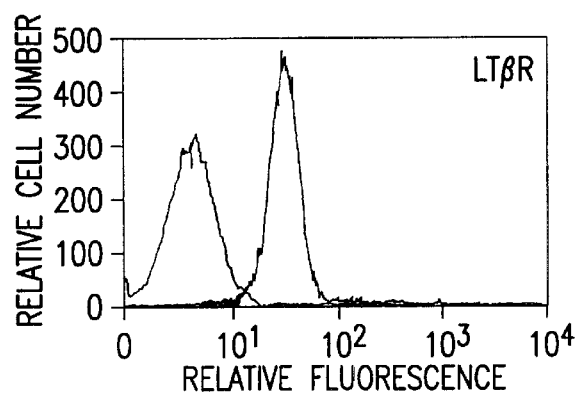
Figure 8C:
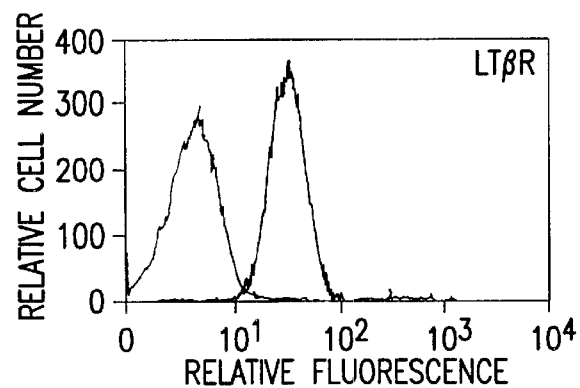
Figure 8D:
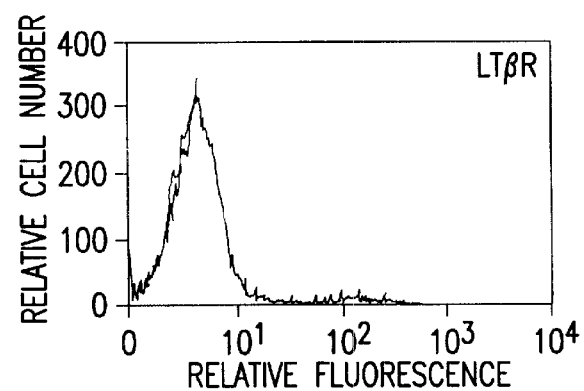
Figure 8E:
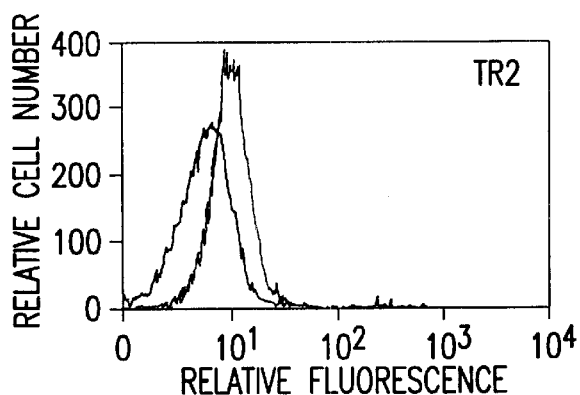
Figure 8F:
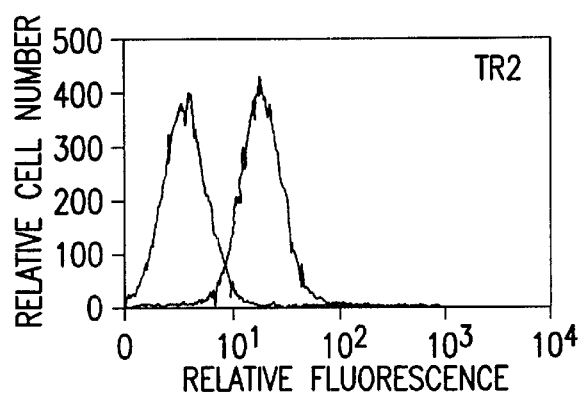
Figure 8G:
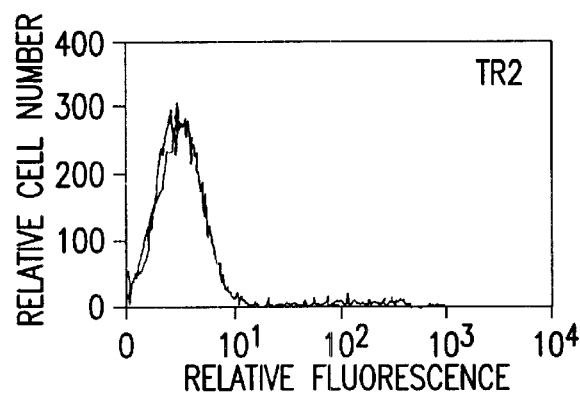
Figure 8H:
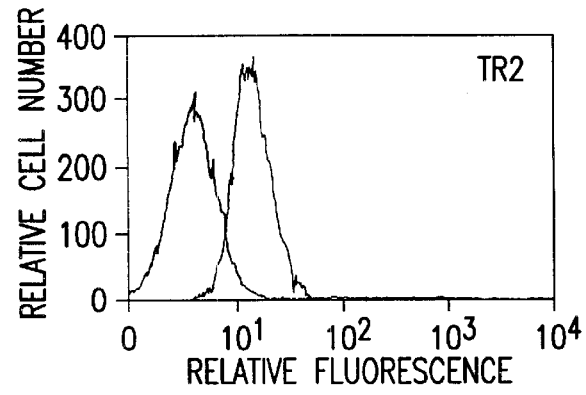

Cell surface expression of the LTβR and TR2 in a series of human cancer cells was examined using monoclonal antibodies against the LTβR or TR2 by FACS analysis. As shown in FIGS. 8A–H, high levels of both receptors were found on the MDA-MB-231, and HT-29 cells, whereas MC3-1 cells do not express TR2 and Jurkat cells do not express LTβR. FIG. 8L summarizes surface expression of both receptors in all the cell lines examined. Cell lines that express only one of the receptors, such as Jurkat or MC3-1 are resistant to the cytotoxicity of AIM II. Taken together, these data suggest that AIM II-mediated growth inhibition in tumor cells may require both LTβR and TR2 receptors, while cells expressing only one of the receptors is not sufficient to mediate cell killing.

Figure 8I:
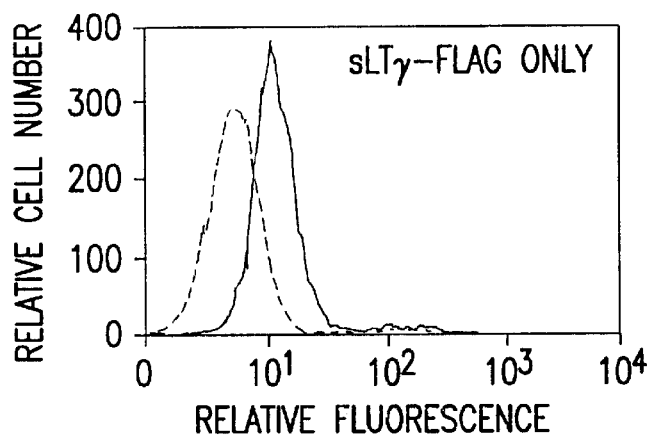
Figure 8J:
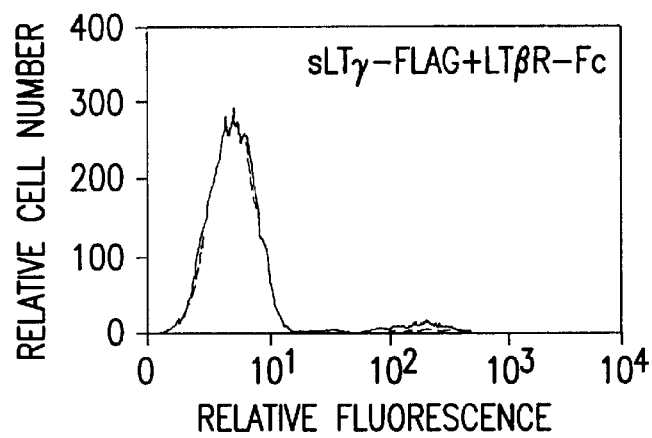
Figure 8K:
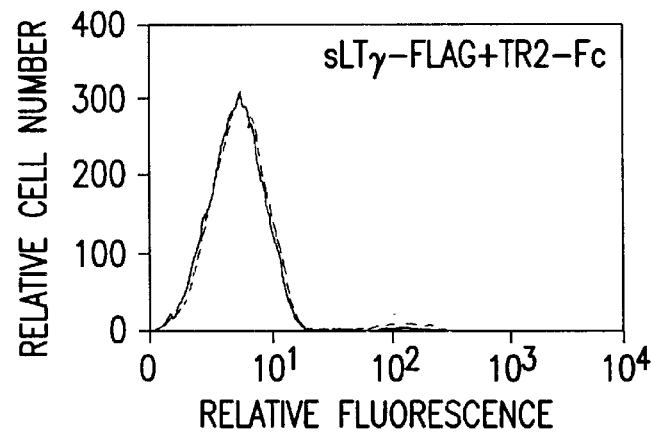

To further demonstrate that the AIM II is a relevant ligand for both LTβR and TR2 receptors and the importance of both receptors in AIM II mediated tumor cell growth inhibition, the Flag-tagged AIM II protein was incubated with MDA-MB-231 or HT-29 cells, then FACS analyses were carried out using anti-Flag mAb. As shown in FIGS. 8I–K, there is a positive shift in binding of MDA-MB-231 or HT-29 cells with Flag-tagged soluble AIM II protein. The specificity of binding was further confirmed by pre-incubation of LTβR-

Fc or TR2-Fc fusion protein with a soluble AIM II-flag protein in the same cells, which effectively blocked binding of both receptors (FIGS. 8B–K).

Figure 8M:
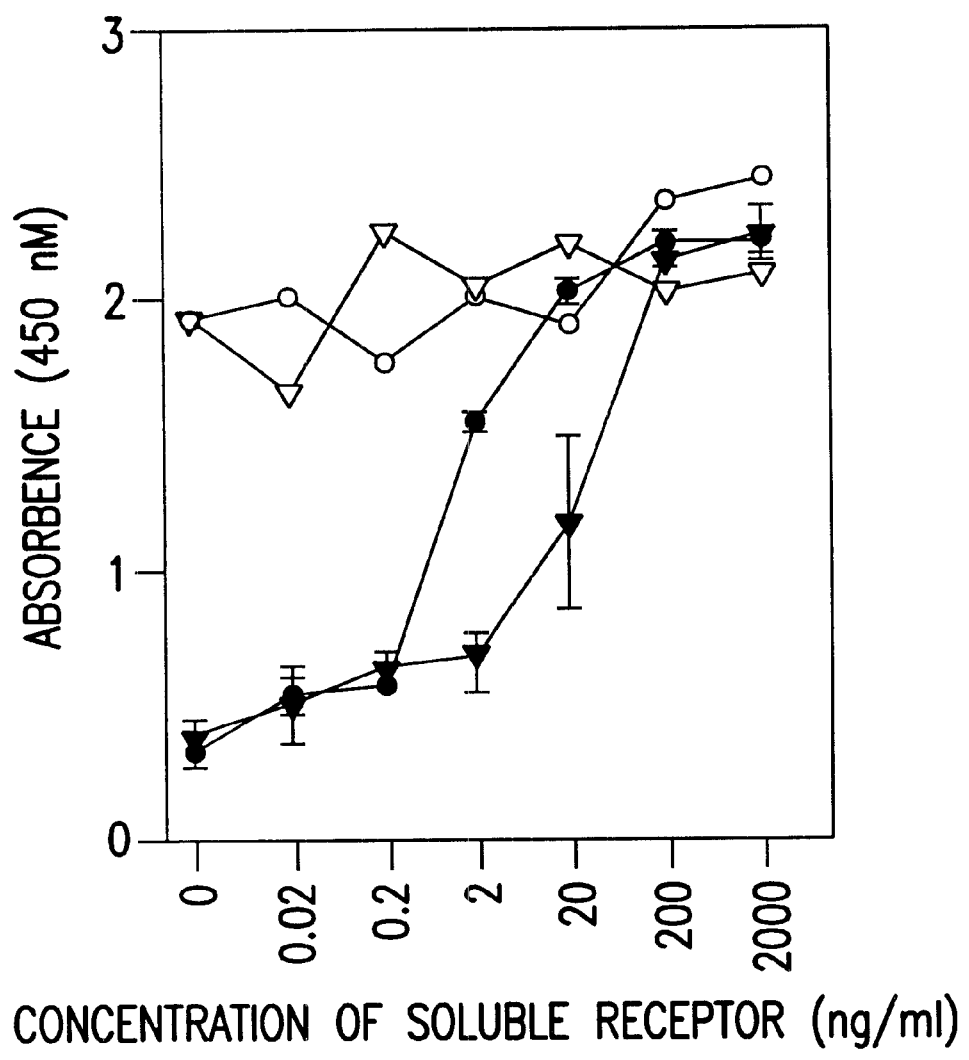

The importance of the involvement of both LTPR and TR2 in the AIM II-mediated cytotoxicity toward tumor cells was further supported by the data obtained from the in vitro growth assays: sAIM II-mediated cytotoxicity of HT-29 was abolished by the addition of LTβR-Fc or TR2-Fc fusion protein in a dose-depended manner whereas the LTβR-Fc or TR2-Fc fusion protein itself showed no effect on cell growth (FIG. 8M). In addition, in a similar assay, sAIM II was unable to bind to other members of TNFR, such as TNFRI, Fas, DR3 or DR14.

In addition, co-culture of MDA-MB-231/Wt or HT-29 cells with MDA-MB-231/AIM II cells resulted in killing of the MDA-MB-231/Wt or wild type HT-29 cells. However, conditioned media collected from the co-cultured MDA-MB-231/AIM II or MC-3 8/AIM II cells showed no inhibitory effect on the in vitro proliferation of HT-29 cells. The results indicated that the natural AIM II protein may not be cleaved and secreted into the medium. Thus, the membrane-bound AIM II is functional in cells which express appropriate surface receptors such as MDA-MB-231 or HT-29. Taken together, this data suggests that the AIM II- mediated growth inihibition of tumor cells may require both LTβR and TR2 receptors, while cells expressing only one of the receptors is not sufficient to mediate cell killing.

G. Effects of AIM II on the Lymphocytes

AIM II was originally identified from an activated T-cell cDNA library but does not induce apoptosis in lymphocyte cell lines. Using RT-PCR analyses, all lymphopoietic cells examined showed no expression of LTβR, but TR2 ws positive in all these cells, especially in activated Jurkat cells or PBLs. This is consistent with previous reports that peripheral lymphocytes do not express the LTβR, while TR2 expression was associated with T-cell activation.

To investigate whether the membrane-bound AIM II exert different activities on the lymphocytes, co-culture experiments of TIL1200 cells with MDA-MB-231/AIM II cells was carried out. TIL1200 is a CD8+(995) tumor infiltrating lymphocyte line expressing a high level of Fas. The membrane-bound AIM II did not induce apoptosis of TIL1200, whereas the addition of Fas antibody triggered 90% of TIL1200 undergone apoptosis. Similar results were obtained with fresh TIL cells or Jurkat cells.

Figure 9:
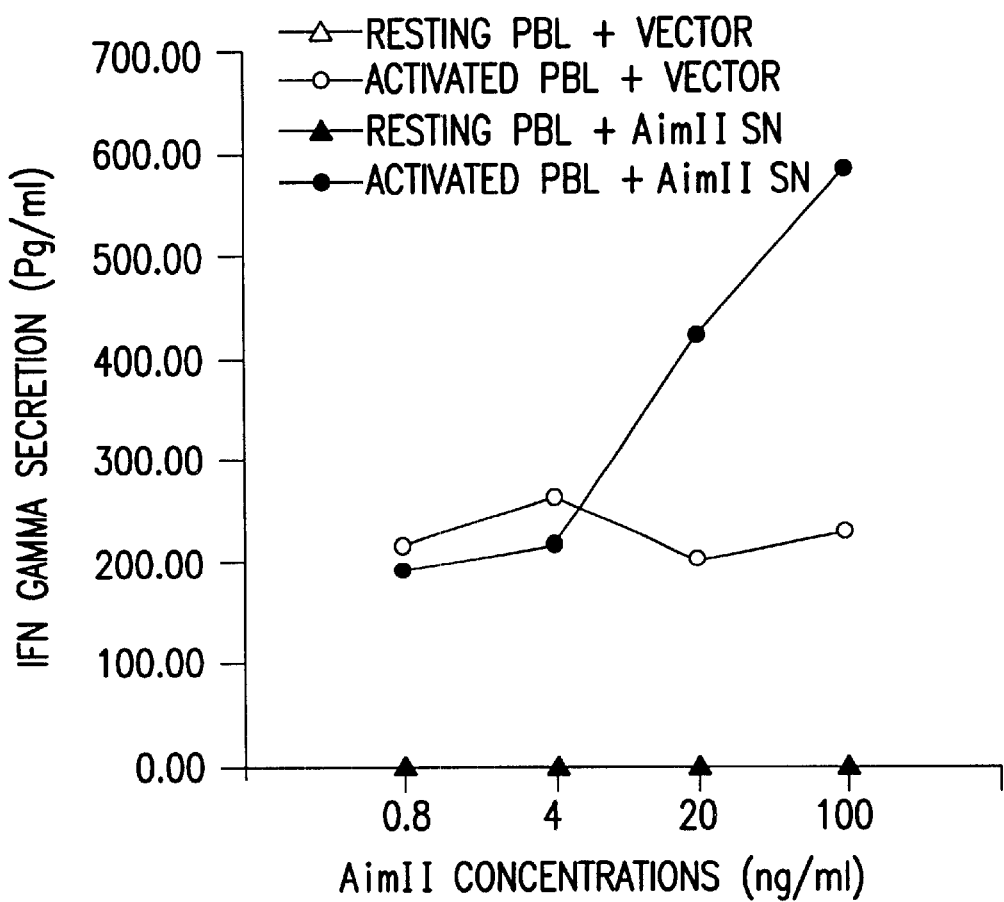
FIG. 9 shows secretion of IFN-γ by sAIM II treated human PBL cells. Human PBLs ($5 \times 10^5$ cells per well in the 96 well plate) were treated with or without anti-CD3 mAb and IL-2(20 U/ml) in the presence or absent of sAIM II for 5 days. The supernatants were then collected from the following groups of cells: PBLs in the presence (filled circle) or absence (open circle) or sAIM II, or the resting PBLs with (filled triangle) or without (open triangle) sAIMII. Human IFNy concentration were determined by ELISA.

Furthermore, several lymphoid cell lines and PBLs were screened for their responsiveness to the soluble AIM II protein. No cytotoxicity of AIM II was shown in Jurkat cells (either resting or CD3 mAb activated), K562 cells, or TIL1200 (tumor infiltrating lymphocytes), PBMC (fresh or IL-2/CD3 mAb activated) (FIG. 8L). In contrast, treatment of PBLs with sAIM II, resulted in activation of TR2 expressing T cells as demonstrated by release of IFNγ (FIG. 9).

Discussion

In the foregoing experiments, the biological functions of AIM II and its possible mechanisms of action as a novel ligands of LTPR and TR2 have been characterized. The results demonstrate that the AIM II protein exhibits potent cytotoxicity primarily in transformed tumor cells both in vitro and in vivo, while at the same time, activating lymphocytes. The biological activities of AIM II in vitro and in vivo clearly distinguish AIM II from other known members of the TNF/FasL family in several ways including binding to two distinct signaling pathways: LTβR and TR2. Since the ability of AIM II expression to inhibit tumor growth was demonstrated in both xenographic (immunodeficient) and syngeneic (immunocompetent) models, the results suggest that the T-cell mediated tumor specific response may not be an essential factor for the primary tumor rejection in this study.

Activation of the TNF receptors family can directly induce cell proliferation, or differentiation or death. The foregoing experiments show that AIM II expression resulted in growth inhibition and apoptosis in the human breast carcinoma cell line MDA-MB-231 in conjunction with serum starvation, or addition of IFNγ. Induction of apoptosis appears to be the primary cause for the growth inhibition in vitro as shown in Annexin-V FACS analysis and DNA fragmentation. The morphology and growth pattern of MDA-MB-231/LT-γ cells suggest involvement of some loss of cells adhesion. Browning et al. have shown that Fas activation led to rapid cell death (12–24 h), TNF effects requires 24 h and LTcx102 heterotrimers were slowest (2–3 days) in induction of apoptosis for HT-29 cells. Lysis of the LTγR and TR2 expressing MDA-MB-231 and HT-29 cells in response to the treatment with the soluble AIM II protein showed similar slow effect, i.e. at least 3–5 days. Substantial cell lysis does not occur even after 3–4 days for some cell lines. The dynamics of action of AIM II are more similar to LTα1β2 heterotrimers.

AIM II was originally identified from a human activated T cell library by screening of sequence homology with cysteine-rich motif of the TNF/Fas ligand and receptor superfamily. Like other TNF-related ligands, AIM II is a type-II transmembrane protein with C-terminus on the exterior cell surface, a single transmembrane domain, and a short cytoplasmic tail. As predicted, transduction of a full-length cDNA of AIM II gene resulted in cell surface expression of a protein which binds to two receptors as demonstrated in FACS analyses. A soluble AIM II protein is sufficient to bind to both receptors and trigger cytotoxic effects on the target cells. However in the transwell co-culture experiment, where two type of cells shared the culture medium but are physically separated, cytotoxicity from the AIM II expressing MDA-MB-231 cells towards the wild type MDA-MB-231 or HT-29 cells was not observed. In the direct co-culture assay, membrane-bound AIM II effectively mediated killing from close contact. Thus, it seems that natural AIM II protein may not be a secreted protein. Fluorescence in situ hybridization (FISH) localized AIM II gene to human chromosome 16, band p 11.2. The AIM II position is in close proximity with Core binding protein, sulfotransferase, syntaxin 1B, retinoblastoma-binding protein 6, zinc finger protein 44, cell adhesion regulator and Wilms tumor-3 gene. Genes encoding other known TNF ligands such as TNF, LTα, and LTβ are tightly linked on human chromosome 6 within the major histocompatibility complex (MHC) sandwiched between the class lil and HLA-B locus.

Both LTβR and TR2 lack the death domain. Thus, the demonstration of AIM II binding to both LTβR and TR2 is intriguing. Although LTβR and TR2 could activate common signaling pathways via association with TNFR-associated factors (TRAFs), AIM II-LTβR and AIM II-TR2 interactions may trigger the distinct biological events. As shown in this Example, expression of AIM II leads to the death of cells expressing both LTβR and TR2 while activate lymphocytes which expressing only the TR2 receptor. Signaling through the LTβR activates a TRAF3-dependent pathway. In contrast, AIM II-TR2 interaction probably elicits stimulatory responses of host immune system through TRAFs (TRAFI, TRAF2, TRAF3 and TRAF5). This AIM II dual signaling hypothesis is further supported by the distinct tissue and cell expression patterns of LTβR and TR2. LTβR is prominent in tumor and other epithelial cells, but is absent on the T and B cells. In contrast, TR2 is abundantly expressed in comparable levels in resting and activated T cells, B cells and monocytes and granunocytes. Hence, AIM II probably plays critical roles such as induction of apoptosis and immune activation and, therefore, may have an therapeutic application for cancer.

The LTβR was originally described as a transcribed sequence encoded on human chromosome 12p, a member of the TNFR superfamily. The LTβR is implicated as a critical element in controlling lymph node development and cellular immune reactions. It has been showed that LTβR is expressed in a variety of tissues and cell lines including tumor lines. Unlike other members of the TNFR family, LTβR is not expressed by T nor B lymphocytes. Activation of LTβR by using recombinant LTα1β2 heterotrimers or by cross-linking with immobilized antibodies, induces the death of adenocarcinoma cell lines and production of chemokine IL-8 and RANTES, even though LTβR does not contain the death domain in its cytoplasmic region.

TR2 is expressed in multiple human tissues and shows a constitutive and relatively high expression in hemopoeintic lineage cells including resting and activated CD4+and CD8+T cells, B cells, monocytes and neutrophils. The TR2 cytoplasmic tail does not contain the death domain seen in the Fas and TNFR-I intracellular domains, and appears to be more related to those of CD40 and 4-1BB. Signals through 4-1BB and CD40 have been shown to be co-stimulatory to T cells and B cells, respectively. A TR2-Fc fusion protein inhibited a mixed lymphocyte reaction-mediated proliferation, in contrast to FasL and TNF, which trigger apoptosis. All the hemopoietic derived cells tested expresses the TR2 receptor but are resistant to AIM II mediated killing observed in the tumor cells. This indicates that TR2 alone does not mediate death signal. However, since all cancer cells examined expressed both LTβR and TR2, it remains to be elucidated whether both AIM II-LTβR and AIM II-TR2 signaling contributes equally for the AIM II mediated cytotoxicity in tumor cells. We also can not exclude the possibility that AIM II interacts with other known or unknown death receptors such as DR3, DR4 and DR5, although soluble AIM II does not bind to DR3, DR4 and DR5 in an in vitro binding assay.

The dose-limiting toxicity of TNF and cytoxicity of FasL for T-cells limits their clinical application. Treatment with AIM II could be alternatively attractive approach since AIM II trigger the stimulatory signal rather than the death signal to the host immune cells which expressing the TR2 but lacking the LTβR. AIM II has the ability to selectively induce death of tumor cells probably through LTβR and TR2 and at the same time can trigger secretion of IFNγ from lymphocytes apparently through the TR2 signaling pathway. This model thus demonstrates that AIM II is not only an attractive candidate for the future development an an anti-cancer agent, but more importantly, it provides an novel system, distinct from the previously defined TNF or Fas system, for the further understanding of the signaling pathway of members of TNF ligand-receptor interactions.

Methods

Molecular Cloning of AIM II Full Length Gene

A database containing more than one million ESTs (expression sequence tags) obtained from over 500 different cDNA libraries has been generated through the combined efforts of Human Genome Science Inc. and The Institute for Genomic Research using high throughput automated DNA sequence analysis of randomly selected human cDNA clones. Sequence homology comparisons of each EST were performed against the GenBank database using the blastn and blastn algorithms, ESTs having homology to previously identified sequences (probability equal or less than 0.01) were given a tentative name based on the name of the sequence to which it was homologous. A specific homology and motif search using the conserved amino acid sequence, GLYLIYSQVLF (SEQ ID NO:46), of the TNF/Fas ligand family against this human EST database revealed several EST having >50% homology. One clone containing GYYY-IYSKVQL (SEQ ID NO:47) from human activated T cell library was selected. This EST was sequenced on both strands to the 3' end. Its homology was confirmed. The initial clone lacks the 5' portion of the gene in comparison to other members of TNF family. To obtain the full length sequence, a nested PCR reaction was carried out using two gene specific oligonucleotides and two vector-specific primers. An additional 72 nucleotides at the 5' end was obtained. The full length sequence was then cloned into the vector pCM-Vsport 2.0 (Life Technologies Inc., Rockville, Md.).

Northern Blot Analysis

Human multiple tissue Northern blots (Clontech, MTN blots, #7759-1 and #7760-1) were probed with a $^{32}$P-labelled AIM II full length cDNA according to the vendor's instructions. The blots were hybridized overnight in Hybrisol solution (Oncor), preheated to 42° C. before use, followed by two subsequent washes in 2×SSC/0.1% SDS and 0.2×SSC/0.1% SDS at 42° C. and visualized using a Phospholmager™ (Molecular Dynamics Co.).

In Situ Hybridization and FISH Detection

To determine the precise chromosomal location of the AIM II gene, single-copy gene fluorescence in situ hybridization (FISH) to normal human metaphase chromosome spreads was attempted (Lawrence et al., 1988). A 2 Kb cDNA was nick-translated using Digoxigenin-11-dUTP (Boehringer Mannheim) and FISH was carried out as detailed in Johnson et al., 1991b. Individual chromosomes were counterstained with DAPI and color digital images, containing both DAPI and gene signal detected with Rhodamine, were recorded using a triple-band pass filter set (Chroma Technology, Inc., Brattleburo, Vt.) in combination with a cooled charge coupled-device camera (Photometrics, Inc., Tucson, Ariz.) and variable excitation wave length filters (Johnson et al., 1991a). Images were analyzed using the ISEE software package (Inovision Corp., Durham, N.C.).

Cells and Reagents

The human breast carcinoma MDA-MB-231, subclone 2LMP, obtained from in vivo passage of MDA-MB-231 cells in athymic nude mice, was used in all the experiments. MC-38 is a 1,2-dimethylhydrazine induced murine colon adenocarcinoma which is of H-2b origin. Human T lymphoma line Jurkat and CHO lines were obtained from the American Type Culture Collection (ATCC, Rockville, Md.). A human melanoma antigen gp100 reactive CD8+T-cell line TIL1200 was kindly provided by Dr. Yutaka Kawakami (National Cancer Institute, Bethesda, Md.). All tumor cell lines were grown and maintained in RPMI 1640 medium containing 10% FCS, except MDA-MB-23 1, which used Dulbecco's modified Eagle's medium as basal medium. HLA-A2 restricted TIL 1200 was grown in Aim-V medium containing 10% human serum and 1000 U of IL-2. The apoptosis inducing anti-Fas Mab CH-11 was obtained from Upstate Biotechnology. Interfreon was obtained from Biosource International (CA).

Production of Soluble AIM II

The sequence encoding amino acids 74–240 of AIM II, i.e., the putative extracellular domain, was subcloned into the vector pFLAG.CMV-1 in frame with sequences encoding the preprotrypsin signal peptide and the FLAG peptide tag. The resulting construct, pFLAG-sAIM II, was transfected into 293T cells to generate recombinant sAIM II. Culture media from cells transfected pFLAG.CMV-1 or pFLAG-sAIM II were passed through anti-FLAG mAb (Eastman Kodak Co.) affinity columns. The column eluents were fractionated by SDS-PAGE and sAIM II was detected by western blot analysis, using the anti-FLAG mAb and ECL detection reagents (Amersham International).

Generation of Recombinant Receptor-Fc Fusion Proteins

A cDNA encoding extracellular domain of human LTαR was amplified from a HepG2 cells by RT-PCR technique. The sequences of oligonucleotide primers are as following: Forward 5' CGGGATCCATGCTCCTGCCTTGGGCCAC 3' (SEQ ID NO:48); and Reverse: 5' GCGGATC-CTGGGGGCAGTGGCTCTAATGG 3' (SEQ ID NO:49) and contained BamHI restriction sites on each end to facilitate the cloning of PCR product into the pSK+vector (Stratagene). The amplified sequence was subjected to BamHI digestion and ligated to BamHI cut pSK+vector for sequencing. The fidelity of amplified cDNA fragment was confirmed by dideoxy DNA sequencing. To obtain human LTβR-Fc fusion protein, extracellular domain of LTβR was excised from pSK+vector with BamHI restriction endonuclease and ligated to BglII cut pUC19-IgG1-Fc vector to allow in frame ligation. To generate recombinant baculovirus, fusion gene was firstly excised with HpaI/HindIII from pUC19-IgG-Fc vector, followed by ligation with SmaI cut pBacPAK9 vector (Clontech Co.) after fill-in, then co-transfected with linearized BacPAK6 DNA (Clontech Co.) into Sf9 cells. To obtain recombinant soluble LTβR fusion protein, five days culture supernatants from recombinant virus infected insect Sf21 cells was filtered and trapped onto protein A Sepharose beads, the bound sLTβR protein was then eluted with glycine buffer (pH 3.0) and followed by dialysis in PBS. Production of TR2-Fc fusion protein has been described.

Generation of LTβR and TR2 Antibodies

Balb/cJ mice (The Jackson Laboratory, Bar Harbor, Me.) were immunized with LTβR-Fc fusion proteins in Freund's adjuvant. Mice were boosted three times then the spleen cells were fused with the murine myeloma NS-1 cells in the presence of 50% polyethylene glycol in HEPES (PEG 1500, Boeheringer Mannheim), followed by culture in RPMI 1 640/HAT and RPMI 1640/HT selective medra (Boehringer Co.). Supernatant from positive wells were tested for the ability to bind LTβR-Fc fusion protein, but not human IgG1 by ELISA. Hybridomas producing antibodies against LTβR-Fc fusion protein were cloned by limiting dilution three times. To produce large amount of mAbs, $10^7$ hybridoma cells were injected into pristane treated peritoneal cavity of Balb/c mice, and mAbs was subsequently purified from ascites by affinity chromatography. Similarly, using TR2-GST fusion protein, monoclonal antibodies against TR2 were produced and screened by ELISA assay.

In Vitro Growth Assays

Cells (5,000 cells per well) were plated in triplicate in 24-multiwell tissue culture plates with IMEM in the presence of either 10% FBS or 1% FBS. The number of live cells were determined by trypan blue exclusion method at day 3, day 5 or day 7. Cells were refed with fresh medium every two days during this time course.

A soluble tetrazolium/formazan (XTT) assay for cell growth in a 96-well plate was performed. Cells (2,000–4,000 cells/well) were grown in IMEM medium with 10% FBS or 1% FBS. After four to five days culture, XTT (1.0 mg/ml plus PMS at 1.53 mg/ml) was added to each well and incubated for four hours at 37° C. Absorbance at 450 nm was measured with the Dynatech Model MR700.

FACS Analysis

Cells were collected by trypsinization or aspiration, and centrifuged at 1500–2000 rpm for 5 min. The cell pellets were resuspended and washed in 5 ml ice-cold PBS twice. And then, the cells were incubated with Flag-tagged AIM II protein or Abs at 10 μg/ml in the binding buffer (HBSS containing 10% BSA, 20 mM HEPES, pH 7.2, 0.02% $NaN_3$, and 25 μg/ml normal rat Ig) for 30 min at 4° C. Cells were then washed and stained with phycoerythrin (PE) conjugated to goat anti-mouse IgG at 20 μg/ml as described. To compete for cell surface binding, soluble LTβR-Fc fusion protein, TR2-Fc at 10 μg/ml was preincubated with AIM II for 30 min before adding to cells. Fluorescence was analyzed by a FACscan flow cytometer (Becton Dickinson, Mountain View, Calif.).

For apoptosis assay, cell pellets were resuspended in 1X binding buffer (10 mM HEPES pH 7.4, 0.15 M NaCl, 5 mM KCl, 1 mM $MgCl_2$, 1.8 mM $CaCl_2$) containing 1:100 dilution of Annexin V-FITC (Trevigen, Gaithersburg, Md.) and 50 μg/ml of propidium iodide and incubated at 4° C. for 15 min. The fluorescence of Annexin V-FITC and propidium iodide of individual cells were analyzed by flow cytometry (Coulter).

Retroviral Transduction of Tumor Cells

A retroviral vector was used to stably transduce tumor cells with AIM II gene. To construct a plasmid encoding the AIM II, a 1.9 kb NotI/SalI fragment containing the AIM II cDNA was inserted into a parental plasmid pG1 SamEN. This retroviral backbone was derived from the Moloney murine leukemia virus and the AIM II gene was under the transcription control of the long-terminal repeat from the Moline murine leukemia virus. Generation of the retroviral packaging line was described previously (Markowitz et al.). Briefly, 30 μg of pG1SamEN-AIM II DNA were used to transfect a mixture of $2 \times 10^5$ PA317 amphotropic packaging line and $3 \times 10^5$ GP+E86 ecotropic packaging line. After 2 week of selection, high-titer G418-resistant PA317 clones were then selected to recreate the packaging line PA-AIM II and used for gene transfer into tumor cells. A control retrovirus producing line PA-neo was also used. These packaging lines were grown for 20 h and the retroviral supernatants were harvested, added to a 75% confluent flask of wild type MDA-MB-231 or MC-38 respectively. Following transduction with a recombinant retrovirus encoding the human AIM II, AIM II expressing MDA-MB-231 or MC-38 cells were selected with the neomycin analogue G418 and designated MDA-MB-231/AIM II or MC-38/AIM II respectively. AIM II expression in these tumor cells was confirmed by Northern blot analyses. All stable transfectants including MDA-MB-231/AIM II, vector control line MDA-MB-231/neo, MC-3 8/AIM II and the vector control line MC-38/neo were grown and maintained in the presence of G418 at 1.5 mg/ml and 0.375 mg/ml, respectively.

Coculture Assays of Jurkat Cells

The MDA-MB-231 cells were plated in 6-well tissue culture plates and allowed to grow to confluence. Following removal of media and washing of the monolayers with 1×PBS, 1×10$^6$ Jurkat cells (nonadherant) were plated in 1 ml of RPMI medium over a monolayer or an empty wells. Wells with MDA-MB-231 cells alone (without overlaying Jurkat cells) were maintained as additional control. After 24 or 48 hours of culture, the nonadherant phase of the mixed culture was collected from the 6-well plated after gentle rocking of the plate and assayed for viability using trypan blue exclusion. For detection of apoptosis, 20,000 cells were measured per sample using Annexin V-FITC FACScan flow cytometer.

Lymphokine Release Assay

The lymphokine release assays were performed to detect human PBL reactivity with AIM II as previously described. (Zhai et al.) Briefly, human PBL cells were incubated for 5 days in the presence of anti -CD3 mAb (0.1 $\mu$g/ml) and rIL-2 20 U/ml plus AIM II protein at various concentrations, the supernatants were collected and the secretion of IFN$\gamma$ were determined using ELISA kits purphased from R&D Systems (Minneapolis, Minn.).

Tumorigenicity Studies

Female athymic Ncr-nu nude mice, 6 week old, were obtained from the Frederick Cancer Research and Development Center, National Institute of Health (Frederick, MD) and Charles River Laboratories (Raleigh, N.C.). Female C57BL/6 mice, 6–7 wk old, were purchased from Harlan Sprague Dawley (Indianapolis, Ind.). MDA-MB-231 cells (1×106)were injected on day 0 into the mammary fat pad of the female athymic nude mice and similarly, MC-38 cells were injected s.c. into the flank region of C58BL/6 mice. Mice were then ear tagged and randomized. Tumor size was assessed by measuring perpendicular diameters with a caliper twice weekly in a blinded fashion. Each treatment group consisted of ten animals and experiments were repeated three times. Tumor histological examination was carried out with H/E staining.

Example 6

Detection of AIM II Expression by BIAcore Analysis

CHO cells were transfected with either an AIMII-Flag tag expression vector or an BAP-Flag (negative control). Three days after transfection, AIMII expression was determined using the BIAcore instrument (BIAcore, Inc.) which permits real-time measurements of protein binding events to immobilized AIMII receptor, lymphotoxin-$\beta$ receptor (BIAcore sensorgram detects binding by changes in refractive index at the surface of the flow cell). A lymphotoxin-$\beta$ receptor-Fc fusion protein was covalently immobilized to the BIAcore flow cell via amine groups using N-ethyl-N'-(dimethylaminopropyl)carbodiimide/N-hydroxysuccinimide chemistry. Various dilutions of AIM II-Flag and the negative control (BAP-Flag) conditioned serum-free media were applied to the lymphotoxin-$\beta$-receptor-derivatized flow cell at 5 $\mu$l/min for a total volume of 50 $\mu$l. The amount of bound protein was determined after washing the flow cell with HBS buffer (10 mM HEPES, pH 7.4, 150 mM NaCl, 3.4 mM EDTA, 0.005% Surfactant P20). The flow cell surface was regenerated by displacing bound protein by washing with 20 $\mu$l of 10 mM HCl.

The specific binding to the lymphotoxin-$\beta$-receptor was detected at up to 10-fold dilution of the conditioned media from AIMII-Flag cultures, whereas, no significant binding was observed for the negative control (BAP-Flag) conditioned media. This demonstrates that AIMII-Flag binding is specific to lymphotoxin-$\beta$-receptor and not to the Fc portion of the fusion protein. Moreover, specific receptor binding by AIMII-Flag protein indicates that it exhibits a native structure as secreted by the cells. Thus, this BIAcore-based assay can be used to detect expression of AIMII from conditioned media and other biological fluids. Further, by using known amounts of pure AIM II protein this assay can be developed into a quantitative assay for determining AIM II concentrations.

Example 7

Activation-induced Apoptosis Assay

Activation-induced apoptosis is assayed using SupT-13 T leukemia cells and is measured by cell cycle analysis. The assay is performed as follows. SupT-13 cells are maintained in RPMI containing 10% FCS in logarithmic growth (about 1×10$^6$). Sup-T13 cells are seeded in wells of a 24 well plate at 0.5×10$^6$/ml, 1 ml/well. AIM II protein (0.01, 0.1, 1, 10, 100, 1000 ng/ml) or buffer control is added to the wells and the cells are incubated at 37° C. for 24 hours. The wells of another 24 well plate were prepared with or without anti-CD3 antibody by incubating purified BC3 mAb at a concentration of 10 $\mu$g/ml in sterile-filtered 0.05M bicarbonate buffer, pH 9.5 or buffer alone in wells at 0.5 ml/well. The plate is incubated at 4° C. overnight. The wells of antibody coated plates are washed 3 times with sterile PBS, at 4° C. The AIM II treated Sup-T13 cells are transfered to the antibody coated wells and incubated for 18 hr., at 37° C. Apoptosis is measured by cell cycle analysis using propidium iodide and flow cytometry. Proliferation of treated cells is measured by taking a total of 300 $\mu$l of each treatment well and delivering in to triplicate wells (100 $\mu$l/well) of 96 well plates. To each well add 20 $\mu$l/well $^3$H thymidine (0.5 $\mu$Ci/20 $\mu$l, 2 Ci/mM) and incubate 18 hr., at 37° C. Harvest and count $^3$H-thymidine uptake by the cells. This measurement is used to confirm an effect on apoptosis if observed by other methods. The positive control for the assay is Anti-CD3 crosslinking alone. In addtion, profound and reproducible apoptosis in this line using anti-fas monoclonal antibody (500 ng/ml in soluble form-IgM mAb) has been demonstrated. The negative control for the assay is medium or buffer alone. Also, crosslinking with another anti-CD3 mAB (OKT3) has been shown to have no effect.

If an effect is observed by cell cycle analysis the cells will be further stained for the TUNEL assay for flow cytometry or with Annexin V, techiques well known to those skilled in the art.

Example 8

CD3-induced Proliferation Assay

A CD3-induced proliferation assay is performed on PBMCs and is measured by the uptake of $^3$H-thymidine. The assay is performed as follows. Ninety-six well plates are coated with 100 μl/well of mAb to CD3 (HIT3a, Pharmingen) or isotype-matched control mAb (B33.1) overnight at 4° C. (1 μg/ml in .05M bicarbonate buffer, pH 9.5), then washed three times with PBS. PBMC are isolated by F/H gradient centrifugation from human peripheral blood and added to quadruplicate wells ($5 \times 10^4$/well) of mAb coated plates in RPMI containing 10% FCS and P/S in the presence of varying concentrations of AIM II protein (total volume 200 μl). Relevant protein buffer and medium alone are controls. After 48 hr. culture at 37° C., plates are spun for 2 min. at 1000 rpm and 100 μl of supernatant is removed and stored −20° C. for measurement of IL-2 (or other cytokines) if effect on proliferation is observed. Wells are supplemented with 100 μl of medium containing 0.5 μCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative control for CD3-induced proliferation and medium or buffer are used as negative controls for the effects of AIM II proteins.

Example 9

Effect of AIM II on the Expression of MHC Class II, Costimulatory and Adhesion Molecules and Cell Differentiation of Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FcγRII, upregulation of CD83). These changes correlate with increased antigen-presenting capacity and with functional maturation of the dendritic cells.

FACS analysis of surface antigens is performed as follows. Cells are treated 1–3 days with various concentrations of AIM-II (0.1, 1, 10, 100, 1000 ng/ml) or LPS as positive control, washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the Production of Cytokines

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA will be used to measure the IL-12 release as follows. Dendritic cells ($10^6$/ml) are treated with AIM-II (0.1, 1, 10, 100, 1000 ng/ml) for 24 hours. LPS (100 ng/ml) is added to the cell culture as positive control. Supernatants from the cell cultures are then collected and analyzed for IL-12 content using commercial ELISA kit. The standard protocols provided with the kits are used.

Effect on the Expression of MHC Class II. Costimulatory and Adhesion Molecules

Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis will be used to examine the surface antigens as follows. Monocytes are treated 1–5 days with various concentrations of AIM-II (0.1, 1, 10, 100, 1000 ng/ml) or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on Monocyte Survival

Human peripheral blood monocytes progressively lose viability when cultured in absence of serum or other stimuli. Their death results from internally regulated processes (apoptosis). Addition to the culture of activating factors, such as TNF-α, dramatically improves cell survival and prevents DNA fragmentation. Propidium iodide staining will be used to measure apoptosis as follows. Monocytes ($10^7$/ml) are cultured in suspension in polypropylene tubes in DMEM for two days in presence or absence of TNF-α (100 ng/ml, positive control) or AIM-II (0.1, 1, 10, 100, 1000 ng/ml). Cell viability is assessed by propidium iodide (PI) staining. Cells are suspended at a concentration of $2 \times 10^6$/ml in PBS containing PI at a final concentration of 5 μg/ml, and then incubated at room temperature for 5 minutes before FACScan analysis. PI uptake has been demonstrated to correlate with DNA fragmentation in this experimental paradigm.

Effect on Cytokine Release

An important function of monocytes/macrophages is their regulatory activity on other cellular populations of the immune system through the release of cytokines after stimulation. An ELISA to measure the IL-I 1β release is performed as follows. Human monocytes are added at $10^6$/ml in 48-well plates and various concentrations of AIM-II are added (0.1, 1, 10, 100, 1000 ng/ml) in presence or absence of 100 ng/ml LPS. After 24 hour incubation, the supernatants are collected and assayed for the presence of cytokines by ELISA kits. The standard protocols provided with the kits are used.

Example 10

Affinity Purification of Soluble AIMII for N-terminal Sequence Analysis

Figure 7A:
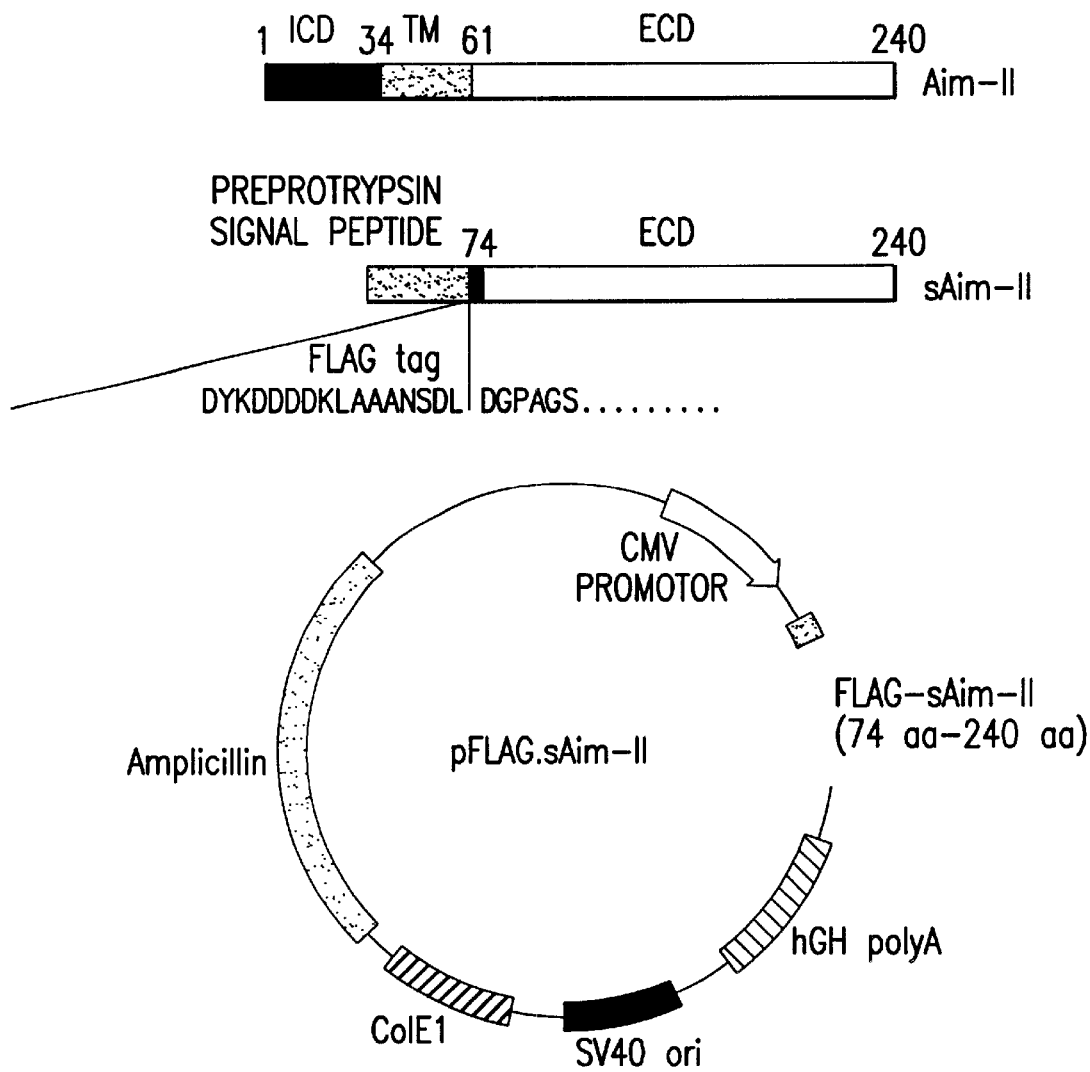
FIG. 7 shows the pFlag-AIMII plasmid construct (FIG. 7A) Cytotoxicity of a recombinant soluble form of AIM II (sAIMII) in MDA-MB-231 cells in the presence or absence of IFNγ (FIG. 7B) or with IFNγ alone (FIG. 7C). Experiments were carried out as described in Example 5 Materials and Methods.
Figure 7B:
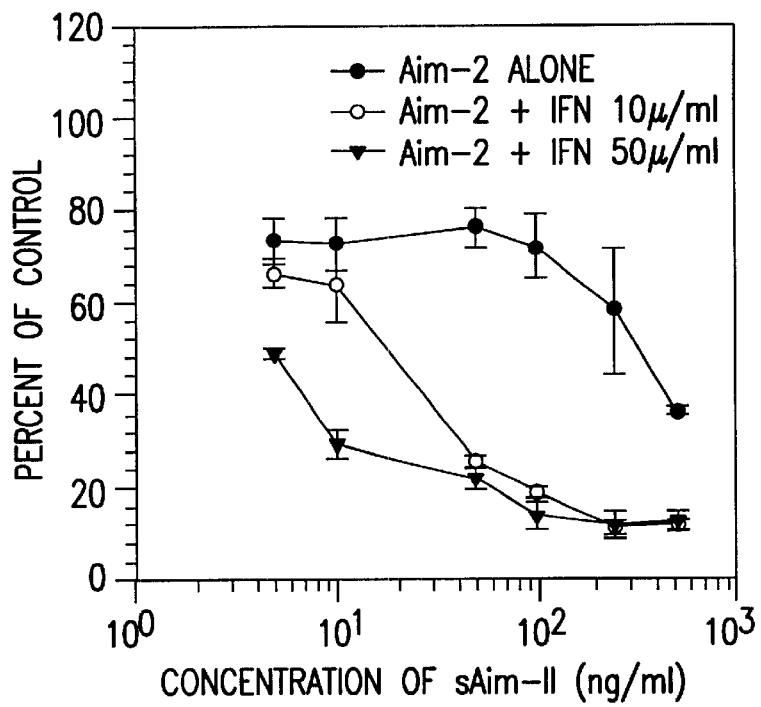
Figure 7C:
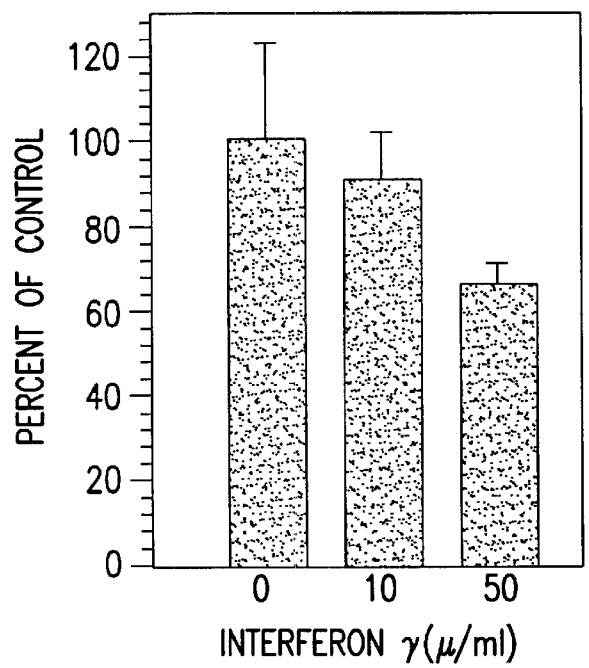

Previous data indicated that a BIAcore chip derivatized with the lymphotoxin beta receptor (LTβR)-Fc fusion protein was able to specifically bind AIM II (a.a. 74–240)-Flag fusion protein (See Example 5, section E and FIG. 7A). The LTβR BIAcore chip was then used to detect expression of soluble AIM II protein from conditioned media of non-Flag tagged AIM II stable transfectants in order to determine which cell line(s) should be used for further purification for N-terminal sequence analysis.

CHO cells were transfected with an expression construct (pC4 vector) consisting of the extracellular region of AIM II (amino acids 60–240) fused to the ck-beta 8 signal peptide.

~25kDa apparent molecular mass of the CHO-11 expressed ck-beta8/AIM II fusion protein was larger than that predicted from its sequence (20,361). Again this might also be due to glycosylation of the protein (there is one N-glycosylation site at residue 104 of full length AIM II).

TABLE 1

N-terminus of AIM2 purified from MCA-38 or CHO-11 clone conditioned media.

| | |
|---|---|
| N-terminus MCA-38[1] | _____LIQER.... |
| N-terminus CHO11[1] (40%) | SQAGS............................... |
| N-terminus CHO-11[1] (40%) | ___GSQLH............................. |
| ck-beta-8-AIM2 sequence | SQAGSQLHWRLGEMVTRLPDGPAGSWEQLIQERN |

[1]= Affinity purified AIM II from MCA-38 or CHO-11 conditioned media.
[2]=Amino acid sequence at junction of ck-beta-8 and extracellular region of AIM
II. Double underlined sequence corresponds to ck beta 8 signal sequence (SQA), and in the case of the GS residues sequence introduced during cloning. AIM II sequence starts at the 6th residue, Q.
Values in parenthesis represent percentage of each sequence found in AIM II sample.

Clones were selected for high expression by growth in media containing methotrexate. The clones with the highest amount of binding to LTβR BIAcore chip were further amplified. Conditioned media (20 mL) from CHO 11, a high level AIM II producing clone, was obtained. A second AIM II construct encoding the complete full length cDNA was transfected into murine MCA-38 carcinoma cells and subject to selection with G418. Conditioned media was obtained from these transfected MCA-38 cells.

Conditioned media from the stable transfectants, CHO 11 or MCA-38 cells, were filtered, centrifuged at 10,000×g and then passed over an MCIF-Fc affinity column (control column) followed by the LTβR-Fc affinity column (0.2 mL bed volume). The columns were washed with several bed column volumes HEPES buffered saline containing 0.005% Surfactant P-20. Bound protein was eluted with 10 mM HCl (3×0.5 mL fractions) and immediately neutralized with TRIS buffer. The fractions eluted from the LTβR column retained binding to LTβR BIAcore chip, whereas, fractions eluted from the control MCIF-Fc column were negative for binding. The eluted fractions were dried in Spedvac then resuspended in 20 μL water. An aliquot of the eluted protein was analyzed by reducing SDS-PAGE gels and detected by silver staining. A band of approximately ~25 kDa and ~21 kDa was detected specifically bound to the LTβR column from CHO-11 and MCA-38 cell lines. The remaining eluted material was subject to SDS-PAGE and blotted onto PVDF membrane for N-terminal sequence analysis.

Figure 12:
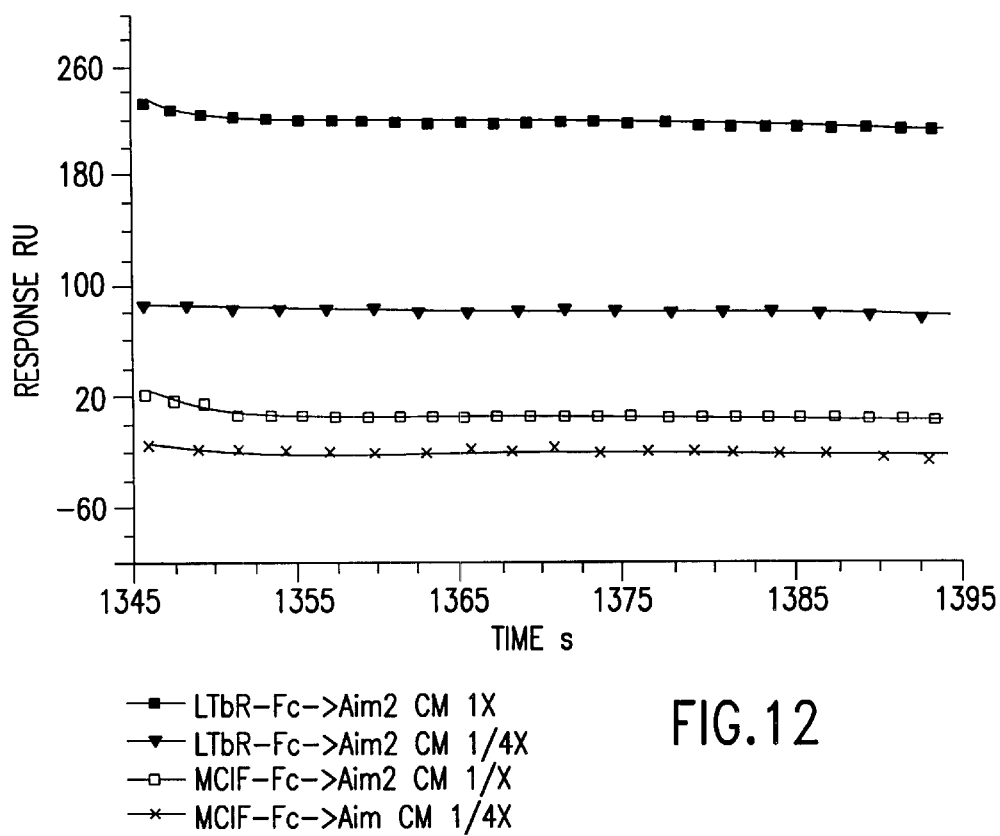
FIG. 12 shows a sensorgram of specificity of binding of MCA-38 AIM II conditioned media to LTβR-Fc versus MCIF-Fc immobilized on BIAcore chip. Conditioned media was analyzed on a BIAcore instrument flowcell derivatized with lymphotoxin beta receptor Fc fusion protein. The conditioned media (100 μL) was flown over the chip at 5 μL/min and washed with HBS buffer also at 5 μL/min. The shown data represents the net bound (off-rate) region of the plot after binding of AIM II to immobilized receptor and is measured in relative mass units (RU) versus time. The binding conditions were performed at high receptor chip densities under diffusion-limited conditions. Legend: LTβR-Fc and MCIF-Fc refer to binding data from LTβR-Fc or MCIF-Fc immobilized BIAcore chip surfaces, respectively.

The N-terminus of the AIM II molecule purified from MCA-38 cells started at residue 83 within the predicted extracellular region of the molecule (Table 1, below). The results of the AIM II from CHO-11 also confirmed that this protein correspond to AIM II protein; the N-terminus contained two sequences starting three residues apart which start within the ck-beta 8 signal peptide followed by the extracellular region of AIM II starting at residue 60 (Table 1, below). Thus, the natural processed form of AIM II should correspond to residues 83–240 and have a molecular mass of 17,284 daltons. The apparent electrophoretic mobility of [1]8 21 kDa is consistent with glycosylation as evident by presence of several electrophoretic species. Similarly, the The Sensorgram of specificity of binding of MCA-38 AIM II conditioned media to LTβR-Fc versus MCIF-Fc immobilized on BIAcore chip is shown in FIG. 12. The conditioned media was analyzed on a BIAcore instrument flowcell derivatized with lymphotoxin beta receptor Fc fusion protein. The conditioned media (100 μL) was flown over the chip at 5 μL/min and washed with HBS buffer also at 5 μL/min. The shown data represents the net bound (off-rate) region of the plot after binding of AIM II to immobilized receptor and is measured in relative mass units (RU) versus time. The binding conditions were performed at high receptor chip densities under diffusion-limited conditions. Legend: LTβR-Fc and MCIF-Fc refer to binding data from LTβR-Fc or MCIF-Fc immobilized BIAcore chip surfaces, respectively.

Figure 13:
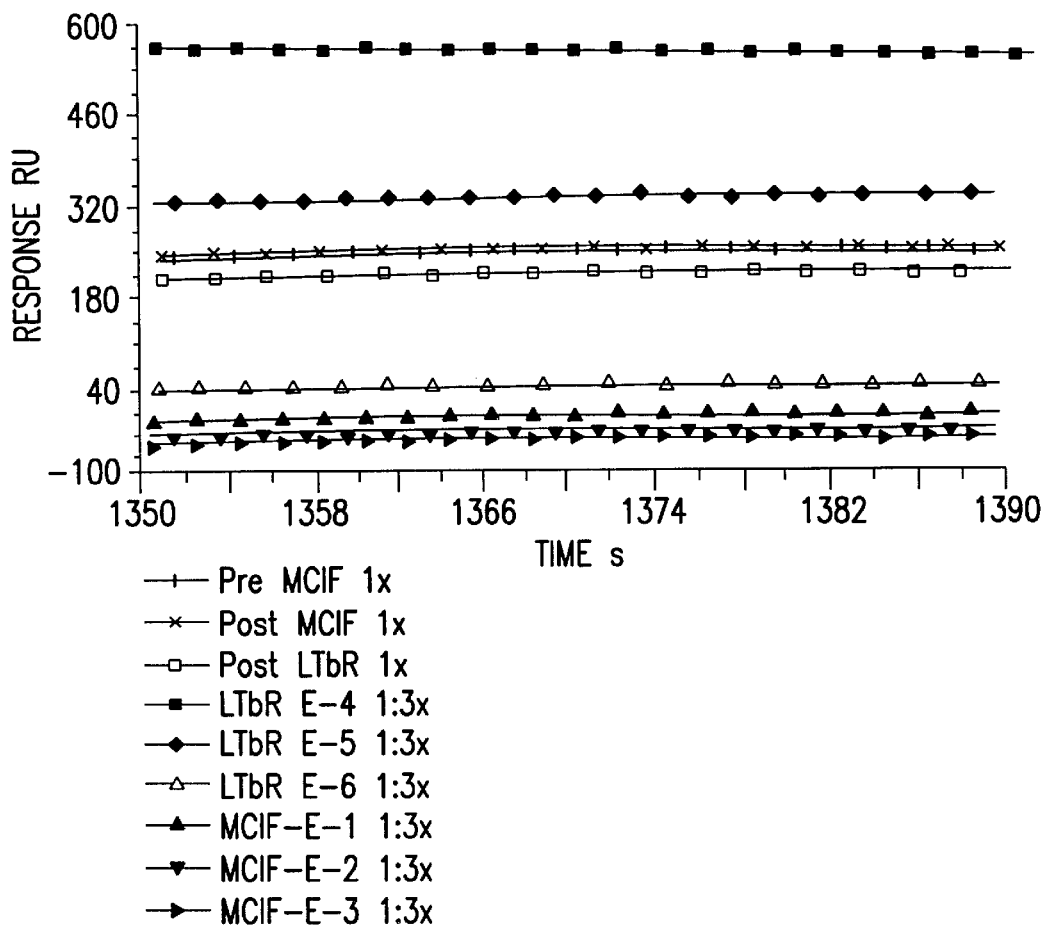
FIG. 13 shows the determination of the LTβR binding by AIM II eluted from LTβR-Fc column. Binding conditions were as described in FIG. 11. Legend: LTβR and MCIF refer to binding data from LTβR-Fc or MCIF-Fc immobilized BIAcore chip surfaces, respectively. Undiluted Conditioned media from MCA38 cells was analyzed before (pre) and after passage through MCIF-Fc (post-MCIF) and LTβR-Fc (post-LTβR) affinity columns. Fractions (1 mL) eluted from the LTβR (E4–6) and MCIF-Fc (E1–3) affinity columns were diluted 3-fold and tested for binding to LTβR BIAcore chip.

Determination of the LTβR binding by AIM II eluted from LTβR-Fc column is shown in FIG. 13. LTβR and MCIF refer to binding data from LTβR-Fc or MCIF-Fc immobilized BIAcore chip surfaces, respectively. Undiluted Conditioned media from MCA38 cells was analyzed before (pre) and after passage through MCIF-Fc (post-MCIF) and LTβR-Fc (post-LTβR) affinity columns. Fractions (1 mL) eluted from the LTβR (E4–6) and MCIF-Fc (E1–3) affinity columns were diluted 3-fold and tested for binding to LTβR BIAcore chip.

Example 11

Cloning and Expression of Human AIM-II in a Baculovirus Expression System

The cDNA sequence encoding the full length human AIM-II protein, in the deposited clone is amplified using PCR oligonucleotide primers corresponding to the 5' and 3' sequences of the gene:

The 5' has the sequence 5' CGC GGA TCC CGG AGA GAT GGT CAC C 3' (SEQ ID NO:52) containing the underlined BamH1 restriction enzyme site followed by 15 bases of the sequence of AIM-II of SEQ ID NO:38. Inserted into an expression vector, as described below, the 5' end of the amplified fragment encoding human AIM-II provides an efficient signal peptide. An efficient signal for initiatoin of translation in eukaryotic cells, as described by Kozak M., *J. Mol.*, 196: 947–950 (1987) is appropriately located in the vector portion of the construct. The 3' primer has the sequence CGC TCT AGA CCT TCA CAC CAT GAA AGC 3' SEQ ID NO:53) containing the underlined XbaI restriction followed by nucleotides complementary to the last 18 nucleotides of the AIM-II coding sequence set out in SEQ ID NO:38, including the stop codon.

The amplified fragment is isolated from a 1% agarose gel using a commercially available kit ("Geneclean, " BIO 101 Inc., La Jolla, Calif.). The fragment then is digested with BamH1 and Asp718 and again is purified on a 1% agarose gel. This fragment is designated herein F2.

The vector pA2 is used to express the AIM-II protein in the baculovirus expression system, using standard methods, such as those described in Summers et al., A Manual Of Methods For Baculovirus Vectors And Insect Cell Culture Procedures, Texas Agricultural Experimental Station Bulletin No. 1555 (1987). This expression vector contains the strong polyhedrin promoter of the Autographs californica nuclear polyhedrosis virus (AcMNPV) followed by convenient restriction sites. The signal peptide of AcMNPV gp67, including the N-terminal methionine, is located just upstream of a BamH1 site. The polyadenylation site of the simian virus 40 ("SV40") is used for efficient polyadenylation. For an easy selection of recombinant virus the beta-galactosidase gene from E. coli is inserted in the same orientation as the polyhedrin promoter and is followed by the polydenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., Virology, 170:31–39, among others.

The plasmid is digested with the restriction enzymes BamHI and XbaI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosporylated plasmid V2 are ligated together with T4 DNA ligase. E. coli HB101 cells are transformed with ligation mix and spread on culture plates. Bacteria are identified that contain the plasmid with the human AIM-II gene digesting DNA from individual colonies using Bam HI and XbaI and then analyzing the digestion product by gel electrophoresis. The sequence of the cloned fragment is confirmed by DNA sequencing. This plasmid is designated here pBacAIM-II.

5 μg of the plasmid pBacAIM-II is co-transfected with 1.0 μg of a commercially available linearized baculovirus DNA ("BaculoGold™ baculovirus DNA", Pharmingen, San Diego, Calif.), using the lipofection methos described by Felgner et al., Proc. Natl. Acad. Sci. USA 84:7413–7417 (1987). 1 μg of Baculogold™ virus DNA and 5 μg of the plasmid pBacAIM-II are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked backl and forth to mix the newly added solution. The plate is then incubated for 5 hours at 27° C. After 5 hours the transfection solution is removed from the plate amd 1 ml of Grace's insect mediumn supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gel" (Life Technologies Inc., Gaithersburg) is used to allow easy identifcation and isolation of gal-expressing clones, which produce blue-stained plaques. (A detailed descriptionb of a "plaqu assay" of this type can also be found in the user's guide for insect cell culture and baculovirology distributed by Life Technologies Inc., Gaithersburg, page 9–10.

Four days after serial dilution, the virus is added to the cells. After apropriate incubation, blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these cultures dishes are harvested and then they are stored at 4° C. A clone containing properly inserted AIM-II is identified by DNA analysis including restriction mapping and sequencing. This is designated herein as V-AIM-II.

Sf9 cells are grown in Grace's medium supplemented with 10% heat-inactivated FBS. The cells are infected with the recombinant baculovirus V-AIM-II at a multiplicity of infection ("MOI") of about 2 (about 1 to about 3). Six hours later the medium is removed and is replaced with SF900 II medium minus methionine and cystein (available from Life Technologies Inc., Gaithersburg). 42 hours later, 5 μCi of $^{35}$S-methionine and 5 μCi $^{35}$S cysteine (available from Amersham) are added. The cells are further incubated for 16 hours and then they are harvested by centrifugation, lysed and the labeled proteins are visualized by SDS-PAGE and autoradiography.

Example 12

Expression of AIM II in COS Cells

The expression plasmid, AIM-II HA, is made by cloning a cDNA encoding AIM II into the expressison vetor pcDNAI/Amp (which can be obtained from Invitrogen, Inc.).

The expression vector pcDNAI/amp contains (1) an E. coli origin of replication effective for propagation in E. coli and other prokaryotic cells; (2) an ampicillin resistance gene selection of plasmid-containing prokaryotic cells; (3) an SV40 origin of replication for propagation in eukaryotic cells; (4) a CMV promoter, a polylinker, an SV40 intron, and a polydenylation signal arranged so that a cDNA conveniently can be placed under expression control of the CMV promoter and operably linked to the SV40 and the polyadenylation signal by means of restruction sites in the polylinker.

A DNA fragment encoding the entire AIM II precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37:767

(1984). The fusion of the HA tag to the target protein allows easy detection of the recombinant protein with an antibody that recognizes the HA epitope.

The plasmid construction strategy is as follows. The AIM II cDNA of the deposited clone is amplified using primers that contained convenient restriction sites, much as described above regarding the construction of expression vectors for expression of AIM II in E. coli and S. furgiperda. To facilitate detection, purification and characterization of the expressed AIM II, one of the primers contains a hemagglutinin tag ("HA tag") as described above.

Suitable primers include the following, which are used in this example. The 5' primer, containing the uinderlined BamHI site, an AUG start codon and 5 codons thereafter which has the following sequence. 5' CGC CGA TCC ATG GGT CTG GGT CTC TTG 3' (SEQ ID NO:54). The 3' primer, containing the underlined XbaI site and has the following sequence. 5' CGC TCT AGA TCA AGC GTA TGG CAC CAT GAA AGC CCC 3' (SEQ ID NO:55).

The PCR amplified DNA fragment and the vector, pcDNAI/Amp, are disgested with and then ligated. The ligation mixture is transformed into E. coli strain SURE (available from Stratagene Cloning Systems, 1109 North Torrey Pines Road, La Jolla, Calif. 92037) the transformed culture is plated on amplicillin media plates which then are incubated to allow growth of ampicillin resistant colonies. Plasmid DNA is isolated from resistant colonies and examined by restriction analysis and gel sizing for the presence of the AIM II-encoding fragment.

For expression of recombinant AIM II, COS cells are transfected with an expression vector, as described above, using DEAE-DEXTRAN, as described, for instance, in Sambrook et al., Molecular Cloning: A Laboratory Manualk, Cold Spring Laboratory Press, Cold Spring Harbor, N.Y. (1989)

Cells are incubated under conditions for expression of AIM II by the vector. Expression of the AIM II HA fusion protein is detected by radiolabelling and immunoprecipitation, using methods described in, for example, Harlow et al., Antibodies: A Laboratory Manual, 2nd Ed.; Cold Sprin Harbor Laboratory Press, Cold Spring Harbor, N.Y. (1988). To this end, two days after transfection, the cells are labeled by incubation in media containing $^{35}S$-cysteine for 8 hours. The cells and the media are collected, and the cells are washed and the lused with detergent-containing RIPA buffer:150 mM NaCl, 1% NP-40, 0.1% SDS, NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 13

Tissue Distribution of AIM II Expression

Northern blot analysis is carried out to examine the levels of expression of AIM II in human tissues, using methods described by, among other, Sambrook et al., cited above. Total cellular RNA samples are isolated with RNAzol®B system (Biotecx Laboratories, Inc. 6023 South Loop East, Houston, Tex.).

About 10 µg of total RNA is isolated from tissue samples. The RNA is size resolved by electrophoresis through a 1% agarose gel under strongly denaturing conditions. RNA is blotted from the gel onto a nylon filter, and the filter then is prepared for hybridization to a detectably labeled polynucleotide probe.

As a probe to detect mRNA that encodes AIM II, the antisense strand of the coding region of the cDNA insert deposited clone is labeled to a high specific activity. The cDNA is labeled by primer estension, using the Prime-It kit, available from Stratagene. The reaction is carried out using 50 ng of the cDNA, following the standard reaction protocol as recommended by the supplier. The labeled polynucleotide is purified away from other labeled reaction components by column chromatography using a Select-G-50 column, obtained from 5 Prime-3 Prime, Inc. of 5603 Arapahoe Road, Boulder, Co.

The labeled prove is hybridized to filter, at a concentration of 1,000,000 cpm/ml, in a small volume of 7% SDS, 0.5 M NcPO$_4$, pH 7.4 at 65° C., overnight.

Thereafter the prove solution is drained and the filter is washed twice at room temperature and twice at 60° C. with 0.5 X SSC, 0.1% SDS. The filter is then dried and exposed to film −70° C. overnight with an intensifying screen.

Autoradiography shows that mRNA for AIM II is abundant in spleen, bone marrow and thymus.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated polynucleotide consisting of at least 30 contiguous nucleotides of 1 to 624 of SEQ ID NO:38.

2. The polynucleotide of claim 1, ligated to a non-coding sequence.

3. The polynucleotide of claim 1, which encodes a polypeptide.

4. The polynucleotide of claim 3, ligated to a second polynucleotide which encodes a heterologous polypeptide.

5. The polynucleotide of claim 4, wherein said polypeptide is fused to said heterologous polypeptide.

6. A method of producing a vector that comprises inserting the isolated polynucleotide of claim 1 into a vector.

7. A vector comprising the isolated polynucleotide of claim 1.

8. The vector of claim 7, wherein said polynucleotide is operably associated with a heterologuous regulatory sequence.

9. A host cell comprising the isolated polynucleotide of claim 1.

10. The host cell of claim 9, wherein said isolated polynucleotide is operably assoicated with a heterologuous regulatory sequence.

11. A method of producing a polypeptide encoded by a polynucleotide consisting of at least 30 contiguous nucleotides of 1 to 624 of SEQ ID NO:38, said method comprising culturing the host cell of claim 10 under conditions such that said polypeptide is expressed, and recovering said polypeptide.

12. The polynucleotide of claim 1, consisting of at least 50 contiguous nucleotides of 1 to 624 of SEQ ID NO:38.

13. The polynucleotide of claim 12, ligated to a noncoding sequence.

14. The polynucleotide of claim 12, which encodes a polypeptide.

15. The polynucleotide of claim 14, ligated to a second polynucleotide which encodes a heterologous polypeptide.

16. The polynucleotide of claim 15, wherein said polypeptide is fused to said heterologous polypeptide.

17. A method of producing a vector that comprises inserting the isolated polynucleotide of claim 12 into a vector.

18. A vector comprising the isolated polynucleotide of claim 12.

19. The vector of claim 18, wherein said polynucleotide is operably associated with a heterlogous regulatory sequence.

20. A host cell comprising the isolated polynucleotide of claim 12.

21. The host cell of claim 20, wherein said isolated polynucleotide is operably associated with a heterologous regulatory sequence.

22. A method of producing a polypeptide encoded by a polynucleotide consisting of at least 50 contiguous nucleotides of 1 to 624 of SEQ ID NO:38, said method comprising culturing the host cell of claim 21 under conditions such that said polypeptide is expressed, and recovering said polypeptide.

23. An isolated polynucleotide which encodes a polypeptide consisting of at least 30 contiguous amino acids of SEQ ID NO:39.

24. The polynucleotide of claim 23, ligated on a noncoding sequence.

25. The polynucleotide of claim 23, ligated to a second polynucleotide which encodes a heterlogous polypeptide.

26. The polynucleotide of claim 25, wherein said polypeptide is fused to said heterologous polypeptide.

27. A method of producing a vector that comprises inserting the isolated polynucleotide of claim 23 into a vector.

28. A vector comprising the isolated polynucleotide of claim 23.

29. The vector of claim 28, wherein said polynucleotide is operably associated with a heterologous regulatory sequence.

30. A host cell comprising the isolated polynucleotide of claim 23.

31. The host cell of claim 30, wherein said isolated polynucleotide is operably associated with a heterologous regulatory sequence.

32. A method of producing a polypeptide consisting of at least 30 contigous amino acids of SEQ ID NO:39, said method of comprising culturing the host cell of claim 31 under conditions such that said polypeptide is expressed, and recovering said polypeptide.

33. The polypeptide of claim 23, which encodes a polypeptide consisting of at least 50 contigous amino acids of SEQ ID NO:39.

34. The polynucleotide of claim 33, ligated to a noncoding sequence.

35. The polynucleotide of claim 33, liagted to a second polynucleotide which encodes a heterologous polypeptide.

36. The polynucleotide of claim 35, wherein said polypeptide is fused to said heterologous polypeptide.

37. A method of producing a vector that comprises inserting the isolated polynucleotide of claim 33 into a vector.

38. A vector comprising the isolated polynucleotide of claim 33.

39. The vector of claim 38, wherein said polynucleotide is operably associated with a heterologous regulatory sequence.

40. A host cell comprising the isolated polynucleotide of claim 33.

41. The host cell of claim 40, wherein sid isolated polynucleotide is operably associated with a heterologous regulatory sequence.

42. A method of producing a polypeptide consisting of at least 30 contiguous amino acids of SEQ ID NO:39, said method comprising culturing the host cell of claim 41 under conditions such that said polypeptide is expressed, and recovering said polypeptide.

* * * * *

UNITED STATES PATENT AND TRADEMARK OFFICE
CERTIFICATE OF CORRECTION

PATENT NO. : 6,479,254 B2
DATED : November 12, 2002
INVENTOR(S) : Ebner et al.

It is certified that error appears in the above-identified patent and that said Letters Patent is hereby corrected as shown below:

Title page,
Item [56], OTHER PUBLICATIONS, please insert therein -- Harrop, J. *et al.*, "HVEM-L, A Novel Ligand for HVEM/TR2, Stimulates NF-κB Dependent Transcription and T Cell Proliferation, "*J. Int. Cytokine Res.* 18:A-39 (1998). --.
Please insert -- NCBI Entrez, GenBank Report, Accession No. AA491814, from NCI-CGAP (August 1997) --.
Please insert -- NCBI Entrez, GenBank Report, Accession No. AA747757, from NCI-CGAP (February 1998) --.

Column 98,
Lines 9 and 14, please delete "contigous" and insert therein -- contiguous --.
Line 13, please delete "polypeptide" and insert therein -- polynucleotide --.
Line 18, please delete "liagted" and insert therein -- ligated --.
Line 32, please delete "sid" and insert therein -- said --.

Signed and Sealed this

Twentieth Day of May, 2003

JAMES E. ROGAN
*Director of the United States Patent and Trademark Office*